US009023811B2

(12) United States Patent
Mithen

(10) Patent No.: US 9,023,811 B2
(45) Date of Patent: May 5, 2015

(54) METHOD FOR TREATING A CARDIOVASCULAR DISEASE, HYPERCHOLESTEROLEMIA OR HYPERTENSION OR IMPROVING SERUM CHOLESTEROL LEVELS BY ADMINISTERING BROCCOLI WITH A HIGH LEVEL OF GLUSOSINOLATES

(75) Inventor: Richard Mithen, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 13/518,777

(22) PCT Filed: Dec. 23, 2010

(86) PCT No.: PCT/GB2010/052200
§ 371 (c)(1),
(2), (4) Date: Nov. 16, 2012

(87) PCT Pub. No.: WO2011/077163
PCT Pub. Date: Mar. 30, 2011

(65) Prior Publication Data
US 2013/0053332 A1 Feb. 28, 2013

(30) Foreign Application Priority Data

Dec. 23, 2009 (GB) .................................. 0922505.3

(51) Int. Cl.
*A61K 36/31* (2006.01)
*A61K 31/7028* (2006.01)
(52) U.S. Cl.
CPC ............. *A61K 36/31* (2013.01); *A61K 31/7028* (2013.01)
(58) Field of Classification Search
None
See application file for complete search history.

(56) References Cited

FOREIGN PATENT DOCUMENTS

| EP | 2014670 A2 | 1/2009 | |
|---|---|---|---|
| JP | 2009284799 A | 12/2009 | |
| WO | WO-99/52345 A1 | 10/1999 | |
| WO | WO-2006/065723 A2 | 6/2006 | |
| WO | WO-2006/065736 A2 | 6/2006 | |
| WO | WO 2006127903 A1 * | 11/2006 | ............. A01N 65/00 |
| WO | WO-2010/001119 A2 | 1/2010 | |

OTHER PUBLICATIONS

Wilson, P. W., D'Agostino, R. B., Levy, D., Belanger, A. M., Silbershatz, H., & Kannel, W. B. (1998). Prediction of coronary heart disease using risk factor categories. Circulation, 97(18), 1837-1847.*
Christiansen, B., Muguerza, N. B., Petersen, A. M., Kveiborg, B., Madsen, C. R., Thomas, H., . . . & Domínguez, H. (2010). Ingestion of broccoli sprouts does not improve endothelial function in humans with hypertension. PloS one, 5(8), e12461.*
Allender et al., Coronary heart disease statistics, <www.heartstats.org>, 2008 edition, pp. 1-112 (2008).
Ambrosone et al., Breast cancer risk in premenopausal women is inversely associated with consumption of broccoli, a source of isothiocyanates, but is not modified by GST genotype. *J. Nutr.*, 134(5): 1134-8 (2004).
Anderson et al., An updated coronary risk profile, A statement for health professionals. *Circulation*, 83: 356-62 (1991).
Angeloni et al., Modulation of phase II enzymes in sulforaphane: Implications for its cardioprotective potential. *J. Agricult. Food Chem.*, 57(12): 5615-22 (2009).
Awasthi et al., Human glutathione S-transferases. *Int. J. Biochem.*, 26: 295-305 (1994).
Banigesh et al., Therapeutic potential of dietary phase 2 enyzme inducer in hypertension. *Am. J. Hypertension*, 22(Suppl. 1): 16 (2009).
Barberger-Gateau et al., Fish, meat, and risk of dementia: Cohort study. *Brit. Med. J*, 325(7370): 932-3 (2002).
Blacher et al., Aortic pulse wave velocity as a marker of cardiovascular risk in hypertensive patients. *Hypertension*, 33(5): 1111-7 (1999).
Blacher et al., Impact of aortic stiffness on survival in end-stage renal disease. *Circulation*, 99(18): 2434-9 (1999).
Boileau et al., Prostate carcinogenesis in N-methyl-N-nitrosourea (NMU)-testosterone-treated rats fed tomato powder, lycopene, energy-restricted diets. J. Nat. Cancer Inst., 95(21): 1578-86 (2003).
Boutouyrie et al., Importance of arterial stiffness as cardiovascular risk factor for future development of new type of drugs. *Fundam. Clin. Pharmacol.*, 22(3): 241-6 (2008).
BroccoMaxTM, Product information, Jan. 12, 2006.
Clement et al., Prognostic value of ambulatory blood-pressure recordings in patients with treated hypertension. *N. Engl. J. Med.*, 348(24): 2407-15 (2003).
Cohen, A Review of animal model studies of tomato carotenoids, lycopene, and cancer chemoprevention, *Exp. Biol. Med.*, 277: 864-8 (2002).
Conaway et al., Disposition of glucosinolates and sulforaphane in humans after ingestion of steamed and fresh broccoli. *Nutr. Cancer*, 38(2): 168-78 (2000).
Cornelis et al., GSTT1 genotype modifies the association between cruciferous vegetable intake and the risk of myocardial infarction. *Am. J. Clin. Nutr.*, 86(3): 752-8 (2007).
Coronary heart disease, <http://www.dh.gov.uk/en/Healthcare/NationalServiceFrameworks/Coronaryheartdisease/>, Department of Health (2009).
Doggrell et al., Rat models of hypertension, cardiac hypertrophy and failure. *Cardiovasc. Res.*, 39: 89-105 (1998).
Erdman et al., Are the health attributes of lycopene related to its antioxidant function? *Arch. Biochem. Biophys.*, 483(2): 229-35 (2009).

(Continued)

*Primary Examiner* — Shaojia Anna Jiang
*Assistant Examiner* — Dale R Miller
(74) *Attorney, Agent, or Firm* — Marshall, Gerstein & Borun LLP

(57) ABSTRACT

The present invention relates to a composition comprising a high glucosinolate Cruciferous vegetable (such as a high glucosinolate broccoli) having a high level of glucosinolate and/or at least one derivative thereof for use in the treatment or prevention of a cardiovascular disease or for use in promoting heart and/or cardiovascular health.

14 Claims, 19 Drawing Sheets

(56) References Cited

OTHER PUBLICATIONS

Ershler et al., The role of interleukin-6 in certain age-related diseases. *Drugs Aging*, 5(5): 358-65 (1994).
Feskanich et al., Prospective study of fruit and vegetable consumption and risk of lung cancer among men and women. *J. Natl. Cancer Inst.*, 92(22): 1812-23 (2000).
Fowke et al., Urinary isothiocyanate levels, brassica, and human breast cancer. *Cancer Res.*, 63(14): 3980-6 (2003).
Ganji et al., Frequent consumption of milk, yogurt, cold breakfast cereals, peppers, and cruciferous vegetables and intakes of dietary folate and riboflavin but not vitamins B-12 and B-6 are inversely associated with serum total homocysteine concentrations in the US population. *Am. J. Clin. Nutr.*, 80(6): 1500-7 (2004).
Gasper et al., Glutathione S-transferase M1 polymorphism and metabolism of sulforaphane from standard and high-glucosinolate broccoli. *Am. J. Clin. Nutr.*, 82(6): 1283-91 (2005).
Hippisley-Cox et al., Derivation and validation of QRISK, a new cardiovascular disease risk score for the United Kingdom: Prospective open cohort study, *Brit. Med. J.*, 335:136 (2007).
Holick, Vitamin D deficiency. *N. Engl. J. Med.*, 357(3): 266-81 (2007).
Hsueh et al., Recipes for creating animal models of diabetic cardiovascular disease. *Circulation Res.*, 100: 1415-27 (2007).
Hussein et al., Antihypertensive and neuroprotective effects of astaxanthin in experimental animals. *Biol. Pharm. Bull.*, 28(1): 47-52 (2005).
Hutton et al., Cardiovascular disease in England: Opportunities and challenges over the next ten years. Cardio and Vascular Coalition, Ed. C.D.i. England., York: York Health Economic Consortium, University of York (2008).
Jacobs et al., High density lipoprotein cholesterol as a predictor of cardiovascular disease mortality in men and women: the follow-up study of the lipid research clinics prevalence study. *Am. J. Epidemiol,,* 131(1): 32-47 (1990).
Kalmijn et al., Dietary fat intake and the risk of incident dementia in the Rotterdam study. *Ann. Neurol.*, 42(5): 776-82 (1997).
Kang et al., Issues in outcomes research: an overview of randomization techniques for clinical trials. *J. Athl. Train*, 43(2): 215-21 (2008).
Kavanaugh et al., The U.S. Food and Drug Administration's evidence-based review for qualified health claims: tomatoes, lycopene, and cancer. *J. Natl. Cancer Inst.*,99: 1074-85 (2007).
Kelly et al., Effect of reduced aortic compliance on cardiac efficiency and contractile function of in situ canine left ventricle. *Circ. Res.*, 71: 490-502 (1992).
Khoshdel et al., Better management of cardiovascular diseases by pulse wave velocity: Combining clinical practice with clinical research using evidence-based medicine. *Clin. Med. Res.*, 5(1): 45-52 (2007).
Kim et al., Kale juice improves coronary artery disease risk factors in hypercholesterolemic men. *Biomed Environ Sci*, 21(2): 91-7 (2008).
Lakatta et al., Human aging: changes in structure and function. *J. Am. Coll. Cardiol.*, 1987(10): 42A-47A (1987).
Lampe, Health effects of vegetables and fruit: assessing mechanisms of action in human experimental studies. *Am. J. Clin. Nutr.*, 70(3): 475S-490S (1993).
Laurent et al., Arterial stiffness: a new surrogate end point for cardiovascular disease? *J. Nephroi.*, 20(12): S45-50 (2007).
Laurent et al., Aortic stiffness is an independent predictor of all-cause and cardiovascular mortality in hypertensive patients. *Hypertension*, 37(5): 1236-41 (2001).
Laurent et al., Expert consensus document on arterial stiffness: methodological issues and clinical applications. *Eur. Heart J.*, 27(21): 2588-605 (2006).
Law et al., By how much and how quickly does reduction in serum cholesterol concentration lower risk of ischaemic heart disease? *Brit. Med. J.*, 308(6925): 367-72 (1994).
Lee et al., Vitamin D deficiency an important, common, and easily treatable cardiovascular risk factor? *J. Am. Coll. Cardiol.*, 52(24): 1949-56 (2008).
Libby et al., Novel inflammatory markers of coronary risk: theory versus practice. *Circulation*, 100(11): 1148-50 (1999).
Martins et al., Prevalence of cardiovascular risk factors and the serum levels of 25-hydroxyvitamin D in the United States: Data from the Third National Health and Nutrition Examination Survey. *Arch Intern Med*, 167(11): 1159-65 (2007).
McGrath, Ambulatory blood pressure monitoring. *Med. J. Aust.*, 176(12): 588-92 (2002).
Miller et al., Fruits and vegetables and lung cancer: Findings from the European prospective investigation into cancer and nutrition. *Int. J. Cancer*, 108(2): 269-76 (2004).
Milner, Molecular targets for bioactive food components. *J. Nutr.*, 134(9): 2492S-8S (2004).
Mirmiran et al., Fruit and vegetable consumption and risk factors for cardiovascular disease. *Metabolism*, 58(4): 460-8 (2009).
Mithen et al., Diet and Vascular Health, The Broccoli & CVD Study, Protocol Version 4, Oct. 2009.
Mithen et al., Development of isothiocyanate-enriched broccoli, and its enhanced ability to induce phase 2 detoxification enzymes in mammalian cells. *Theor. Appl. Genet.*, 106(4): 727-34 (2003).
Moghasian et al., Advances in experimental dyslipidemia and atherschlerosis, *Lab Invest.*, 81: 1173-83 (2001).
Morris et al., Consumption of fish and n-3 fatty acids and risk of incident Alzheimer disease. *Arch Neurol.*, 60(7): 940-6 (2003).
Mukherjee et al., Broccoli: a unique vegetable that protects mammalian hearts through the redox cycling of the thioredoxin superfamily. *J. Agricult. Food Chem.*, 56(2): 609-17 (2008).
Murashima et al., Phase 1 study of multiple biomarkers for metabolism and oxidative stress after one-week intake of broccoli sprouts. *Biofactors*, 22(1-4): 271-5 (2004).
Narisawa et al., Prevention of N-methylnitrosourea-induced colon carcinogenesis in F344 rats by lycopene and tomato juice rich in lycopene. *Jap. J. Cancer Res.*, 89: 1003-8 (1998).
Nettleton et al., Dietary patterns are associated with biochemical markers of inflammation and endothelial activation in the multi-ethnic study of atherosclerosis (MESA). *Am. J. Clin. Nutr.*, 83(6): 1369-79 (2006).
Neuhouser et al., Fruits and vegetables are associated with lower lung cancer risk only in the placebo arm of the beta-carotene and retinol efficacy trial (CARET). *Cancer Epidemiol. Biomarkers Prev.*, 12(4): 350-8 (2003).
O'Brien et al., Use and interpretation of ambulatory blood pressure monitoring: recommendations of the British hypertension society. *Brit. Med. J.*, 320(7242): 1128-34 (2002).
Ohtsuka et al., Chronically decreased aortic distensibility causes deterioration of coronary perfusion during increased left ventricular contractility. *J. Am. Coll. Cardiol.*, 24: 1406-14 (1994).
O'Kennedy et al., Effects of antiplatelet components of tomato extract on platelet function in vitro and ex vivo: a time-course cannualtion study in healthy humans. *Am. J. Clin. Nutrition*, 84: 570-9 (2006).
O'Kennedy et al., Effects of tomato extract on platelet function: a double-blinded crossover study in healthy humans. *Am. J. of Clin. Nutrition*, 84: 561-9 (2006).
Pepys et al., C-reactive protein: A critical update. *J. Clin. Invest.*, 111(12): 1805-12 (2003).
Petr et al., Lycopene and risk of cardiovascular disease, in L Packer (eds) et al., Carotenoids and Reinoids: Molecular Aspects and Health Issues, AOCS Press, Champaign, p. 204-17 (2004).
Plutzky, Inflammatory pathways in atherosclerosis and acute coronary syndromes. *Am J Cardiol.*, 88(8A): 10K-15K (2001).
Rajkumar et al., Hormonal therapy improves arterial compliance in post menopausal women. *J. Am. Coll. Cardio.I*, 39: 350-6 (1997).
Ridker, Clinical application of C-reactive protein for cardiovascular disease detection and prevention. *Circulation*, 107(3): 363-9 (2003).
Ross, Atherosclerosis is an inflammatory disease. *Am. Heart J.*, 138(5 Pt 2): S419-20 (1999).
Ross, Atherosclerosis—an inflammatory disease. *N. Engl. J. Med.*, 340(2): 115-26 (1999).
Ryberg et al., Genotypes of glutathione transferase M1 and P1 and their significance for lung DNA adduct levels and cancer risk. *Carcinogenesis*, 18(7): 1285-9 (1997).

(56) References Cited

OTHER PUBLICATIONS

Sarikamis et al., High glucosinolate broccoli: a delivery system for sulforaphane. *Molec. Breeding*, 18(3): 219-28 (2006).
Schaefer, Lipoproteins, nutrition, and heart disease. *Am. J. Clin. Nutr.*, 75(2): 191-212 (2002).
Smulyan et al., Systolic blood pressure revisited. *J. Am. Coll. Cardiol.*, 29: 1407-13 (1997).
Steinmetz et al., Vegetables, fruit, and cancer. I. Epidemiology. *Cancer Causes Control*, 2(5): 325-57 (1991).
Steinmetz et al., Vegetables, fruit, and cancer. II. Mechanisms. *Cancer Causes Control*, 2(6): 427-42 (1991).
Stroewsand, Bioactive organosulfur phytochemical in *Brassica oleracea* vegetables—A review. *Food Chem. Toxicol.*, 33: 537-43 (1995).
Suido et al., A mixed green vegetable and fruit beverage decreased the serum level of low-density lipoprotein cholesterol in hypercholesterolemic patients. *J. Agric. Food Chem.*, 50(11): 3346-50 (2002).
Surh, Cancer chemoprevention with dietary phytochemicals. *Nat. Rev. Cancer*, 3(10): 768-80 (2003).
Sutton-Tyrrell et al., Aortic stiffness is associated with visceral adiposity in older adults enrolled in the study of health, aging, and body composition. *Hypertension*, 38(3): 429-33 (2001).
Takai et al., [LDL-cholesterol-lowering effect of a mixed green vegetable and fruit beverage containing broccoli and cabbage in hypercholesterolemic subjects]. *Rinsho Byori*, 51(11): 1073-83 (2003).
Taves, Minimization: a new method of assigning patients to treatment and control groups. *Clin. Pharmacol. Ther.*, 15(5): 443-53 (1974).
Tracy, Inflammation in cardiovascular disease: Cart, horse, or both? *Circulation*, 97(20): 2000-2 (1998).
Traka, Plant science and human nutrition: Challenges in assessing health-promoting properties of phytochemicals. *Plant Cell*, 23: 2483-97 (2011).
Traka et al., Broccoli consumption interacts with GSTM1 to perturb oncogenic signalling pathways in the prostate. *PLoS ONE*, 3(7): e2568 (2008).
Tucker et al., Dietary intake pattern relates to plasma folate and homocysteine concentrations in the Framingham heart study. *J. Nutr.*, 126(12): 3025-31 (1996).
Uren et al., High cholesterol level (hypercholesterolaemia). Available from: <http://www.netdoctor.co.uk/diseases/facts/hypercholesterolemia.htm> Apr. 7, 2008.
van Poppel et al., *Brassica* vegetables and cancer prevention. Epidemiology and mechanisms. *Adv. Exp. Med. Biol.*, 472: 159-68 (1999).
Vasanthi et al., Potential health benefits of broccoli a chemico-biological overview, *Mini-Rev. Med. Chem.*, 9(6): 749-59 (2009).
Verhoeven et al., Epidemiological studies on *Brassica* vegetables and cancer risk. *Cancer Epidemiol. Biomarkers Prev.*, 5(9): 733-48 (1996).
Volpato et al., Cardiovascular disease, interleukin-6, and risk of mortality in older women: The women's health and aging study. *Circulation*, 103(7): 947-53 (2001).
Voorrips et al., Vegetable and fruit consumption and risks of colon and rectal cancer in a prospective cohort study: The Netherlands cohort study on diet and cancer. *Am. J. Epidemiol.*, 152(11): 1081-92 (2000).
Wald et al., Serum cholesterol and ischaemic heart disease. *Atherosclerosis*, 118: S1-5 (1995).
Wang et al., Vitamin D deficiency and risk of cardiovascular disease. *Circulation*, 117(4): 503-11 (2008).
Weber et al., Arterial stiffness, wave reflections, and the risk of coronary artery disease. *Circulation*, 109: 184-9 (2004).
Werner et al., LDL-cholesterol: a risk factor for coronary artery disease—from epidemiology to clinical trials. *Can. J. Cardiol.*, 14(Suppl B): 3B-10B (1998).
White, Importance of aggressive blood pressure lowering when it may matter most. *Am. J. Cardiol.*, 100(3A): 10J-16J (2007).
Williams et al., British hypertension society guidelines for hypertension management 2004 (BHS-IV): Summary. *Brit. Med. J.*, 328(7440): 634-40 (2004).
Wilson et al., Prediction of coronary heart disease using risk factor categories. *Circulation*, 97(18): 1837-47 (1998).
Wood et al., JBS 2: Joint British Societies' Guidelines on Prevention of Cardiovascular Disease in Clinical Practice, prepared by British Cardiac Society, British Hyptertension Society, Diabetes UK, Heart UK, Primary Care Cardiovascular Society, The Stroke Association, *Heart*, 91(1-52): (2005).
Wu et al., Dietary approach to attenuate oxidative stress, hypertension and inflammation in the cardiovascular system. *Proc. Natl. Acad. Sci. USA*, 101(18): 7094-9 (2004).
Wu et al., The impaired glutathione system and its up-regulation by sulforaphane in vascular smooth muscle cells from spontaneously hypertensive rats. *J. Hypertension*, 19(10): 1819-25 (2001).
Yamey, Test your knowledge: Ten questions on primary prevention of cardiovascular disease. 3(3): e214 (2006).
Yochum et al., Dietary flavonoid intake and risk of cardiovascular disease in postmenopausal women. *Am. J. Epidemiol.*, 149(10): 943-9 (1999).
Yudkin et al., C-reactive protein in healthy subjects: associations with obesity, insulin resistance, and endothelial dysfunction: A potential role for cytokines originating from adipose tissue? *Arterioscler. Thromb. Vasc. Biol.*, 19(4): 972-8 (1999).
Zhao et al., Sulforaphane reduces infarct volume following focal cerebral ischemia in rodents. *Neurosci. Lett.*, 393(2-3): 108-12 (2006).
Zittermann, Vitamin D and disease prevention with special reference to cardiovascular disease. *Prog. Biophys. Mol. Biol.*, 92(1): 39-48 (2006).
Galgano et al., The influence of processing and preservation on the retention of health-promoting compounds in broccoli, J. Food Sci., 72(2):S130-5 (2007).
Zakkar et al., Activation of Nrf2 in endothelial cells protects arteries from exhibiting a proinflammatory state, Arterioscler. Thromb. Vasc. Biol., 29(11):1851-7 (2009).

* cited by examiner

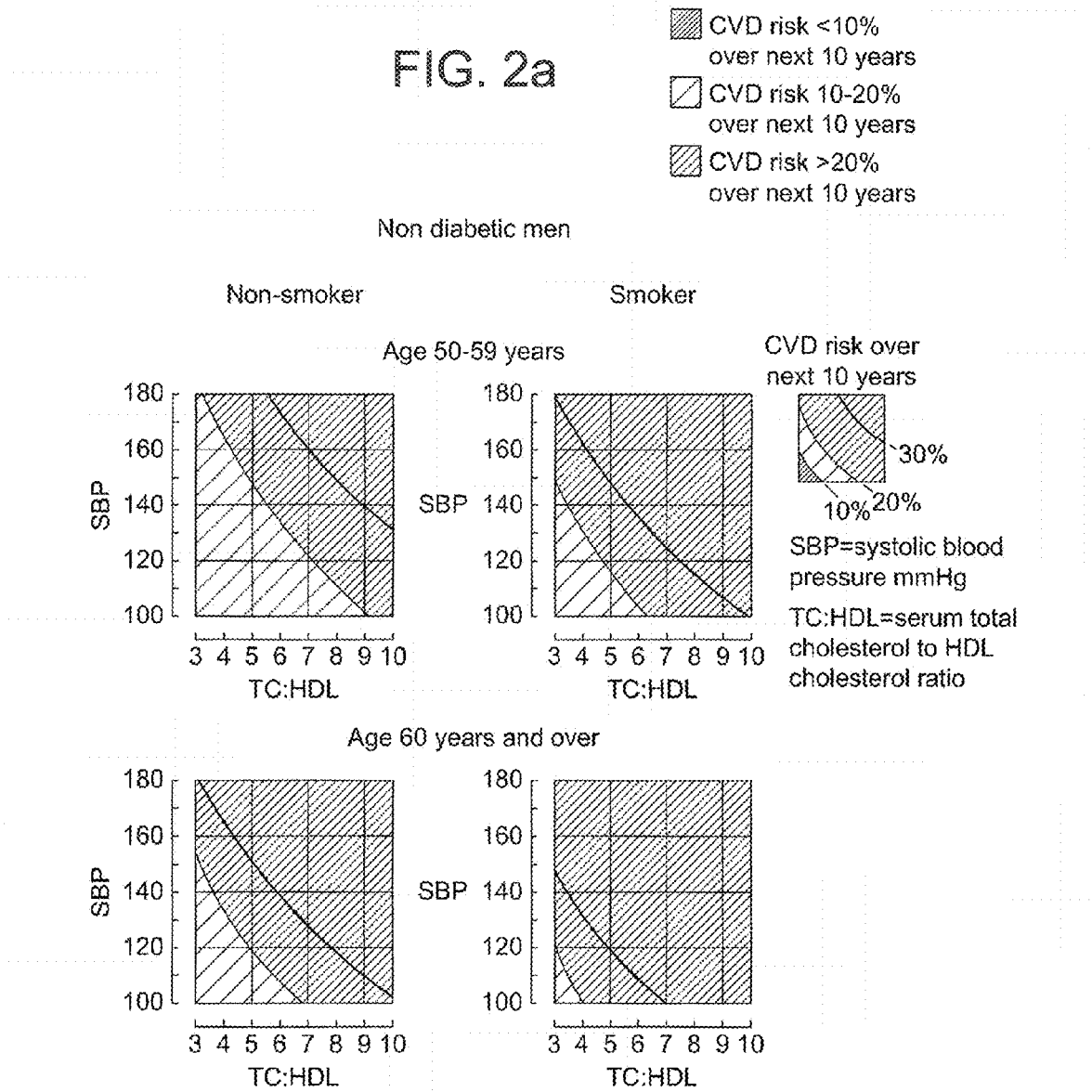

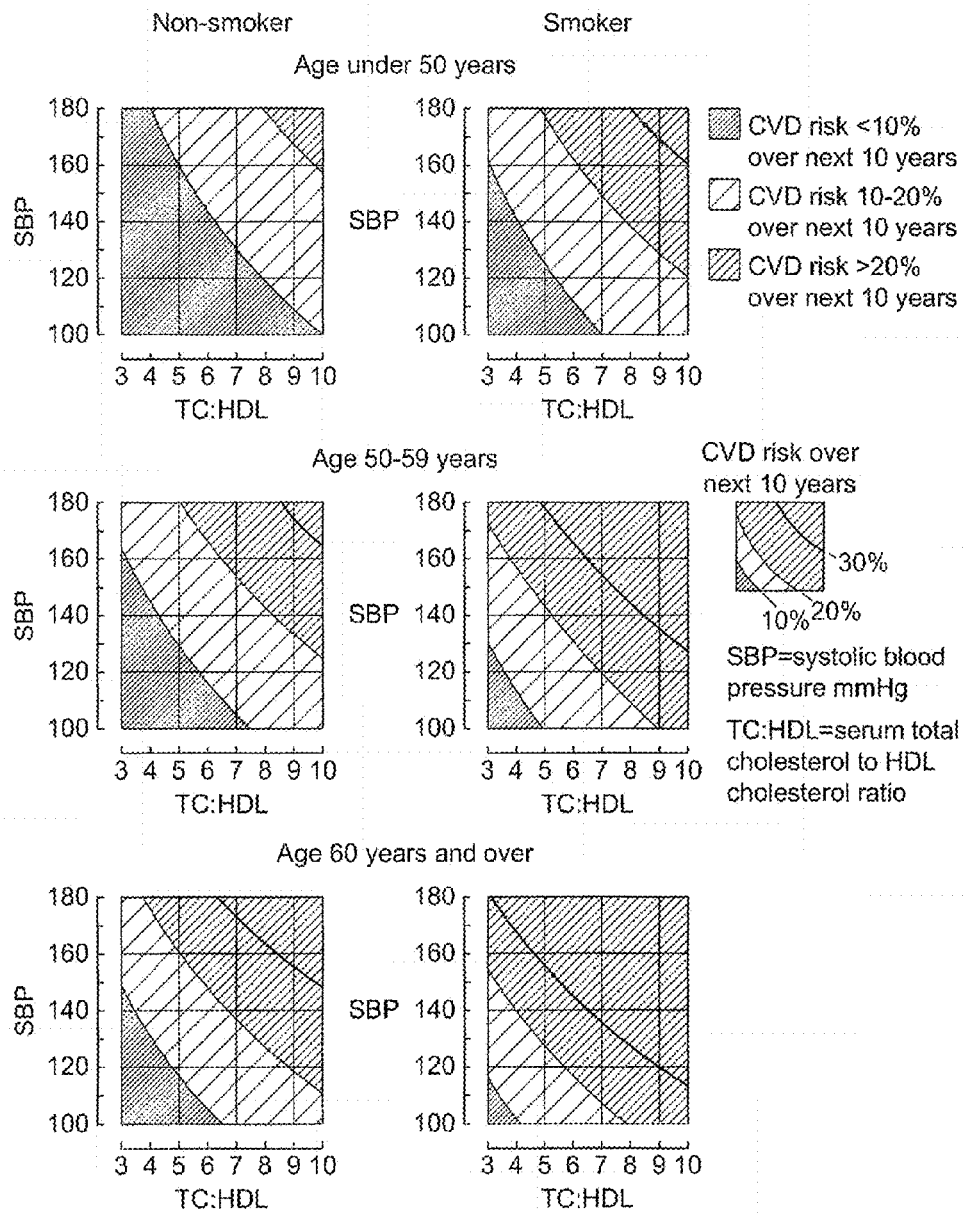

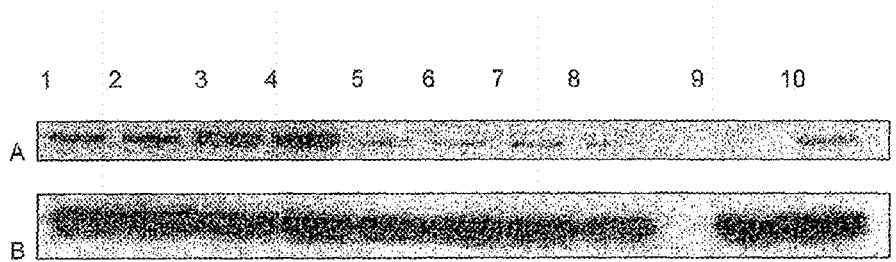

FIG. 13

Primers and probes for genotype analysis.

Gene     Sequence                                              Primer & probe (nM)

GSTM1 - glutathione S-transferase M1
    F   5'- GGAGACAGAAGAGGAGAAGATTCG -3'    500
    R   5'- TGCCCAGCTGCATATGGTT -3'    500
    P   5'- TCCATGGTCTGGTTCTCCAAAATGTCCA -3'    200

Control gene (BRCA1)
    F   5'- GTCTGCTTTTACATCTGAACCTCTGT -3'    500
    R   5'- AGCCCTGAGCAGTCTTCAGAGA -3'    500
    P   5'- ACTCTCACACCCAGATGCTGCTTCACCT -3'    200

Sequences and concentration of forward (F) and reverse (R) primers and fluorogenic probes (P) for the determination of GSTM1 gene deletion are shown. Probes were labelled with a 5' reporter dye, FAM (6-carboxyfluorescein) and a 3' quencher dye, TAMRA (6-carboxytetramethylrhodamine). Triplicate reactions were carried out in a total volume of 25 μL/well consisting of Universal MasterMix, primers and probes and 50 ng DNA. Amplitaq Gold activation for 10 min at 95°C, followed by 40 cycles PCR of denaturation for 15 s at 95°C and annealing/extension for 1 min at 60°C.

FIG. 14

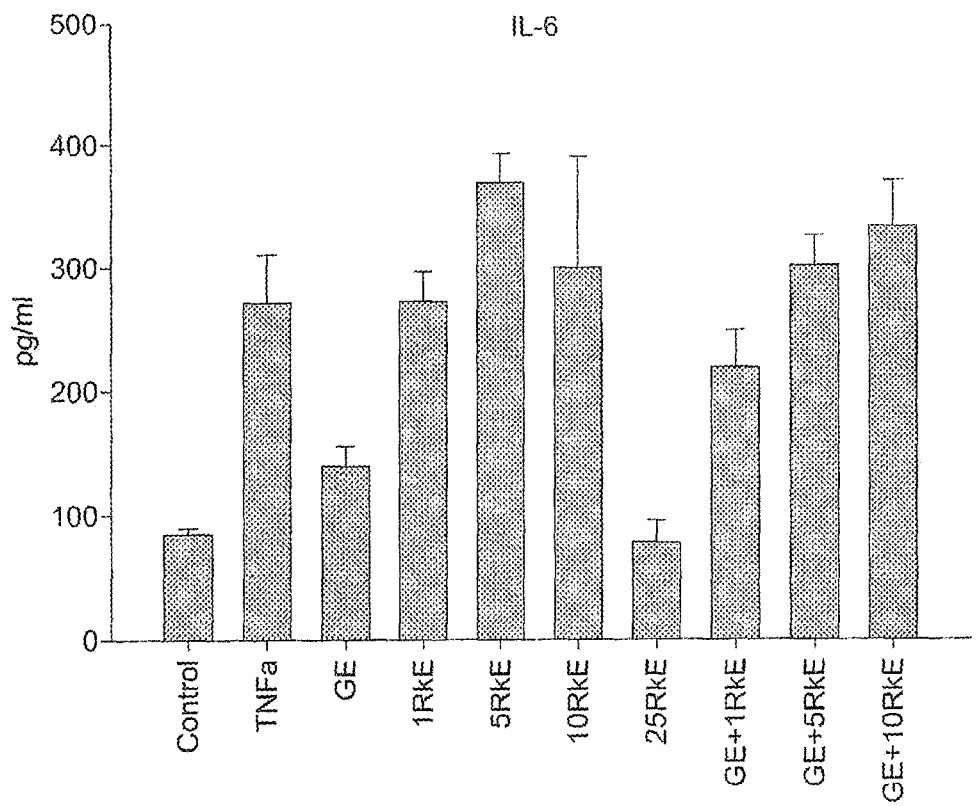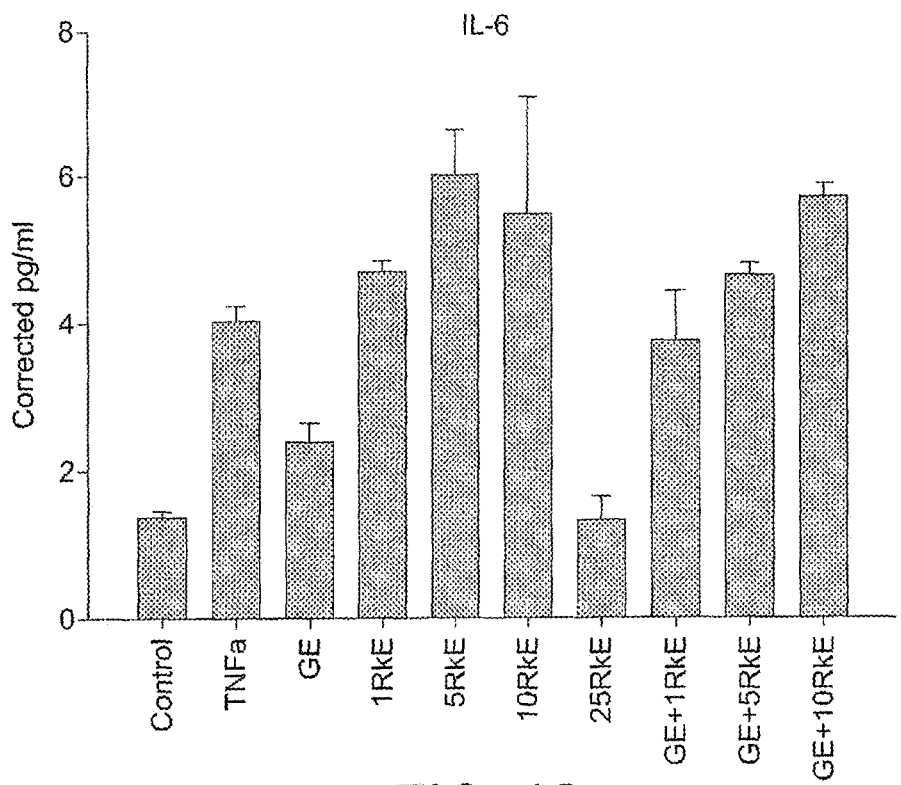
FIG. 16

Calibration with BSA

| pg/ml Protein | Abs 550nm | Bkg Subtracted |
|---|---|---|
| 0 | 0.046 | 0.031 |
| 3.12 | 0.034 | 0.019 |
| 6.25 | 0.059 | 0.044 |
| 12.5 | 0.119 | 0.104 |
| 25 | 0.237 | 0.222 |
| 50 | 0.375 | 0.36 |
| 100 | 0.785 | 0.77 |
| 300 | 2.049 | 2.034 | a= 0.0068
b= 0.0282

IL-6 Standard Curve
$y = 0.0068x + 0.0282$
$R^2 = 0.9978$

| | O.D 450nm | Bkg subtracted | pg/ml | ug protein/100 ul | corrected pg/ml |
|---|---|---|---|---|---|
| C1 | 0.652 | 0.606 | 84.97059 | 57.67 | 1.473 |
| C2 | 0.683 | 0.637 | 89.52941 | 66.56 | 1.345 |
| C3 | 0.628 | 0.582 | 81.44118 | 62.00 | 1.314 |
| TNFa-1 | 1.751 | 1.705 | 246.5882 | 64.94 | 3.797 |
| TNFa-2 | 2.225 | 2.179 | 316.2941 | 75.00 | 4.217 |
| TNFa-3 | 1.773 | 1.727 | 249.8235 | 61.78 | 4.044 |
| GE-1 | 1.145 | 1.099 | 157.4706 | 63.78 | 2.469 |
| GE-2 | 0.947 | 0.901 | 128.3529 | 61.22 | 2.097 |
| GE-3 | 0.97 | 0.924 | 131.7353 | 51.17 | 2.575 |
| 1RkE-1 | 1.765 | 1.719 | 248.6471 | 51.50 | 4.828 |
| 1RkE-2 | 2.095 | 2.049 | 297.1765 | 63.17 | 4.705 |
| 1RkE-3 | 1.918 | 1.872 | 271.1471 | 59.72 | 4.540 |
| 5RkE-1 | 2.504 | 2.458 | 357.3235 | 67.89 | 5.263 |
| 5RkE-2 | 2.77 | 2.724 | 396.4412 | 62.61 | 6.332 |
| 5RkE-3 | 2.483 | 2.437 | 354.2353 | 55.56 | 6.376 |
| 10RkE-1 | 2.033 | 1.987 | 288.0588 | 50.00 | 5.761 |
| 10RkE-2 | 2.77 | 2.724 | 396.4412 | 57.44 | 6.901 |
| 10RkE-3 | 1.55 | 1.504 | 217.0294 | 58.33 | 3.721 |
| 25RkE-1 | 0.522 | 0.476 | 65.85294 | 53.94 | 1.221 |
| 25RkE-2 | 0.745 | 0.699 | 98.64706 | 53.00 | 1.861 |
| 25RkE-3 | 0.53 | 0.484 | 67.02941 | 47.72 | 1.405 |
| GE+1RkE-1 | 1.793 | 1.747 | 252.7647 | 55.94 | 4.518 |
| GE+1RkE-2 | 1.412 | 1.366 | 196.7353 | 60.72 | 3.240 |
| GE+1RkE-3 | 1.491 | 1.445 | 208.3529 | 59.67 | 3.492 |
| GE+5RkE-1 | 2.287 | 2.241 | 325.4118 | 68.39 | 4.758 |
| GE+5RkE-2 | 2.141 | 2.095 | 303.9412 | 68.06 | 4.466 |
| GE+5RkE-3 | 1.955 | 1.909 | 276.5882 | 59.00 | 4.688 |
| GE+10RkE-1 | 2.087 | 2.041 | 296 | 54.11 | 5.470 |
| GE+10RkE-2 | 2.604 | 2.558 | 372.0294 | 64.33 | 5.783 |
| GE+10RkE-3 | 2.341 | 2.295 | 333.3529 | 57.39 | 5.809 |

…

METHOD FOR TREATING A CARDIOVASCULAR DISEASE, HYPERCHOLESTEROLEMIA OR HYPERTENSION OR IMPROVING SERUM CHOLESTEROL LEVELS BY ADMINISTERING BROCCOLI WITH A HIGH LEVEL OF GLUSOSINOLATES

FIELD OF INVENTION

The present invention relates to the use of a high glucosinolate Cruciferous vegetable, such as a high glucosinolate broccoli, for the prevention and/or treatment of a cardiovascular disorder.

BACKGROUND

Cardiovascular disease (CVD) is one of the main causes of early death in the United Kingdom [1]. In England more than 110,000 people die every year of coronary heart disease (CHD). More than 1.4 million people suffer from angina and 275,000 people have a heart attack annually. CVD has a complex aetiology, and usually results in a narrowing of the arteries (atherosclerosis) and an occlusion through the formation of a blood clot in a narrowed artery (thrombosis) [3]. These events have been found to be associated with changes in vascular reactivity, increasing platelet aggregation, increases in plasma triglycerides and an increase in systemic markers of inflammation [4-7]. Of these, inflammation is of central importance, and may underpin the development of other forms of chronic disease such as cancer and cognitive decline [8].

Dietary advice to consume at least five portions of fruit and vegetable per day in order to reduce the risk of developing these chronic diseases is largely based upon observational data from epidemiological studies that have associated diets rich in fruits and vegetables with a reduction in age related chronic illness [8].

There is now a substantial body of epidemiological evidence that states that diets rich in cruciferous vegetables can reduce the risk of incidence and progression of cancer at various sites [12-18].

Broccoli or calabrese (*Brassica oleracea* var *italica*) is a representative member of the cruciferous vegetables. This family of vegetables is unique in the synthesis and accumulation of glucosinolates in their edible parts [34]. These sulphur containing glycosides are stored within the cell vacuole. Following tissue damage they are hydrolysed via a plant thioglucosidase (myrosinase) to several products, of which isothiocyanates from methionine-derived glucosinolates and indoles from tryptophan-derived glucosinolates are the most abundant [35]. If myrosinase has been denatured by blanching prior to freezing or by cooking, ingested glucosinolates are hydrolysed to isothiocyanates and indoles by the action of microbial thioglucosidases in the colon. These degradation products are highly bioactive, and many of the health benefits of cruciferous vegetables have been associated with the activity of these compounds, although experimental data in humans is almost entirely absent. *Brassica* vegetables are also particularly good sources of other compounds that have been associated with health benefits, notably vitamin C, folates, carotenoids, calcium and magnesium [36, 37]. Distinguishing the biological activity of any one group of compounds in food products such as broccoli is very complex. However, to facilitate studies on glucosinolates, cultivars of broccoli that specifically have elevated levels of methionine-derived glucosinolates compared to standard broccoli, but without any change in other potentially bioactive compounds have been developed [38, 39]. Thus, these novel genotypes can be used to test hypotheses in humans concerned with the contribution of a single class of bioactive compound within a complex food.

Several epidemiological studies suggest certain polymorphisms within one or more members of the glutathione-S-transferases (GST) gene family can be risk factors for cancer. Variation in this gene family has also been implicated in CVD where several studies have examined the relationship between null genotypes and CVD. There are at present eight classes of GST [42], with the most work carried out on. GST-mu (GSTM1), GST-theta (GSTT1) and GST-pi (GSTT1) and their polymorphisms. Approximately 40% of the population have a homologous deletion of the GSTM1 gene resulting in a null genotype, and 20% has a deletion of the GSTT1 gene. The GST gene family convert reactive electrophiles, by conjugation with glutathione, to compounds that can be excreted from the body more easily. Polymorphisms may therefore impair the defence mechanisms which could result in the development of a large number of diseases including CVD [43]. Polymorphisms with GST have also been shown to interact with cruciferous vegetable consumption to influence cancer risk [43].

As we age, our arteries stiffen which causes an increase in myocardial demand resulting in higher systolic blood pressures and a widening of the pulse pressure. The stiffening process results from structural changes, the degeneration of elastin responsible for the elasticity of the artery and an increase in collagen causing a thickening of the arterial wall [44]. This increase in arterial stiffness and central systolic pressure along with a decrease in coronary artery perfusion pressure dramatically increases the risk of heart attack, stroke and heart failure. Arterial stiffness has also been associated with many of the common risk factors associated with CVD such as age, high blood pressure, smoking, cholesterol levels and obesity, but importantly have also been shown to be independent predictors of cardiovascular morbidity and mortality in several population groups [45]. The measurement of arterial stiffness is increasingly being used as a tool in the clinical assessment of patients with CVD. Augmentation index (Aix) has been shown to be a strong independent risk marker for coronary artery disease and pulse-wave velocity (PWV) has been shown to be an independent predictor of morbidity and mortality in hypertensive patients [46, 47]. Epidemiological and clinical studies have shown that an increase in arterial stiffness is an independent marker of CVD in patients with end-stage renal failure and those with hypertension [46, 48, 49]. Carotid-femoral PWV is considered the gold standard in the direct measurement of arterial stiffness [50, 51].

SUMMARY ASPECTS OF THE PRESENT INVENTION

Aspects of the present invention are presented in the claims and in the following commentary. It has been found that a high glucosinolate Cruciferous vegetable (such as a high glucosinolate broccoli), such as that disclosed in WO99/052345 (incorporated herein by reference), can be used for promoting heart health, more particularly in the treatment or prevention of a disorder, more particularly in the treatment or prevention of a cardiovascular disorder. This may be accomplished for example by including sufficient quantities of such a high glucosinolate Cruciferous vegetable (e.g. high glucosinolate broccoli) as defined herein, or portions thereof, in the diet of people or animals in need thereof, or by administering to such people or animals medicaments prepared from such a high glucosinolate Cruciferous vegetable (e.g. high glucosinolate broccoli) or portions thereof.

The present invention also includes high glucosinolate Cruciferous vegetable plants (such as high glucosinolate broccoli plants) modified in order to increase the level of 3-methylthiopropyl (3-MTP) glucosinolate therein and high glucosinolate Cruciferous vegetable plants (such as high glucosinolate broccoli plants) comprising elevated levels of 3-MTP-glucosinolate compared with unmodified control plants.

DETAILED ASPECTS OF THE PRESENT INVENTION

According to a first aspect of the present invention there is provided a composition comprising a high glucosinolate Cruciferous vegetable (such as a high glucosinolate broccoli) and/or a derivative thereof for use in the treatment or prevention of a cardiovascular disorder. As used herein, the term "Cruciferous vegetable" means a fresh Cruciferous vegetable and/or a processed Cruciferous vegetable and/or an extract of a Cruciferous vegetable.

In the present invention, the inventors have shown that at least systolic blood pressure, diastolic blood pressure, total cholesterol, LDL-cholesterol mmol/L and cardiovascular disease risk (% event in next ten years) can be significantly reduced by administering a high glucosinolate Cruciferous vegetable (such as high glucosinolate broccoli) compared with Cruciferous vegetables comprising standard levels of glucosinolate and/or control (pea) treatments.

In one embodiment the term "Cruciferous vegetable" as used herein means a fresh Cruciferous vegetable.

In a further embodiment the term "Cruciferous vegetable" as used herein means a processed Cruciferous vegetable.

In another embodiment the term "Cruciferous vegetable" as used herein means an extract of a Cruciferous vegetable.

The term "fresh Cruciferous vegetable" as used herein means a Cruciferous vegetable or part thereof either consumed raw or cooked by any suitable method.

The term "processed Cruciferous vegetable" as used herein means a Cruciferous vegetable which has undergone at least one further processing step such as, for example, floreting, individual quick freezing (IQF), maceration, homogenisation, drying, freezing, compacting etc.

"An extract of a Cruciferous vegetable" as used herein refers to a substance or mixture of substances obtained by extracting the whole or part of a fresh Cruciferous vegetable as defined herein and/or by extracting the whole or part of a processed Cruciferous vegetable as defined herein. The extraction may be carried out using a solvent such as ethanol or water. In one embodiment preferably the extract is an aqueous extract. In one embodiment suitably the extract comprises at least the glucosinolates of the Cruciferous vegetable.

As used herein, to the term "broccoli" as used herein means fresh broccoli and/or processed broccoli and/or an extract of broccoli.

In one embodiment the term "broccoli" as used herein means fresh broccoli.

In a further embodiment the term "broccoli" as used herein means processed broccoli.

In another embodiment the term "broccoli" as used herein means an extract of broccoli.

The term "fresh broccoli" as used herein means broccoli inflorescences and stems either consumed raw or cooked by any suitable method.

The term "processed broccoli" as used herein means broccoli which has undergone at least one further processing step such as, for example, floreting, individual quick freezing (IQF), maceration, homogenisation, drying, freezing, compacting etc.

"An extract of broccoli" as used herein refers to a substance or mixture of substances obtained by extracting the whole or part of fresh broccoli as defined herein and/or by extracting the whole or part of processed broccoli as defined herein. The extraction may be carried out using a solvent such as ethanol or water. In one embodiment preferably the extract is an aqueous extract. In one embodiment suitably the extract comprises at least the glucosinolates of the broccoli.

As used herein, the terms "administer", "administering", "treating" or "treated" include making available for consumption, optionally in a set dietary regimen at an adequate dosage to achieve a desired physiological effect, adequate quantities of said high glucosinolate Cruciferous vegetable (such as high glucosinolate broccoli), as defined herein, including a fresh high glucosinolate Cruciferous vegetable or portions thereof (such as fresh high glucosinolate broccoli or portions thereof), a processed high glucosinolate Cruciferous vegetable or portions thereof (such as processed high glucosinolate broccoli or portions thereof), extracts of a high glucosinolate Cruciferous vegetable (such as extracts of a high glucosinolate broccoli), or medicaments prepared from such a high glucosinolate Cruciferous vegetable (such as a high glucosinolate broccoli).

Without wishing to be bound by any theory, the inventors believe that the one or more phytochemicals and/or the at least one derivative thereof present in the high glucosinolate Cruciferous vegetable (e.g. high glucosinolate broccoli) for use in the methods and uses of the present invention act by modifying an extracellular signalling protein. It will be understood that this is not considered to be the exclusive mode of operation of the broccoli described herein for purposes of treating or preventing cardiovascular disease.

In another aspect of the present invention there is provided a use of a composition comprising a Cruciferous vegetable having a high level of glucosinolate (such as a broccoli having a high level of glucosinolate) and/or at least one derivative thereof in the manufacture of a medicament for the treatment or prevention of a cardiovascular disorder.

In a further aspect of the present invention there is provided a method for the treatment or prevention of a cardiovascular disorder which method comprises administering to a subject an effective amount of a Cruciferous vegetable having a high level of glucosinolate (such as a broccoli having a high level of glucosinolate) and/or at least one derivative thereof.

As used herein, reference to a Cruciferous vegetable having a high level of glucosinolate (such as a broccoli having a high level of glucosinolate) and/or at least one derivative thereof, refers to broccoli having an increased level of at least one phytochemical selected from a list comprising: 4-methylsulphinylbutyl glucosinolate, 3-methylsulphinylpropyl glucosinolate, 4-methylthiobutyl glucosinolate; 3-methylthiopropyl glucosinolate, sulforaphane, erucin, sativin, iberin, β-phenylethylisothiocyanate (PE-ITC), 3-methylthiopropyl isothiocyanate.

In a further aspect of the present invention there is provided a composition comprising a Cruciferous vegetable having a high level of glucosinolate (such as a broccoli having a high level of glucosinolate) and/or at least one derivative thereof for use in management of cardiovascular health or cardiovascular disease progression or enhancing cardiovascular health and wellness by modulating an extracellular signalling protein. Suitably, the signalling protein may be, but is not limited to, one or more of transforming growth factor β1 (TGFβ1), epidermal growth factor (EGF) or insulin.

In a further aspect of the present invention there is provided a use of a composition comprising a Cruciferous vegetable having a high level of glucosinolate (such as a broccoli having a high level of glucosinolate) and/or at least one derivative thereof in the manufacture of a medicament for use in the management of cardiovascular health or cardiovascular disease progression or enhancing cardiovascular health and wellness by modulating an extracellular signalling protein. Suitably, the signalling protein may be, but is not limited to, one or more of TGFβ1, EGF or insulin.

In a further aspect of the present invention there is provided a method for managing the cardiovascular health or cardiovascular disease progression or enhancing cardiovascular health and wellness of a subject which method comprises administering to a subject an effective amount of a Cruciferous vegetable having a high level of glucosinolate (such as a broccoli having a high level of glucosinolate) and/or at least one derivative thereof such that said one or more extracellular signalling proteins are thereby covalently modified.

According to another aspect of the present invention there is provided a composition comprising a Cruciferous vegetable having a high level of glucosinolate (such as a broccoli having a high level of glucosinolate) and/or at least one derivative thereof for use in reducing the levels of inflammatory markers and proteins associated with inflammation, such as for example C-reactive protein (CRP) and cytokines associated with inflammation, including but not limited to interleukin-6 (IL-6).

In another aspect of the present invention there is provided a use of a composition comprising a Cruciferous vegetable having a high level of glucosinolate (such as a broccoli having a high level of glucosinolate) and/or at least one derivative thereof in the manufacture of a medicament for use in reducing the levels of inflammatory markers and proteins associated with inflammation, such as for example CRP and cytokines associated with inflammation, including but not limited to IL-6.

In a further aspect of the present invention there is provided a method for reducing the levels of inflammatory markers and proteins associated with inflammation, (such as for example CRP and cytokines associated with inflammation, including but not limited to IL-6) which method comprises administering to a subject an effective amount of a Cruciferous vegetable having a high level of glucosinolate (such as a broccoli having a high level of glucosinolate) and/or at least one derivative thereof such that said one or more extracellular signalling proteins are thereby covalently modified.

In a further aspect of the present invention there is provided a composition comprising a Cruciferous vegetable having a high level of glucosinolate (such as a broccoli having a high level of glucosinolate) and/or at least one derivative thereof for use in improving or controlling the level of a mammalian serum cholesterol, such as the level of total cholesterol (TC) and/or the level of low density lipoprotein-cholesterol (LDL-cholesterol). In particular, the level of the mammalian serum cholesterol, e.g. of total cholesterol (TC) and/or of LDL-cholesterol can be lowered or prevented from increasing (i.e. maintained at healthy levels)—e.g. compared with the level in a subject not treated with a Cruciferous vegetable having a high level of glucosinolate (such as a broccoli having a high level of glucosinolate) and/or at least one derivative thereof.

In another aspect of the present invention there is provided a use of a composition comprising a Cruciferous vegetable having a high level of glucosinolate (such as a broccoli having a high level of glucosinolate) and/or at least one derivative thereof in the manufacture of a medicament for use in improving or controlling the level of a mammalian serum cholesterol, such as the level of total cholesterol (TC) and/or the level of LDL-cholesterol. In particular, the level of the mammalian serum cholesterol, e.g. of total cholesterol (TC) and/or of LDL-cholesterol can be lowered or prevented from increasing (i.e. maintained at healthy levels)—e.g. compared with the level in a subject not treated with a Cruciferous vegetable having a high level of glucosinolate (such as a broccoli having a high level of glucosinolate) and/or at least one derivative thereof.

In a further aspect of the present invention there is provided a method for improving or controlling the level of a mammalian serum cholesterol (such as the level of total cholesterol (TC) and/or the level of LDL-cholesterol) which method comprises consuming an effective amount of a Cruciferous vegetable having a high level of glucosinolate (such as a broccoli having a high level of glucosinolate) and/or at least one derivative thereof such that said one or more extracellular signalling proteins are thereby covalently modified. In particular, the level of the mammalian serum cholesterol, e.g. of total cholesterol (TC) and/or LDL-cholesterol can be lowered or prevented from increasing (i.e. maintained at healthy levels)—e.g. compared with the level in a subject not treated with a Cruciferous vegetable having a high level of glucosinolate (such as a broccoli having a high level of glucosinolate) and/or at least one derivative thereof.

According to a further aspect of the present invention there is provided a composition comprising a Cruciferous vegetable having a high level of glucosinolate (such as a broccoli having a high level of glucosinolate) and/or at least one derivative thereof for use in the treatment or prevention of cardiovascular inflammation.

In another aspect of the present invention there is provided a use of a composition comprising a Cruciferous vegetable having a high level of glucosinolate (such as a broccoli having a high level of glucosinolate) and/or at least one derivative thereof in the manufacture of a medicament for use in the treatment or prevention of cardiovascular inflammation.

In a further aspect of the present invention there is provided a method for treating or preventing cardiovascular inflammation which method comprises administering to a subject an effective amount of a Cruciferous vegetable having a high level of glucosinolate (such as a broccoli having a high level of glucosinolate) and/or at least one derivative thereof.

According to a further aspect of the present invention there is provided a composition comprising a Cruciferous vegetable having a high level of glucosinolate (such as a broccoli having a high level of glucosinolate) and/or at least one derivative thereof for use in the treatment or prevention of hypertension.

In another aspect of the present invention there is provided a use of a composition comprising a Cruciferous vegetable having a high level of glucosinolate (such as a broccoli having a high level of glucosinolate) and/or at least one derivative thereof in the manufacture of a medicament for the treatment or prevention of hypertension.

In a further aspect of the present invention there is provided a method for the treatment or preventions of hypertension which method comprises administering to a subject an effective amount of a Cruciferous vegetable having a high level of glucosinolate (such as a broccoli having a high level of glucosinolate) and/or at least one derivative thereof.

In a further aspect of the present invention there is provided a composition comprising a Cruciferous vegetable having a high level of glucosinolate (such as a broccoli having a high level of glucosinolate) and/or at least one derivative thereof for use in reducing cardiovascular risk.

In a further aspect of the present invention there is provided a use of a composition comprising a Cruciferous vegetable having a high level of glucosinolate (such as a broccoli having a high level of glucosinolate) and/or at least one derivative thereof in the manufacture of a medicament for use in reducing cardiovascular risk.

In a further aspect of the present invention there is provided a method for reducing cardiovascular risk in a subject which method comprises administering to a subject an effective amount of a Cruciferous vegetable having a high level of glucosinolate (such as a broccoli having a high level of glucosinolate) and/or at least one derivative thereof.

In a further aspect of the present invention there is provided a composition comprising a Cruciferous vegetable having a high level of glucosinolate (such as a broccoli having a high level of glucosinolate) and/or at least one derivative thereof for use in reducing total serum triglycerides (TG).

In a further aspect of the present invention there is provided a use of a composition comprising a Cruciferous vegetable having a high level of glucosinolate (such as a broccoli having a high level of glucosinolate) and/or at least one derivative thereof in the manufacture of a medicament for use in reducing total serum triglycerides.

In a further aspect of the present invention there is provided a method for reducing total serum triglycerides in a subject which method comprises administering to a subject an effective amount of a Cruciferous vegetable having a high level of glucosinolate (such as a broccoli having a high level of glucosinolate) and/or at least one derivative thereof.

As used herein, in its broadest sense the term cardiovascular disorder or cardiovascular disease refers to any disorder or disease of the heart or vasculature. The terms cardiovascular disorder and cardiovascular disease are used herein interchangeably. More specifically, the term cardiovascular disorder as used herein refers to a chronic disorder affecting the heart or vasculature which has a complex aetiology selected from, for example, one or more of age, diet, environmental factors and/or genetic predisposition. Examples of such disorders are: angina, artherosclerosis, cardiomyopathy or cardiac inflammation, congestive heart failure, coronary artery disease, carotid artery disease, heart attack (coronary thrombosis, myocardial infarction), peripheral artery disease, stroke.

Preferable Aspects

The Cruciferous vegetable having a high level of glucosinolate of the present invention may be provided as a high-glucosinolate broccoli as described in WO99/52345 and PCT/GB2009/001648 both of which are incorporated herein by reference.

Alternatively, the Cruciferous vegetable having a high level of glucosinolate may be a high-glucosinolate Cruciferous vegetable other than broccoli, which high-glucosinolate Cruciferous vegetable may be prepared in accordance with the teachings described in WO99/52345 and PCT/GB2009/001648 both of which are incorporated herein by reference.

Suitably the high glucosinolate Cruciferous vegetable (such as high-glucosinolate broccoli) for use in the present invention comprises increased levels of one or more glucosinolate and/or one or more isothiocyanate.

In one embodiment the high glucosinolate Cruciferous vegetable (such as high-glucosinolate broccoli) and/or at least one derivative thereof for use in the present invention comprises increased levels of one or more of the following compounds: 4-methylsulphinylbutyl glucosinolate (MSB), 3-methylsulphinylpropyl glucosinolate (MSP), 4-methylthiobutyl glucosinolate; 3-methylthiopropyl glucosinolate.

In one embodiment the high glucosinolate Cruciferous vegetable (such as high-glucosinolate broccoli) and/or at least one derivative thereof for use in the present invention comprises increased levels 4-methylsulphinylbutyl glucosinolate (MSB) and/or 3-methylsulphinylpropyl glucosinolate (MSP).

Preferably the high glucosinolate Cruciferous vegetable (such as high-glucosinolate broccoli) and/or at least one derivative thereof for use in the present invention has a level of 4-methylsulphinylbutyl glucosinolate (MSB) which is 2 to 3 times the level of 4-methylsulphinylbutyl glucosinolate (MSB) found in a standard Cruciferous vegetable (such as a standard broccoli) grown under similar conditions.

Preferably the high glucosinolate Cruciferous vegetable (such as high-glucosinolate broccoli) and/or at least one derivative thereof for use in the present invention has a level of 4-3-methylsulphinylpropyl glucosinolate (MSP) which is 2 to 3 times the level of 4-3-methylsulphinylpropyl glucosinolate (MSP) found in a standard Cruciferous vegetable (such as a standard broccoli) grown under similar conditions.

In one embodiment the high glucosinolate Cruciferous vegetable (such as high-glucosinolate broccoli) and/or at least one derivative thereof for use in the present invention comprises increased levels of one or more of the following compounds: sulforaphane, erucin, sativin, iberin, β-phenylethylisothiocyanate (PE-ITC), 3-methylthiopropyl isothiocyanate.

Suitably said high glucosinolate Cruciferous vegetable (such as high-glucosinolate broccoli) and/or derivative thereof may be provided in a set dietary regimen at an adequate dosage known to produce a desired physiological effect.

In one embodiment the high glucosinolate Cruciferous vegetable (such as high-glucosinolate broccoli) and/or derivative thereof is consumed in an amount to provide glucosinolate in an amount of about 60-140 micromoUday, suitably 70-140 micromol/day, suitably 75-140 micromol/day, suitably 80-135 micromol/day, suitably 90-135 micromol/day. Suitably the broccoli having a high level of glucosinolate and/or derivative thereof is consumed in an amount to provide glucosinolate in an amount of about 20 micromoUday or more, 30 micromol/day or more, 40 micromoUday or more, 50 micromol/day or more, 60 micromol/day or more, 75 micromol/day or more, suitably about 79 micromol/day or more, suitably about 100 micromol/day, suitably about 130 micromoUday, suitably about 140 micromol/day.

Preferably the high glucosinolate Cruciferous vegetable (such as high glucosinolate broccoli) and/or derivative thereof has a level of glucosinolate which is 2 to 3 times the level found in a standard Cruciferous vegetable (such as a standard broccoli) grown under similar conditions. Preferably the high glucosinolate Cruciferous vegetable (such as high glucosinolate broccoli) and/or derivative thereof comprises at least one glucosinolate in amount of at least 10 micromol/g dry weight. More preferably at least about 14 μmoles/g dry weight, at least about 16 μmoles/g dry weight, at least about 20 μmoles/g dry weight, at least about 25 μmoles/g dry weight, at least about 30 μmoles/g dry weight, at least about 50 μmoles/g dry weight or at least about 75 μmoles/g dry weight.

Suitably, in one embodiment preferably the high glucosinolate Cruciferous vegetable (such as high-glucosinolate broccoli) in accordance with the present invention has either 4-methylsulphinylbutyl glucosinolate (MSB) and/or 3-methylsulphinylpropyl glucosinolate (MSP) in an amount of at least 10 micromol/g dry weight. More preferably at least about 14 μmoles/g dry weight, at least about 16 μmoles/g dry weight, at least about 20 μmoles/g dry weight, at least about 25 μmoles/g dry weight, at least about 30 μmoles/g dry weight, at least about 50 μmoles/g dry weight or at least about 75 μmoles/g dry weight.

The term "modifying an extracellular signalling protein" as used herein means to alter the natural signalling function of the signalling protein. The term "modifying" may mean inhibit or enhance the signalling function of the extracellular signalling protein. In one embodiment the term "modifying" means inhibit the signalling function of the extracellular signalling protein.

In one embodiment preferably the subject has a genotype which includes the glutathione S-transferase mu 1 (GSTM1) gene and/or glutathione S-transferase theta 1 (GSTT1) gene and/or the glutathione S-transferase pi 1 (GSTP1) gene.

The terms "reducing" or "reduced" and other derivations of "reduce" as used herein mean that there is lowering in the value in a subject treated with a high glucosinolate Cruciferous vegetable (such as high-glucosinolate broccoli) in accordance with the present invention compared with a subject which has not been treated with a high glucosinolate Cruciferous vegetable (such as high-glucosinolate broccoli).

In a preferred embodiment the high glucosinolate Cruciferous vegetable is a high glucosinolate broccoli.

Derivatives

The term derivative as used herein refers to a compound present in the high glucosinolate Cruciferous vegetable (such as high-glucosinolate broccoli) which is derived from a glucosinolate. In one preferred embodiments, the derivative may be an isothiocyanate. Isothiocyanates are sulphur-containing phytochemicals with the general formula R-NCS.

Isothiocyanates occur naturally as glucosinolate conjugates in cruciferous vegetables.

Isothiocyanates of particular interest in the present invention include the following: 4-methylsulphinylbutyl (otherwise known as sulforaphane or SF); 4-methylthiobutyl (otherwise known as crucin); 4-mercaptobutyl (otherwise known as sativin); β-phenylethylisothiocyanate (PE-ITC); iberin (otherwise know as IB), and 3-methylthiopropyl.

In one embodiment it is envisaged that erucin and 3-methylthiopropyl may be particularly preferred isothiocyanates either alone or in combination.

In one embodiment 3-methylthiopropyl is a preferred isothiocyanate.

In another embodiment sativin may be the preferred isothiocyanate.

In one embodiment 4-methylsulphinylbutyl (sulforaphane) is a preferred.

Glucosinolates

The glucosinolates are a class of organic compounds that contain sulphur, nitrogen and a group derived from glucose. They occur as secondary metabolites of many plants of the order Brassicales (especially in the family Brassicaceae), such as Cruciferous vegetables.

Glucosinolates are water-soluble anions and belong to the glucosides. Every glucosinolate contains a central carbon atom which is bonded via a sulphur atom to the glycone group (making a sulfated ketoxime) and via a nitrogen atom to a sulphate group. In addition, the central carbon is bonded to a side group; different glucosinolates have different side groups.

About 120 different glucosinolates are known to occur naturally in plants.

The glucosinolates in accordance with the present invention are preferably aliphatic.

In the present invention it is envisaged that one or more of the following glucosinolates may be of importance: 4-methylsulphinylbutyl glucosinolate, 3-methylsulphinylpropyl glucosinolate, 4-methylthiobutyl glucosinolate and 3-methylthiopropyl glucosinolate.

In one embodiment the glucosinolate is preferably 4-methylsulphinylbutyl glucosinolate (MSB) and/or 3-methylsulphinylpropyl glucosinolate (MSP).

High Glucosinolate Cruciferous Vegetable or High Glucosinolate Broccoli

Suitably the terms "Cruciferous vegetable having a high level of glucosinolate" or "broccoli having a high level of glucosinolate" means a Cruciferous vegetable or broccoli crop, respectively, with an increased level of glucosinolates compared with a traditional variety of that Cruciferous vegetable or of broccoli.

The term "high glucosinolate" in one embodiment means that the Cruciferous vegetable (such as the high glucosinolate broccoli) and/or at least one derivative thereof has a level of 4-methylsulphinylbutyl glucosinolate (MSB) and/or methyl sulphinylpropyl glucosinolate (MSP) which is 2 to 3 times the level of 4-methylsulphinylbutyl glucosinolate (MSB) and/or methylsulphinylpropyl glucosinolate (MSP) found in a standard Cruciferous vegetable (such as a standard broccoli) grown under similar conditions.

Suitably the term "high level of glucosinolate" in one embodiment means that the Cruciferous vegetable (such as the broccoli) comprises between about 10 and about 100 μmoles/g dry weight. Suitably the term high glucosinolate means that the Cruciferous vegetable (such as broccoli) comprises at least about 10 μmoles/g dry weight, suitably at least about 14 μmoles/g dry weight, suitably at least about 16 μmoles/g dry weight, suitably at least about 20 μmoles/g dry weight, suitably at least about 25 μmoles/g dry weight, suitably at least about 30 μmoles/g dry weight, suitably at least about 50 μmoles/g dry weight, suitably at least about 75 μmoles/g dry weight.

The high glucosinolate Cruciferous vegetable (such as high glucosinolate broccoli) may be one as described in Mithen et al Theor. Appl. Genet. (2003) 106, 727-734; Sarikamis et al Molecular Breeding (2006) 18, 219-228, or in WO 99/52345 (incorporated herein by reference).

In one embodiment the high glucosinolate Cruciferous vegetable (such as high glucosinolate broccoli) may comprise 4-methylsulfinylbutyl glucosinolate and/or 3-methylsulfinylpropyl glucosinolate at concentrations of between about 10 and about 100 μmoles/g dry weight, suitably of about 14 and about 100 μmoles/g dry weight, suitably of about 16 and about 100 μmoles/g dry weight, suitably of between about 20 and about 100 μmoles/g dry weight, suitably of between about 30 and about 100 μmoles/g dry weight, suitably of between about 50 and about 100 μmoles/g dry weight.

For example, the level of 4-methylsulfinylbutyl glucosinolate in a high glucosinolate Cruciferous vegetable (such as high glucosinolate broccoli) for instance may be between about 8 to about 55 μmoles/g dry weight, suitably between about 10 to about 55 μmoles/g dry weight, suitably between about 10 to about 40 μmoles/g dry weight. Suitably, the level of 4-methylsulfinylbutyl glucosinolate in a high glucosinolate Cruciferous vegetable (such as high glucosinolate broccoli) for instance may be at least about 8 μmoles/g dry weight, suitably at least about 10 μmoles/g dry weight, suitably at least about 15 μmoles/g dry weight. This contrasts sharply with Cruciferous vegetables (in particular broccoli) available from retail outlets which typically has levels of this glucosinolate in the region of 4-5 μmoles/g dry weight.

For example, the level of 3-methylsulfinylpropyl glucosinolate in a high glucosinolate Cruciferous vegetable (such as a high glucosinolate broccoli) for instance may be between about 1.5 to about 10 µmoles/g dry weight, suitably between about 2 to about 10 µmoles/g dry weight, suitably between about 2 to about 8 µmoles/g dry weight. Suitably, the level of 3-methylsulfinylpropyl glucosinolate in a high glucosinolate Cruciferous vegetable (such as high glucosinolate broccoli) for instance may be at least about 1.5 µmoles/g dry weight, suitably at least about 2 µmoles/g dry weight, suitably at least about 3 µmoles/g dry weight, suitably at least about 4 µmoles/g dry weight, suitably at least about 5 µmoles/g dry weight. This contrasts sharply with Cruciferous vegetables (such as broccoli) available from retail outlets which typically has levels of this glucosinolate in the region of 0.5-1 µmoles/g dry weight.

In one embodiment the levels of glucosinolates in the Cruciferous vegetable (such as the broccoli) is determined by examining all edible parts of the plant, such as both the inflorescences and edible stems for broccoli. In another embodiment the level of glucosinolates in the Cruciferous vegetable (such as broccoli) is determined by examining the leaves only or the inflorescences only or the roots only.

For instance where the Cruciferous vegetable is one where the leaves are mainly eaten—such as rocket, salad rocket, wall rocket, wild rocket, kale or cabbage for instance, then preferably the level of glucosinolates in the Cruciferous vegetable is determined by examining the leaves only.

Where the Cruciferous vegetable is one where the inflorescences are mainly eaten—such as broccoli, Brussel sprouts or cauliflower for instance, then preferably the level of glucosinolates in the Cruciferous vegetable is determined by examining the inflorescences only.

Where the Cruciferous vegetable is one where the roots are mainly eaten—such as radish or turnip for instance, then preferably the level of glucosinolates in the Cruciferous vegetable is determined by examining the edible part of the root only.

Preferably it is at least the broccoli inflorescences (or only the broccoli inflorescences) which are used in the present invention.

In one embodiment the term "high level of glucosinolate" means that the Cruciferous vegetable inflorescences or edible roots or edible leaves contain the high level of glucosinolate, for example of between about 10 and about 100 µmoles/g dry weight. In this embodiment suitably the term high glucosinolate means that the Cruciferous vegetable inflorescences or roots or leaves comprise at least about 10 µmoles/g dry weight, suitably at least about 14 µmoles/g dry weight, at least about 16 µmoles/g dry weight, suitably at least about 20 µmoles/g dry weight, suitably at least about 25 µmoles/g dry weight, suitably at least about 30 µmoles/g dry weight, suitably at least about 50 µmoles/g dry weight, suitably at least about 75 µmoles/g dry weight.

In one embodiment the term "high level of glucosinolate" means that the broccoli inflorescences contain the high level of glucosinolate, for example of between about 10 and about 100 µmoles/g dry weight. In this embodiment suitably the term high glucosinolate means that the broccoli inflorescences comprises at least about 10 µmoles/g dry weight, suitably at least about 14 µmoles/g dry weight, at least about 16 µmoles/g dry weight, suitably at least about 20 µmoles/g dry weight, suitably at least about 25 µmoles/g dry weight, suitably at least about 30 µmoles/g dry weight, suitably at least about 50 µmoles/g dry weight, suitably at least about 75 µmoles/g dry weight.

It will be understood that the term Cruciferous vegetable having a high level of glucosinolate (such as broccoli having a high level of glucosinolate) refers not only to the plant material in its fresh natural state i.e. as whole heads, such as broccoli inflorescences and stems, but also to the Cruciferous vegetable (such as the broccoli) when it has been subjected to one or more further processing steps such as, for example floreting, individual quick freezing (IQF), maceration, homogenization, drying, freezing, compacting etc.

It will further be apparent that the Cruciferous vegetable having a high level of glucosinolate (such as the broccoli having a high level of glucosinolate) can be combined with one or more other vegetables and/or vegetable products, including one or more additional high glucosinolate Cruciferous vegetables.

Cruciferous Vegetables

The skilled person will be aware that plants comprising glucosinolate other than high glucosinolate broccoli are known. Glucosinolate is present in plants from the order Capparales. This order includes about 18 families, of which the Brassicaceae and the Capparaceae are the two largest.

Cruciferous vegetables (e.g. cruciferous vegetable crops) from the family Brassicaceae containing glucosinolate include the following cruciferous vegetable crops:
broccoli
rocket (including *Sisymbrium officinales*; *Eruca sativa* (Salad Rocket), *Diplotaxis erucoides* (Wall Rocket), *Diplotaxis tenuifolia* (Wild Rocket), and *Bunias orientalis* (Turkish Rocket)); and
watercress (including *Rorripa nasturtium aquaticum* and *Nasturtium officinale*).
cauliflower,
kale,
turnip,
collards,
Brussels sprouts,
a cabbage, and
radish.

In one embodiment broccoli having a high level of glucosinolate can be combined with one or more other Cruciferous vegetables and/or Cruciferous vegetable products, including one or more cruciferous vegetable crops.

Extract

In one embodiment there is provided a composition for use in the present invention comprising an extract from the high glucosinolate Cruciferous vegetable (such as high glucosinolate broccoli), which extract also has a high level of glucosinolate.

In one embodiment preferably the extract is a substance or mixture of substances obtained by extracting the whole or part of a fresh high glucosinolate Cruciferous vegetable (such as a high glucosinolate broccoli) as defined herein (including a raw Cruciferous vegetable (such as raw broccoli)) or by extracting the whole or part of a processed Cruciferous vegetable (such as processed broccoli) as defined herein.

The extraction may be carried out using a solvent such as ethanol or water. In one embodiment preferably the extract is an aqueous extract.

Individual/subject

As used herein, the terms "individual" and "subject" refers to vertebrates, particularly members of the mammalian species. The term includes but is not limited to domestic animals, sports animals, primates and humans. In one embodiment preferably the subject is a human.

Therapeutic Uses

The high glucosinolate Cruciferous vegetable (such as the high glucosinolate broccoli) may be used in the treatment or prevention of one or more of the following: angina, artherosclerosis, cardiomyopathy or cardiac inflammation, congestive heart failure, coronary artery disease, carotid artery disease, heart attack (coronary thrombosis, myocardial infarction), high blood pressure/hypertension, hypercholesterolemia/hyperlipidemia, peripheral artery disease, stroke.

In one embodiment the high glucosinolate Cruciferous vegetable (such as the high glucosinolate broccoli) may be used in the treatment or prevention of artherosclerosis.

Therefore in one embodiment the present invention provides a composition comprising a high glucosinolate Cruciferous vegetable (such as a high glucosinolate broccoli) for use in the treatment and/or prevention of angina, artherosclerosis, cardiomyopathy or cardiac inflammation, congestive heart failure, coronary artery disease, carotid artery disease, heart attack (coronary thrombosis, myocardial infarction), high blood pressure/hypertension, hypercholesterolemia/hyperlipidemia, peripheral artery disease, stroke.

In another embodiment the present invention provides a method for treating and/or preventing: angina, artherosclerosis, cardiomyopathy or cardiac inflammation, congestive heart failure, coronary artery disease, carotid artery disease, heart attack (coronary thrombosis, myocardial infarction), high blood pressure/hypertension hypercholesterolemia/hyperlipidemia, peripheral artery disease, stroke comprising administering to a subject an effective amount of a composition comprising a high glucosinolate Cruciferous vegetable (such as a high glucosinolate broccoli).

In one embodiment the present invention provides a composition comprising one or more phytochemicals and/or at least one derivative thereof (in particular one or more glucosinolates and/or isothiocyanates) or a high glucosinolate Cruciferous vegetable (such as a high glucosinolate broccoli) for use in improving or controlling the level of mammalian serum cholesterols wherein the phytochemical and/or derivative thereof or the high glucosinolate Cruciferous vegetable (such as a high glucosinolate broccoli) modifies an extracellular signalling protein. In particular, the level of total cholesterol (TC) and/or LDL-cholesterol can be lowered or prevented from increasing (i.e. maintained at healthy levels)—e.g. compared with the level in a subject not treated with phytochemicals and/or at least one derivative or the high glucosinolate Cruciferous vegetable (such as a high glucosinolate broccoli).

In another embodiment the present invention provides a method for improving or controlling the level of a mammalian serum cholesterol comprising administering to a subject an effective amount of a composition (preferably a pharmaceutical composition) comprising one or more phytochemicals and/or at least one derivative thereof (in particular one or more glucosinolates and/or isothiocyanates) or an effective amount of high glucosinolate Cruciferous vegetable (such as a high glucosinolate broccoli) wherein the phytochemical and/or derivative thereof or high glucosinolate Cruciferous vegetable (such as a high glucosinolate broccoli) modifies an extracellular signalling protein.

Cardiovascular Disorder (CVD)

As used herein, in its broadest sense the term cardiovascular disorder or cardiovascular disease refers to any disorder or disease of the heart or vasculature. The terms cardiovascular disorder and cardiovascular disease are used herein interchangeably.

More specifically, the term cardiovascular disorder as used herein refers to a chronic disorder affecting the heart or vasculature which has a complex aetiology selected from, for example, one or more of age, diet, environmental factors and/or genetic predisposition. Examples of such disorders are: angina, artherosclerosis, cardiomyopathy or cardiac inflammation, congestive heart failure, coronary artery disease, carotid artery disease, heart attack (coronary thrombosis, myocardial infarction), peripheral artery disease, stroke.

In one embodiment the term "preventing a cardiovascular disorder" may mean that one or more of the cardiovascular risk factors (as defined below) are treated and/or prevented and/or reduced in a subject administered with the high glucosinolate Cruciferous vegetable (such as the high glucosinolate broccoli), i.e. compared with a subject(s) which have not been administered with the high glucosinolate Cruciferous vegetable (such as the high glucosinolate broccoli) in accordance with the present invention.

Cardiovascular Risk Factors

The list below defines what are generally considered to be cardiovascular risk factors, i.e. factors that singularly or collectively put a person at risk of developing CVD or having a cardiovascular (CV) event.

| | | |
|---|---|---|
| Age | The chart is based on ages 49-69 years; this results in a slight under estimation of risk in those under over 70 | |
| Sex | Male and females have different levels of risk | |
| Systolic Blood Pressure | ≥140 mmHg* | ≥160 mmHg ** |
| Diastolic Blood Pressure | ≥90 mmHg* | ≥100 mmHg ** |
| Total Cholesterol | >240 mg/dL (6.2 mmol/L) ** | |
| HDL Cholesterol | <140 mg/dL men (1.0 mmol/L)* | <50 mg/dL women (1.2 mmol/L)* |
| Smoking Status | Tobacco exposure must be considered | |
| Glucose | ≥6.1 mmol/L-<7 mmol/L (=impaired fasting glucose)* | |
| Left Ventricular Hypertrophy (LVH) | Definite LVH on ECG (this will not be checked in our volunteers). | |
| Central obesity | Caucasians: male ≥102 cm* female: ≥88 cm* Asians: male ≥90 cm* female: ≥80 cm* | |
| South Asian origin | If yes, risk increased by a factor of 1.5 | |
| Family history of CVD | If there is a significant family history, risk increased by factor of 1.5 | |
| Serum Triglycerides | ≥1.7 mmol/L* | |

*Volunteer has a probability falling into the 10-20% risk group
** Volunteer has a probability of falling into the >20% risk group The cardiovascular risk factors form the integral parameters in the cardiac risk assessor, e.g an algorithm that calculates a persons risk of developing CVD from a set of biological and physiological values obtained from them [58].

A suitable cardiovascular risk calculator is also in a special edition of Heart (see "JBS2: Joint British Societies' Guidelines on Prevention of Cardiovascular Disease in Clinical Practice"—prepared by British Cardiac Society, British Hypertension Society, Diabetes UK, HEART UK, Primary Care Cardiovascular Society, The Stroke Association (Heart 2005, Vol 91: v1-v52; doi 10.1136/hrt.2005.079988 (Special Edition))—incorporated herein by reference. The algorithm used in JBS2 and further details with regard to the cardiovascular risk assessor can be found in Anderson et al Circulation 1991; 83: 356-62—incorporated herein by reference.

FIGS. 2a and 2b herein show cardiovascular risk prediction charts which can be used instead of or in conjunction with the risk assessor taught above. These charts are described in a special edition of Heart (see "JBS2: Joint British. Societies' Guidelines on Prevention of Cardiovascular Disease in Clinical Practice"—prepared by British Cardiac Society, British Hypertension Society, Diabetes UK, HEART UK, Primary Care Cardiovascular Society, The Stroke Association (Heart 2005, Vol 91: v1-v52; doi 10.1136/hrt.2005.079988 (Special Edition)). These charts are for estimating cardiovascular disease (CVD) risk (non-fatal myocardial infarction and stroke, coronary and stroke death and new angina pectoris) for individuals who have not already developed coronary heart disease (CHD) or other major atherosclerotic disease.

To estimate an individual's total 10 year risk of developing CVD using the cardiovascular risk prediction charts shown in FIGS. 2a and 2b the table for the subject's sex is chosen, as well as lifetime smoking status, and age. Within this square the level or risk is defined according to the point where the coordinates for systolic blood pressure and the ratio of total cholesterol to HDL-cholesterol meet. If no HDL cholesterol result is available, then assume this is 1.0 mmol/l and the lipid scale can be used for total cholesterol alone.

Higher risk individuals are defined at those whose 10 year CVD risk exceeds 20% which is approximately equivalent to a CHD risk of >15% over the same period. The chart also assists in the identification of individuals whose 10 year CVD risk is moderately increased in the range 10-20% and those in whom risk is lower than 10% over 10 years. The initial blood pressure and the first random (non fasting) total cholesterol and HDL cholesterol can be used to estimate an individual risk.

Alternative cardiovascular risk calculators are known to persons skilled in the art. By way of example only QRISK is a cardiovascular disease risk score specifically designed for the UK population and ASSIGN is designed for a Scottish population (see for example Hippisley-Cox et al BMJ (doi: 10.1136/bmj.39261.471806.55) pp1-12—which reference is incorporated herein by reference). Other suitable cardiovascular risk calculators would be known to one skilled in the art.

The cardiovascular risk factors which may be modified by the administration of a high glucosinolate Cruciferous vegetable (such as a high glucosinolate broccoli) are selected from one or more of the group consisting of:
  systolic blood pressure,
  diastolic blood pressure,
  total cholesterol,
  LDL cholesterol,
  arterial stiffness,
  inflammation,
  level of IL6,
  level of C-reactive protein (CRP).

Inflammation and elevated levels of IL6 and CRP play a role in increasing CVD risk. In one embodiment inflammation can be assessed by measuring IL6 and/or CRP levels.

In one embodiment of the present invention the use of a high glucosinolate Cruciferous vegetable may reduce levels of inflammation and/or inflammation markers and/or IL6 and/or CRP.

Arterial stiffness has been established as an independent predictor of CVD. Arterial stiffness can be determined by measuring pulse-wave velocity (PWV) or Augmentation index (AIx). In addition, augmentation index (AIx) has been shown to be a strong independent risk marker for coronary artery disease and pulse-wave velocity (PWV) has been shown to be an independent predictor of morbidity and mortality in hypertensive patients.

In one embodiment of the present invention the use of a high glucosinolate Cruciferous vegetable may reduce arterial stiffness and/or PWV measurements and/or AIx measurements.

In one embodiment preferably one or more of systolic blood pressure, diastolic blood pressure, LDL-cholesterol (i.e. total cholesterol minus HDL-cholesterol and minus serum triglycerides), or total cholesterol is/are reduced in subjects treated with a high glucosinolate Cruciferous vegetable (such as a high glucosinolate broccoli), compared with control subjects.

Suitably, administering a high glucosinolate Cruciferous vegetable (such as a high glucosinolate broccoli) may reduce systolic blood pressure in the treated subject, suitably the systolic blood pressure may be reduced to <160 mmHg, preferably to <140 mmHg.

Suitably, administering a high glucosinolate Cruciferous vegetable (such as a high glucosinolate broccoli) may reduce systolic blood pressure in the treated subject by about 1-20 mmHg, suitably by about 2-10, suitably by about 4-10 mmHg, suitably by about 4-6 mmHg. Suitably, administering a high glucosinolate Cruciferous vegetable (such as a high glucosinolate broccoli) may reduce systolic blood pressure in the treated subject by at least about 3 mmHg, suitably by at least about 4 mmHg, suitably by at least about 5 mmHg, suitably by about 6 mmHg, suitably by about 10 mmHg.

Suitably, administering a high glucosinolate Cruciferous vegetable (such as a high glucosinolate broccoli) may reduce diastolic blood pressure in the treated subject, suitably the diastolic blood pressure may be reduced to <100 mmHg, preferably to <90 mmHg.

Suitably, administering a high glucosinolate Cruciferous vegetable (such as a high glucosinolate broccoli) may reduce diastolic blood pressure in the treated subject by about 1-20 mmHg, suitably by about 2-10, suitably by about 3-10 mmHg, suitably by about 3-5 mmHg. Suitably, administering a high glucosinolate Cruciferous vegetable (such as a high glucosinolate broccoli) may reduce diastolic blood pressure in the treated subject by at least about 2 mmHg, 3 mmHg, suitably by at least about 4 mmHg, suitably by at least about 5 mmHg, suitably by about 6 mmHg, suitably by about 10 mmHg.

Suitably, administering a high glucosinolate Cruciferous vegetable (such as a high glucosinolate broccoli) may reduce total cholesterol in the treated subject, suitably the total cholesterol may be reduced to <240 mg/dL (6.2 mmol/L).

Suitably, administering a high glucosinolate Cruciferous vegetable (such as a high glucosinolate broccoli) may reduce total cholesterol in the treated subject by about 0.2-3.0, suitably by about 0.3-1.0, suitably by about 0.3-0.6 mmol/L, suitably by about 0.4-0.5 mmol/L. Suitably, administering a high glucosinolate Cruciferous vegetable (such as a high glucosinolate broccoli) may reduce total cholesterol in the treated subject by at least about 0.2, such as by at least about 0.3, such as by at least about 0.4, such as by at least about 0.5 mmol/L.

Suitably, administering a high glucosinolate Cruciferous vegetable (such as a high glucosinolate broccoli) may reduce LDL-cholesterol in the treated subject, suitably the LDL-cholesterol may be reduced to <3.5 mmol/L (for men) or to <3.3 mmol/L (for women).

Suitably, administering a high glucosinolate Cruciferous vegetable (such as a high glucosinolate broccoli) may reduce LDL-cholesterol in the treated subject by about 0.1-1.0 mmol/L, suitably by about 0.2-0.7 mmol/L, suitably by about 0.2-0.5 mmol/L, suitably by about 0.3-0.4 mmol/L. Suitably administering a high glucosinolate Cruciferous vegetable (such as a high glucosinolate broccoli) may reduce LDL-cholesterol in the treated subject by at least about 0.2 mmol/L, suitably by at least about 0.3 mmol/L, suitably by at least about 0.4 mmol/L, suitably by at least about 0.5 mmol/L.

In one embodiment, the present invention relates to a composition comprising a high glucosinolate Cruciferous vegetable (such as a high glucosinolate broccoli) and/or at least one derivative thereof for use in reducing one or more of the cardiovascular risk factors.

In another embodiment, the present invention relates to a composition comprising a high glucosinolate Cruciferous vegetable (such as a high glucosinolate broccoli) and/or at least one derivative thereof for use in reducing the risk of developing cardiovascular disease.

In one aspect of the present invention the use of high glucosinoalte Cruciferous vegetable in accordance with the present invention (such as high glucosinolate broccoli) leads to a overall reduction in CVD risk (i.e. the risk of developing cardiovascular disease) by moderating (usually reducing) the individual risk factors (such as LDL-cholesterol level, total cholesterol level, systolic blood pressure, and/or diastolic blood pressure) used in the assessment of CVD risk.

In yet another embodiment, the present invention relates to a composition comprising a high glucosinolate Cruciferous vegetable (such as a high glucosinolate broccoli) and/or at least one derivative thereof for use in the treatment or prevention of one or more of the following group consisting of: hypertension, hypercholesterolemia or hyperlipidemia.

Hyperlipidemia

Hyperlipidemia is the condition of abnormally elevated levels of any or all lipids and/or lipoproteins in the blood.

Lipids (fat-soluble molecules) are transported in a protein capsule, and the size of that capsule, or lipoprotein, determines its density. The lipoprotein density and type of apolipoproteins it contains determines the fate of the particle and its influence on metabolism.

Lipid and lipoprotein abnormalities are common in the general population, and are regarded as a modifiable risk factor for cardiovascular disease due to their influence on atherosclerosis.

Hypercholesterolaemia

Hypercholesterolaemia (literally: high blood cholesterol) is the presence of high levels of cholesterol in the blood. It is a metabolic derangement that can contribute to cardiovascular disease. It is closely related to the terms "hyperlipidemia" (elevated levels of lipids in the blood).

Hypertension/High Blood Pressure

Hypertension or high blood pressure is a chronic medical condition in which the systemic arterial blood pressure is elevated. It is the opposite of hypotension. It is classified as either primary (essential) or secondary.

Persistent hypertension is one of the risk factors for cardiovascular diseases, including stroke, myocardial infarction, heart failure and arterial aneurysm.

The invention will now be described, by way of example only, with reference to the following Figures and Examples.

FIGURES

FIG. 2 shows the Joint British Societies CVD risk prediction chart for non diabetic men.

Figure 4:
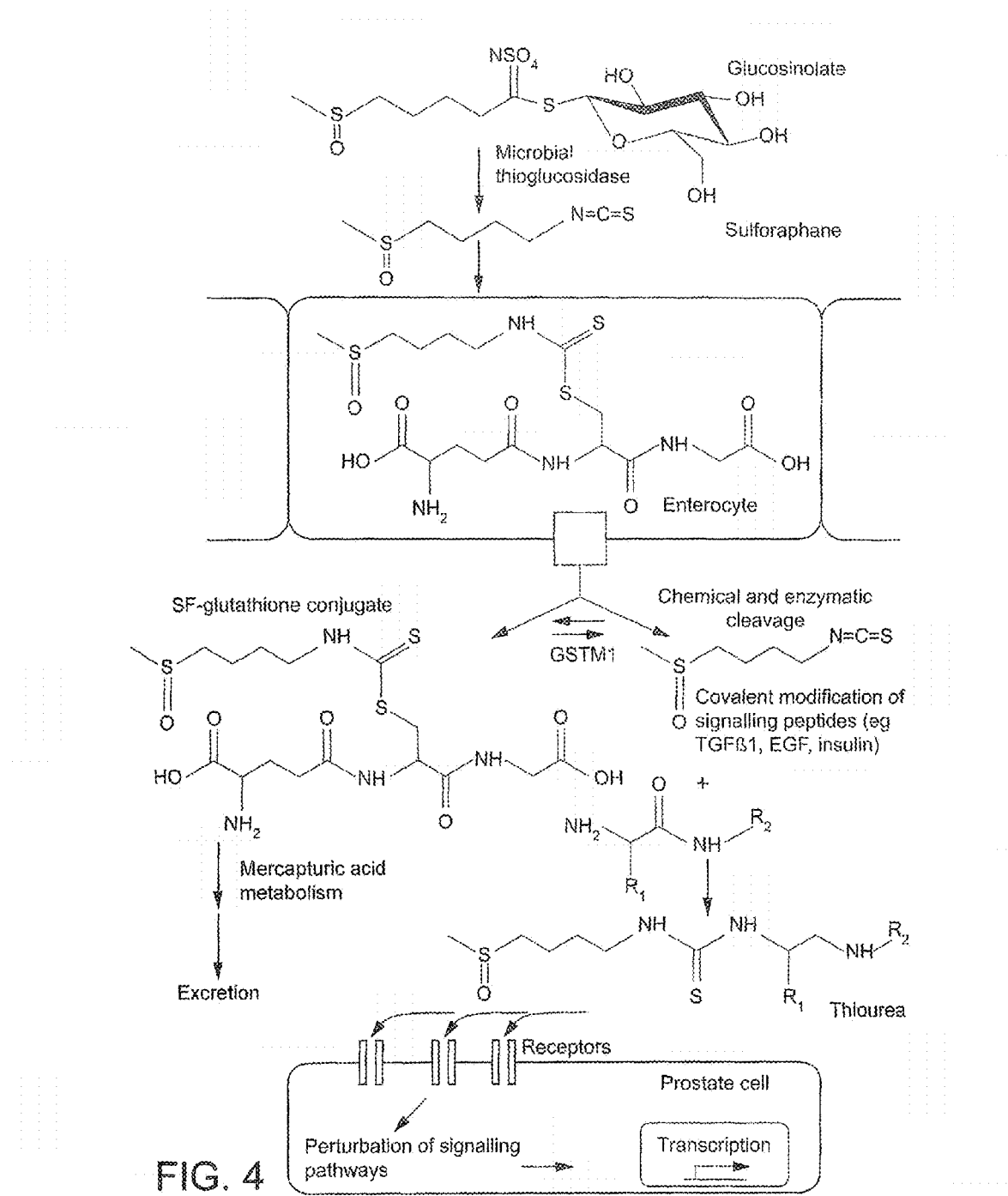

FIG. 4 shows the metabolism of 4-methylsulphinylbutyl glucosinolate and sulforaphane. Upon entry into enterocytes sulforaphane (SF) is rapidly conjugated to glutathione, exported into the systemic circulation and metabolized through the mercapturic acid pathway. Within the low glutathione environment of the plasma the SF-glutathione conjugate may be cleaved, possibly mediated by GSM1, leading to circulation of free SF in the plasma. This free SF can modify plasma proteins including signalling molecules, such as TGFβ, EGF and insulin.

Figure 5:
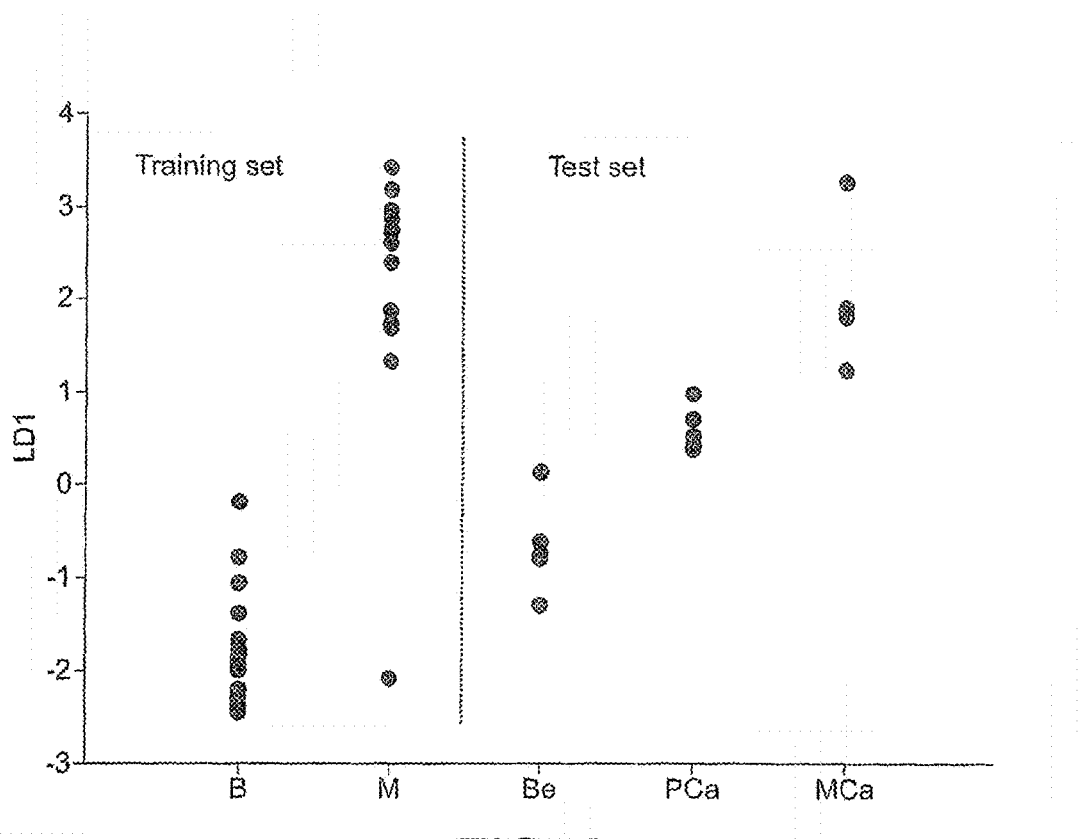

FIG. 5 shows LDA of an independent prostate microarray data set.

Linear discriminant analysis (LDA) using the benign (B) and malignant (M) (transurethral resection of the prostate) TURP prostate tissue for this study as training samples to classify the laser-capture microdissected (LCD) epithelial prostate cell samples (GEO Accession:GDS1439), consisting of benign (Be), primary cancer (PCa) and metastatic cancer (MCa) samples. LDA was performed on a gene list that distinguished the benign and malignant TURP samples as described in Methods. Here, the first linear discriminant (LD1) is shown.

Figure 6:
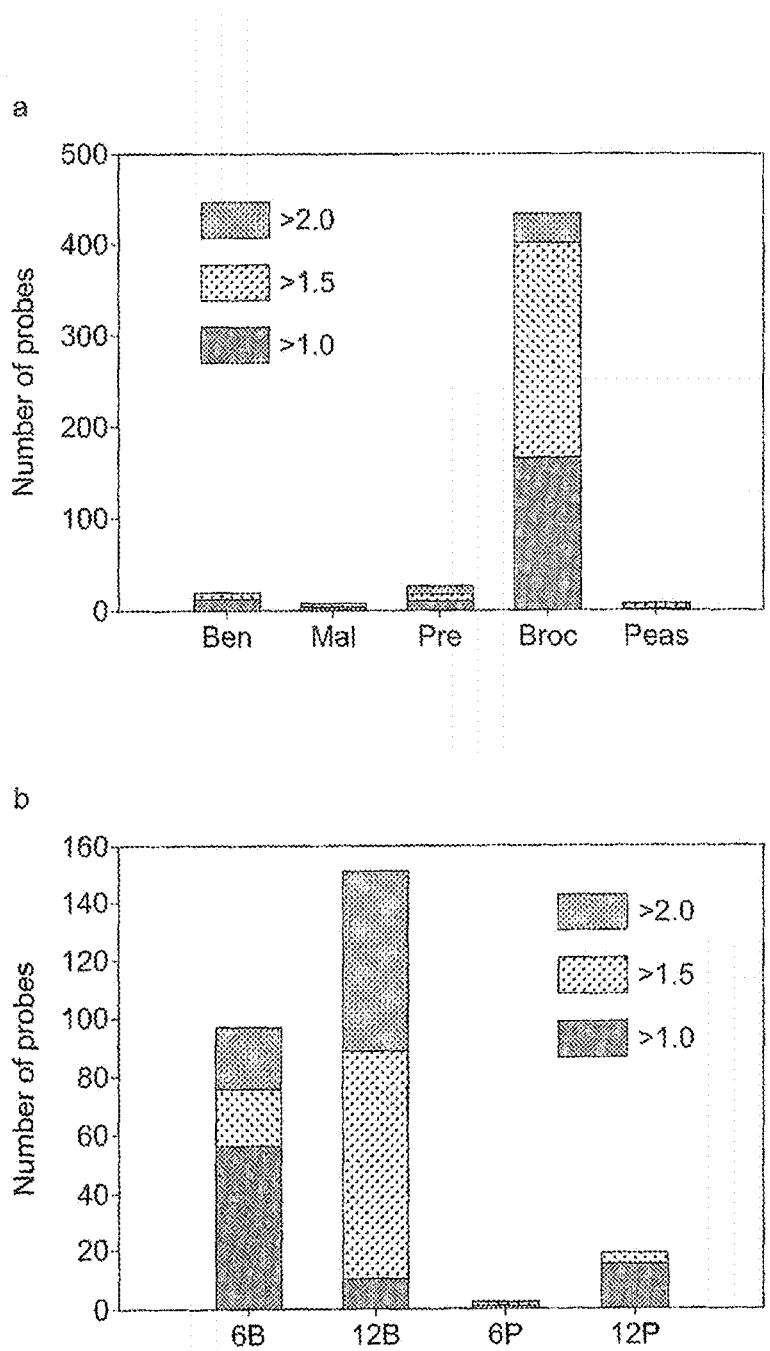

FIG. 6 shows the effect of dietary intervention on gene transcription.

a, Number of probes that differ between GSTM1 positive and null genotypes ($P \leq 0.005$, Welch modified two-sample t-test) in TURP tissue from benign (Ben) and malignant (Mal) prostates, and transrectal ultrasound-guided (TRUS-guided) biopsy tissue from volunteers at pre-intervention (Pre), post 6 months broccoli-rich diet (Broc) and post 6 months pea-rich diet (Peas). b, Number of probes that differ between pre-intervention TRUS-guided biopsy samples and after 6 months broccoli (6B)-, 6 month pea (6P)-, 12 month broccoli (12B)- and 12 month pea (12 P)-rich diets ($P \leq 0.005$, Welch modified two-sample paired t-test). Shading corresponds to different fold cutoffs applied. See Table 2 for full details of probe numbers, P-values and median false discovery rates.

Figure 7:
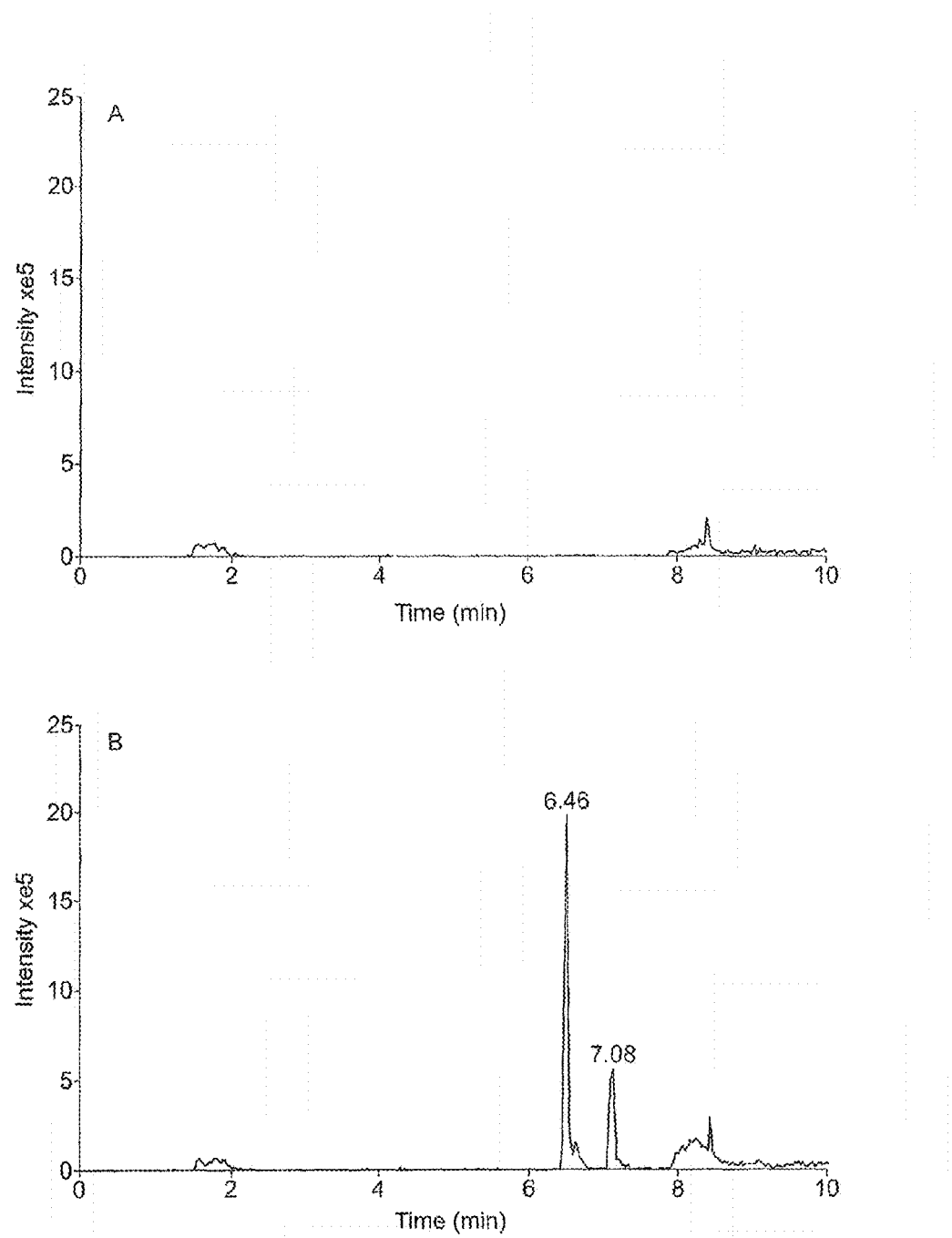

FIG. 7 shows Liquid Chromatography-Mass Spectrometry (LC-MS) of insulin incubated with and without SF in human plasma.

Extracted ion LC-MS chromatograms (m/z 1183.6-1184.1) of insulin-SF $MH_5^{5+}$ in (A) unmodified insulin (20 μg/ml) in human plasma control and (B) human plasma incubated with insulin (20 μg/ml) and 50 μM SF for 4 h at 37° C., showing the appearance of two different insulin-SF conjugates at retention times of 6.46 and 7.08 min. The enhanced product ion (EPI)-MS spectra of these two insulin-SF conjugates are shown in FIG. 8.

Figure 8:
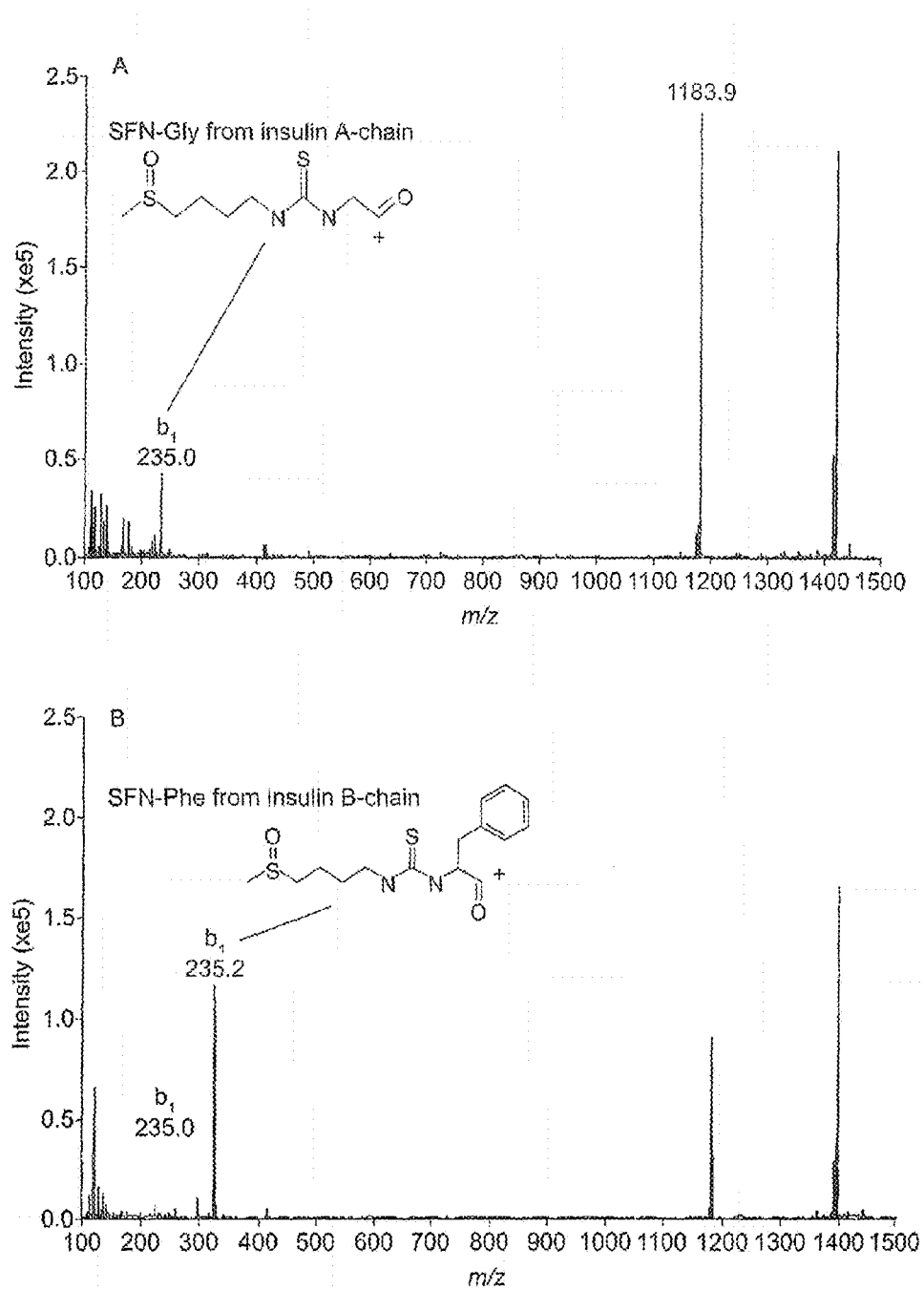

FIG. 8 shows enhanced product ion (EPI)-MS spectra of the two insulin-SF conjugates. $MS^2$ product ion spectra of (A) 6.46 min and (B) 7.08 min retention time peaks from LC-MS analysis of human plasma incubated with bovine insulin and 50 μM SF for 4 h at 37° C. In (A) and (B) m/z 1183.9 corresponds to insulin-SF $MH_5^{5+}$ and in (A) m/z 235.0 corresponds to Gly-SF, the N-terminal amino acid of insulin A chain and in (B) m/z 325.2 corresponds to Phe-SF, the N-terminal amino acid of insulin B chain.

Figure 9:
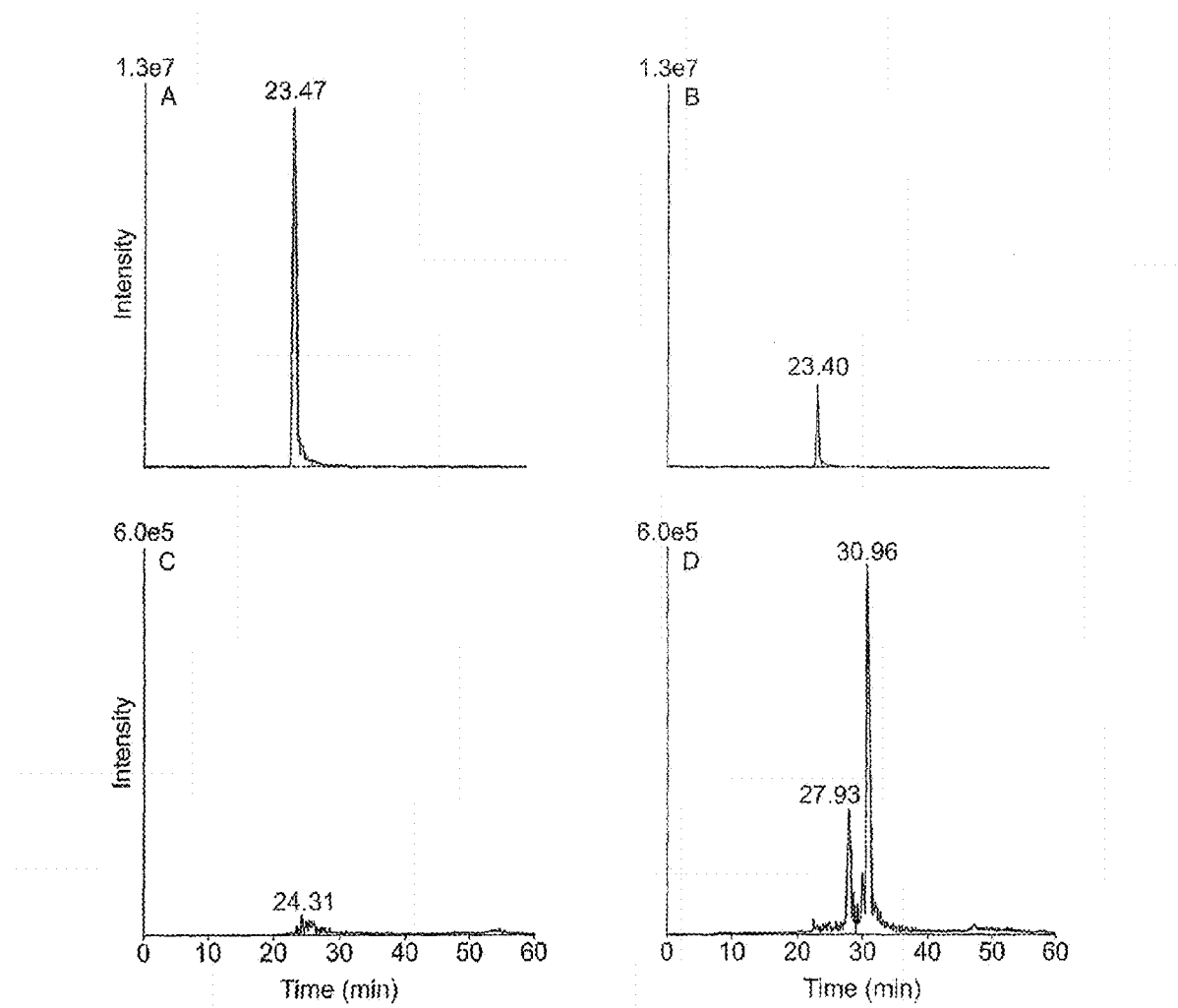

FIG. 9 shows LC-MS of TGFβ1 incubated with and without SF.

Extracted ion chromatograms (MS) of precursor masses representing the unmodified N-terminal peptide of TGFβ1 (m/z 768.5) and the modified N-terminal peptide (m/z 877.2) A of m/z 768.2-769.2 from DMSO treated TGFβ1, B of m/z 768.2-769.2 from SF treated TGFβ1, C of m/z 876.7-877.7 DMSO treated TGFβ1 and D of m/z 876.7-877.7 SF treated TGFβ1.

Figure 10:
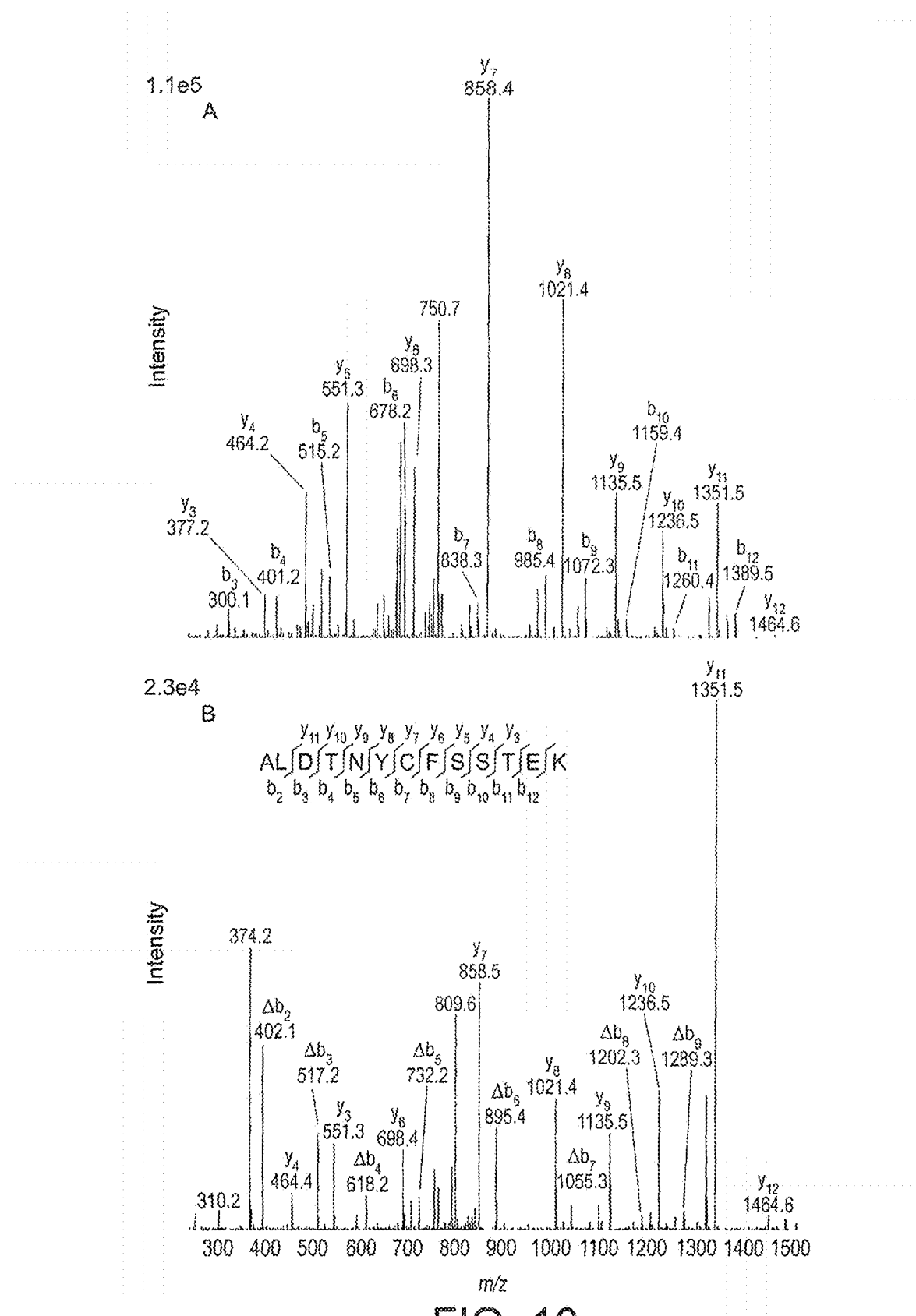

FIG. 10 shows N-terminal modification of TGFβ1 by SF. MS/MS spectra of m/z 768.7 representing the unmodified N-terminal peptide of TGFβ1 at retention time 23.43 min (A) and m/z 877.2 representing a modified form of TGFβ1 seen only in SF treated samples at retention time 30.85 minutes (N). Note that the y ion series remains the same while the b ion series shifts (Δ) indicating an N-terminal modification of mass 217±0.8 Da.

Figure 11:
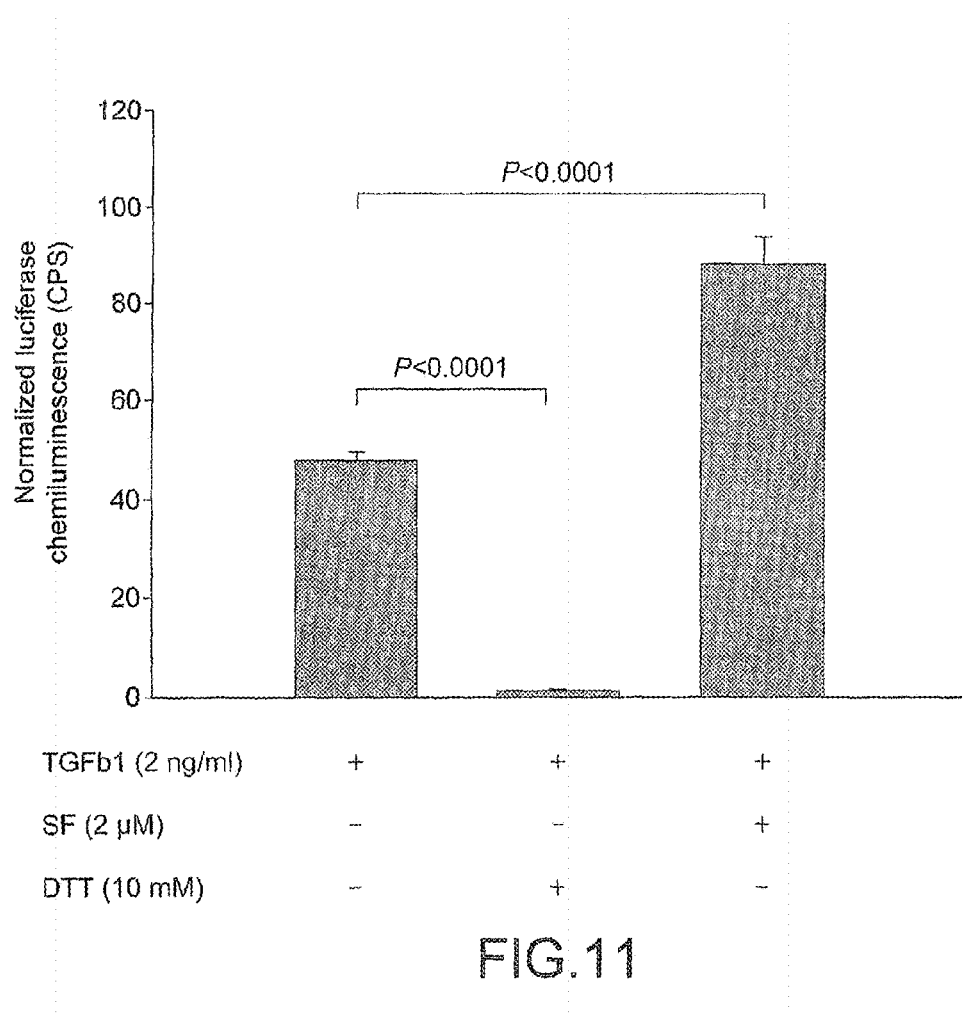

FIG. 11 shows activation of TGFβ1/Smad mediated transcription by SF.

NIH3T3 cells containing a CAGA12-luc plasmid were treated with TGFβ1 alone, TGFβ1 and 10 mM DTT, which disrupts the active TGFβ1 dimer, or TGFβ1 and 2 μM SF. All samples were pre-incubated for 30 minutes and further dialyzed for 4 h so that the final concentration of SF was 34 nM.

As an additional negative control cells received no treatment or only 34 nM SF, both of which failed to induce luciferase. Chemiluminescence was normalized to the protein concentration of each sample (for details see Methods). This is a representative experiment of a total of four similar experiments performed. Data shown are mean (s.e.m) of three replicates.

Figure 12:
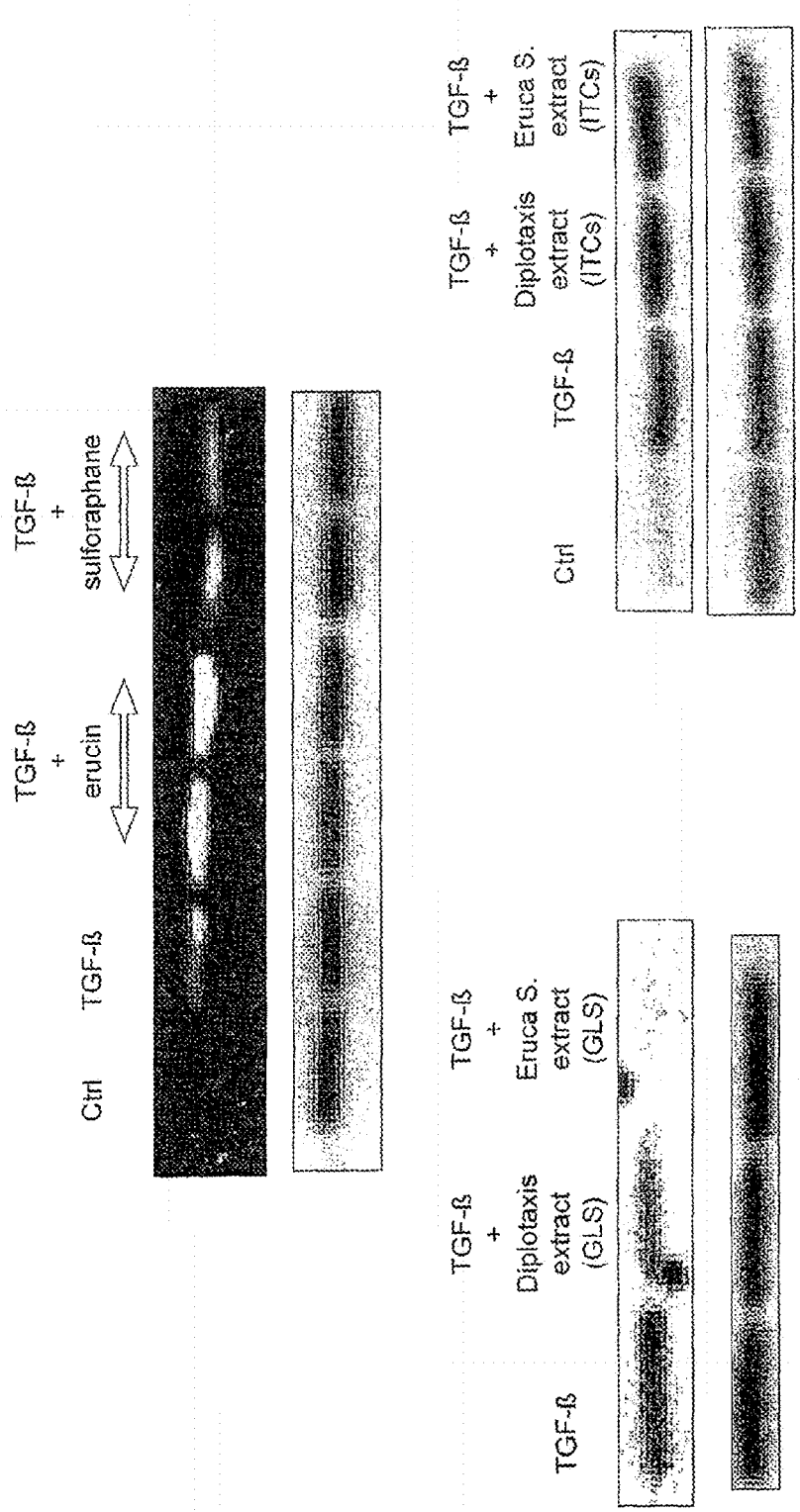

FIG. 12 shows the effect of pure compound and total extracts from rocket on TGF-β signalling pathway in adenocarcinoma epithelial A549 cells.
Extracts from rocket that have been heat treated so that no isothiocyanates are produced show a suppression of TGF beta signalling. Erucin seems more efficient at up regulating TGF beta signalling than SF.

FIG. 13 shows a western blot analysis of Caco-2 cells for phosphorylated SMAD2 after treatment with broccoli extracts and/or TGFβ1. Panel A phosphorylated SMAD2; Panel B GAPDH. Lanes 1, 2—control; 3, 4 TGFβ1; 5, 6—0 min; 7, 8—4 min; 9—1 min; 10—1 min+TGF β (2 μg/L).

FIG. 14 shows the primers and probes which were designed using Applied Biosystems Primer Express (Applied Biosystems) together with PCR conditions for use with real-time PCR procedure based on Covault and colleagues for genotype analysis [21].

Figure 15:
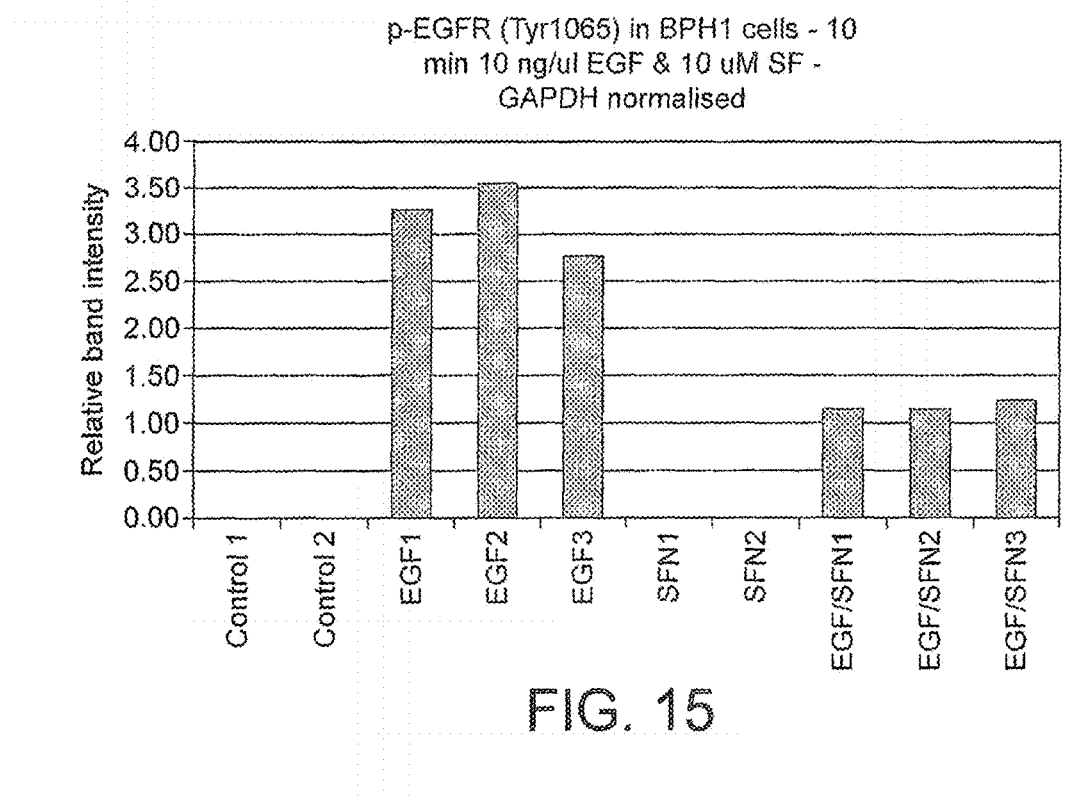

FIG. 15 shows the functional consequences of interactions between ITCs and signalling peptides, showing that incubation of ITCs with EGF can suppress EGF signalling in BPH cells, a model of hyperplastic prostatic tissue. Data presented shows that pre-incubation of EGF with 4-methylsulphinylbutyl ITC (SF) under conditions known to cause peptide modification reduces the amount of phosphorylated receptor compared to EGF alone. This would be expected to result in inhibition of the EGF signalling pathway, with anti-inflammatory consequences.

Figure 17:
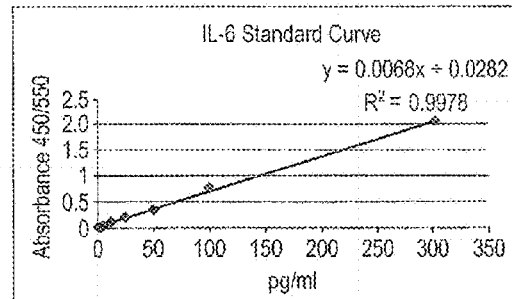

FIGS. 16 & 17 Procyanidins (at a dose of 2 μM) can inhibit tumor nectrosis factor-alpha (TNF-alpha) induced IL-6 in HUVEC cell model; the procyanidin was obtained from a grape skin extract (GE).

Figure 18:
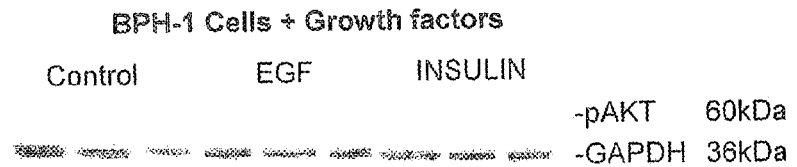

FIG. 18 shows a benign prostate hyperplasia cell (BPH-1) (which is not a cancer cell) which shows that when the growth factors EGF and insulin are added the level of pAKT increases.

Figure 19:
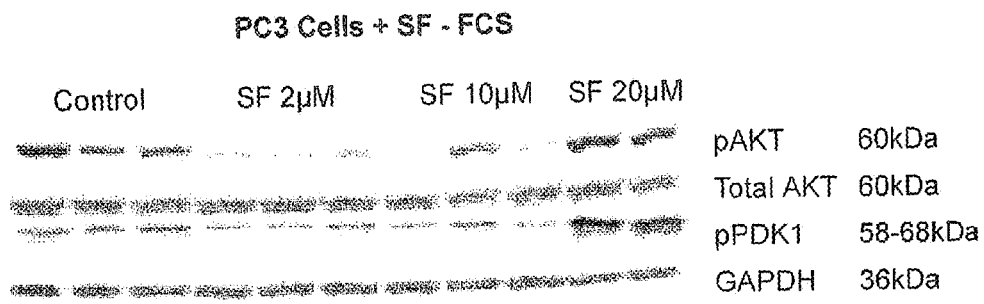

FIG. 19 shows a cancer cell PC3 cultured in fetal calf serum (FCS) and treated with the ITC, SF. As can be seen from the results in the control a lot of pAKT is present. When treated with 2 μM levels of a significant reduction in pAKT was observed. The SF was acting through extracellular signaling proteins (such as insulin) in the fetal calf serum.

Figure 20:
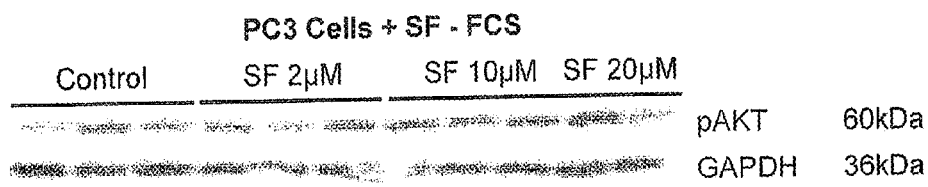

FIG. 20 shows that the results in FIG. 19 were due to the extracellular signaling proteins in the FCS. In FIG. 20 results are shown without FCS. As can be seen without FCS SF did not function to reduce pAKT.

Figure 21:
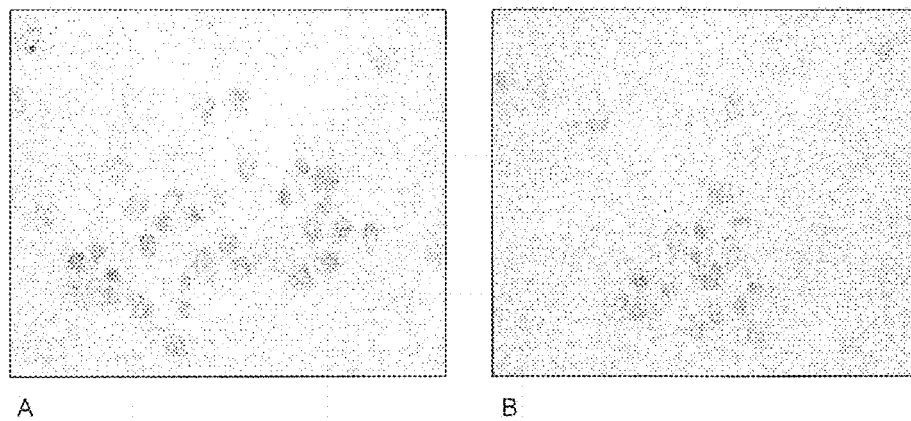

FIG. 21 shows the results of the western blot. A: Immunohistochemistry of PC-3 cells showing pAKT expression (red colouration). B: Immunohistochemistry of PC-3 cells following incubation in 2 μM SF for 1 h showing inhibition of pAKT expression (no red colouration).

EXAMPLES

Study Design

Figure 1:
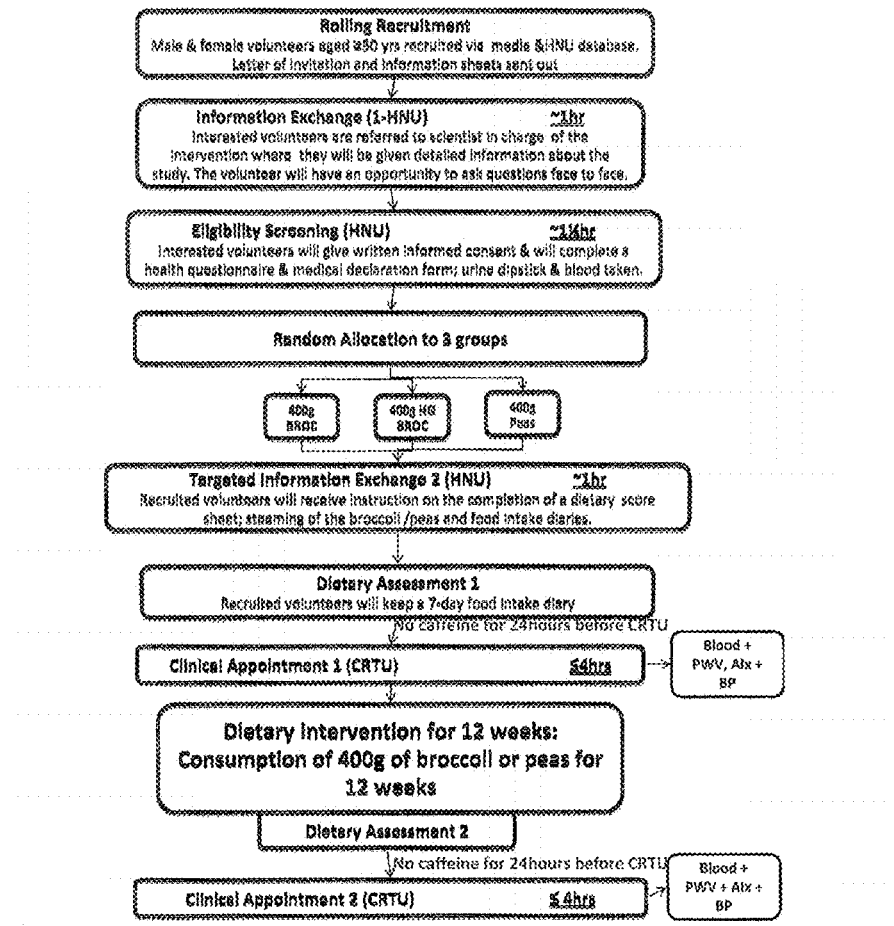
FIG. 1 shows an outline of the study undertaken to determine the effect of administration of glucosinolates on risk factors associated with CVD.

The study is a randomised parallel study with smoking and non smoking men and women over the age of 50 deemed to have a mild to moderate risk of developing CVD or having a CV event. This mild to moderate risk is defined as a 10-20% chance of developing CVD in the next 10 years and can be calculated by the Joint British Societies (JBS 2) CVD risk assessment charts [58] (FIG. 2), which are based on the Framingham Risk Score [59]. The volunteers are matched for gender while being assigned to one of 3 study groups. One group consumes 400 g of standard broccoli each week for 12 weeks; the second group consumes 400 g of the high glucosinolate broccoli each week for 12 weeks while the third group consumes 400 g of peas each week for 12 weeks. The broccoli and the peas are consumed on top of the volunteer's standard diet. In order to assess the habitual diet of the volunteers, they are asked to keep two 7-day diet diaries, one pre intervention and the other towards the end of their intervention. A number of physiological tests are performed on the volunteers pre and post intervention (baseline—week 0 and at week 12); blood samples are taken to determine their lipid profile as well as a number of CVD risk indicators. The study outline is shown in FIG. 1.

The study population consists of three groups of smoking and non smoking men and women aged 50 years old and above (n=22 per broccoli group; n=10 for control pea group) who have a mild to moderate risk of developing CVD or having a CV event (defined in the inclusion criteria below) over the next 10 years. Equal numbers of men and women, smokers and non smokers are recruited. Each group of volunteers also has an even distribution of numbers with GSTM1 deletion (as they make up approximately half the population, this is achieved by using covariate adaptive randomisation technique [60].

The volunteers are matched by gender, smoking status and genotype (the first 10 volunteers are randomly assigned to the one of the three groups). The diet diary is used to define high (>3 portions per week) or low (<1 portion a week) habitual consumers of cruciferous vegetables. Volunteers are then randomly assigned to one of three dietary intervention groups:
1. The standard broccoli group is asked to consume an additional 4 portions (100 g each) of standard broccoli per week as part of their normal diet.
2. The 'HG' broccoli group is asked to consume an additional 4 portions (100 g each) of a special variety of broccoli, selectively grown for its enhanced glucosinolate content, per week as part of their normal diet.
3. The pea control group is asked to consume an additional 4 portions (100 g each) of Birds Eye® peas per week as part of their normal diet.

Volunteers are asked to modify their habitual diets for a total of 12 weeks by eating the standard broccoli, the HG broccoli or the peas. This is to enable us to detect any changes in the biochemical markers of CVD risk, particularly total cholesterol concentration, LDL-cholesterol and blood pressure. Volunteers can choose which day to eat the vegetables, but are asked to keep a record of when the vegetables are eaten.

Cardiovascular Risk Factors

The volunteers recruited had a mild to moderate risk of developing CVD or of having a CV event in the next 10 years [61-63]. The list below defines what are generally considered to be cardiovascular risk factors, i.e. factors that singularly or collectively put a person at risk of developing CVD or having a CV event. The parameters below are used to assess the suitability of the volunteers for the study. They form the integral parameters in the cardiac risk assessor, an algorithm that calculates a person's risk of developing CVD from a set of biological and physiological values obtained from them [58]. The cardiovascular risk assessor is taught in a special edition of Heart (see "JBS2: Joint British Societies' Guidelines on Prevention of Cardiovascular Disease in Clinical Practice"—prepared by British Cardiac Society, British Hypertension Society, Diabetes UK, HEART UK, Primary Care Cardiovascular Society, The Stroke Association (Heart 2005, Vol 91: v1-v52; doi 10.1136/hrt.2005.079988 (Special Edition)).

| | |
|---|---|
| Age | The chart is based on ages 49-69 years; this results in a slight under estimation of risk in those under over 70 |
| Sex | Male and females have different levels of risk |
| Systolic Blood Pressure | ≥140 mmHg* ≥160 mmHg ** |
| Diastolic Blood Pressure | ≥90 mmHg* ≥100 mmHg ** |
| Total Cholesterol | >240 mg/dL (6.2 mmol/L) ** |
| HDL Cholesterol | >40 mg/dL men <50 mg/dL women (1.0 mmol/L)* (1.2 mmol/L)* |
| Smoking Status | Tobacco exposure must be considered |
| Glucose | ≥6.1 mmol/L-<7 mmol/L (=impaired fasting glucose)* |
| Left Ventricular Hypertrophy (LVH) | Definite LVH on ECG (this will not be checked in our volunteers). |
| Central obesity | Caucasians: male ≥102 cm* female: ≥88 cm* Asians: male ≥90 cm* female: ≥80 cm* |
| South Asian origin | If yes, risk increased by a factor of 1.5 |
| Family history of CVD | If there is a significant family history, risk increased by factor of 1.5 |
| Serum Triglycerides | ≥1.7 mmol/L* |

*Volunteer has a probability falling into the 10-20% risk group
** Volunteer has a probability of falling into the >20% risk group The volunteers fall within this mild to moderate group without their participation in the project compromising their health or without them taking any medication. The calculator is used once all the screening results are obtained. The power calculation (see statistics section) is based on total cholesterol concentration, including LDL-cholesterol (i.e. total cholesterol minus high density lipoprotein-cholesterol (HDL-cholesterol) and minus serum triglycerides (TG)) and/or blood pressure values. Although the UK national average is 5.7 mmol/L [65] volunteers are recruited with a cholesterol value of at least ≥5 mmol/L as standards set out by the JBS 2 suggest treating people with values as low as ≤4 mmol/L [58]. There is no evidence to suggest that dietary changes will not be seen in values less than 5.7 mmol/L. In the study looking at the consumption of broccoli sprouts, the baseline cholesterol values of the participants are 4.5 mmol/L and 4.6 mmol/L, for men and women respectively and a decrease in total cholesterol is still seen [32].

According to the British Hypertensive Society (BHS), the systolic and diastolic blood pressures mentioned above are classed as mildly hypertensive [66]. Data from past studies examining the age group to be recruited (≥50 years), show that volunteers with blood pressures in this higher range may be difficult to recruit and so the value for our recruitment purposes is lowered to optimal blood pressure, 120/80 mmHg and above, as defined by the BHS.

Smoking status is an important issue associated with CVD risk and so the status of any volunteers reflects a lifetime's exposure to tobacco. For example a volunteer who has smoked five cigarettes a day for 8 years, will probably have lower tobacco exposure than someone who smoked 40 cigarettes a day for 20 years until 3 years ago. The inclusion and exclusion criteria have been set accordingly.

The Cardiac Risk Assessor Calculator.

FIGS. 2a and 2b demonstrate the JBS 2 CVD risk prediction chart for non diabetic men and women respectively. It is our aim to recruit volunteers that fall into the 10-20% risk of developing CVD over the next 10 years, which equates to their systolic BP and TC: HDL values falling within the range designated by the paler lower section of the charts. People who generally fall into the >20% range would usually be recommended for some form of therapy more drastic than life style and diet changes, antihypertensive, lipid lowering, glucose lowering and other cardiovascular protective therapies in order to reduce overall CV risk by their GPs.

Inclusion Criteria

Men and women aged ≥50 years were recruited onto the study: Scores of 10-20% will be acceptable for participation in the study.
Total cholesterol ≥5.0 mmol/L
Blood pressure measurements,
  systolic≥120 mmHg;
  diastolic ≥80 mmHg
BMI ≥20
Smokers and Non Smokers Exclusion Criteria Diagnosed diabetics;
Fasting glucose >6 mmol/L;
Blood pressure <90/50 or 95/55 if symptomatic; >160/100
Chronic kidney disease;
Those on any lipid lowering therapies like statins, bile acid sequestrants, cholesterol absorption inhibitors and nicotinic acid;
Those who have suffered a cardiovascular event like stroke, myocardial infarction or trans ischemic attacks;
Peripheral vascular disease including Claudication
Consumption of fish oil supplements (unless volunteer is willing to discontinue their use 4 weeks prior to the start of the trial)
Parallel participation in another research project which involves dietary intervention and/or sampling of biological fluids/materials
Any person related or living with any member of the study team
Participation in another research project which involves blood sampling within the last four months; Blood from both studies should not exceed 470 mL
BMI <20
BMI >40
Fasting total cholesterol >8.0 mmol/L
Gastrointestinal disease (excluding hiatus hernia) unless symptomatic or study intervention/procedure is contraindicated
Going on holiday for more than 7 days in any single period or within 2 weeks of their clinical appointment at the CRTU
Currently suffering from or have suffered from any neck and throat injuries and surgery Information Exchange (1)—Human Nutrition Unit (HNU)—Visit 1 for Volunteer.

After receiving details of the study all volunteers are given a minimum of 72 hours (3 days) to consider whether they wish to participate in the study. Those wishing to participate following this period of consideration are invited to attend the HNU for an eligibility screening following an overnight fast of at least 8 hours. Volunteers are advised that they should drink as much water as they need during this fasting period. They are reminded to bring a midstream sample of urine from their first urine of the morning in the container provided at the first information exchange. The mid stream urine is not tested until after the consent form has been signed. Volunteers need to arrive within 2 hours of the urine sample being collected as this is a required specification for the validity of the urine dipstick test. Volunteers are also reminded to bring details of any prescribed medication, herbal remedies or dietary supplements (i.e. name of medication, dose taken etc).

Eligibility Screening—HNU—Visit 2 for Volunteer.

A HNU nurse completes a health questionnaire, measures and records blood pressure, pulse, height, weight and waist circumference, calculated body mass index (BMI), checks the urinalysis (Combur$^9$ $^{Test}$®, Roche Diagnostics Ltd) and a 19.5 mL of blood is taken for full blood count, full lipid profile, glucose, C-reactive protein, urea & electrolytes, albumin. A volume of 5 mL of the blood is then used for genotyping (GSTM1, GSTT1 and GSTP1.

If the BMI is <20 or >40 the volunteer is excluded from the study.

Volunteer Randomisation

Volunteers are randomised to a covariant adaptive method, also known as the minimisation method [60]. The main aim of this method is to minimise the differences between the treatment groups which is vital when carrying out studies with relatively small numbers of volunteers and treatment groups equalling or out numbering the covariants (age, gender, smoking status etc) as is the case in this study [67]. This method can be used after a small number of volunteers are randomly assigned to their treatment arms, then each new volunteer is sequentially assigned to a group taking into account the assignment of previous volunteers [60].

The results of the study relate to 24 volunteers in total; 10 in the HG broccoli group, 8 in the standard broccoli group and 7 in the pea group.

The volunteers are blinded as to which broccoli they will consume. The data produced is analysed by paired T-tests and/or 1-way ANCOVA as covered in section 19-Statistics.

Information Exchange (2)—HNU—Visit 3 for Volunteer.

Once recruited onto the study, volunteers are assigned a second code number.

Clinical Appointments 1 & 2—Clinical Research and Trials Unit (CRTU at UEA)—Visits 4 & 5 for Volunteer.

All measurements and samples are performed by nurses. The volunteer fast for at least 8 hours, and abstain from all caffeinated items for 24 hours prior to their clinical appointment. Volunteers who smoke abstain from having a cigarette for about an hour prior to all measurements being taken. The volunteer is taken to a quiet study bedroom in the CRTU, where the pre intervention (baseline, week 0) set of physiological measurements take place. The first task is to assess the volunteer's general health before proceeding to measurements. It is established whether any medication had been taken or changed since their last visit associated with the study (either screening or clinical appointment 1) and whether they have experienced any adverse events (AEs)/serious adverse events (SAEs) that they haven't already disclosed by phone, letter or e-mail. Once all the information is collected, if any, the nurse about to record the measurements assesses whether the volunteer is able to proceed. The nurse taking the information is responsible for completing the necessary paperwork associated with any AE or SAEs. If the volunteer is unable to proceed, depending on the nature of the information obtained, an alternative date was arranged, or the volunteer is excluded from the study.

Prior to the measurements being carried out, the volunteer's blood pressure is taken in both arms. The volunteer's height, weight, hip and waist measurements are also taken. These measurements are required for the pulse wave velocity measurement. The first procedure is blood sampling. A volume of 18 mL of blood is taken to measure the lipid profile; fasting glucose, CRP, FBC, albumin. On top of these samples, aliquots of blood are taken to produce serum and/or plasma for vitamin. D (vit D) analysis, IL6 and hs-CRP ELISAs. The volunteers have their ambulatory blood pressure (BP) measurements taken every 10 minutes. The volunteers wear the cuff for just over an hour which enables 6 BP readings to be obtained from which the mean BP is determined. This is repeated 12 weeks after the baseline value (post intervention—week 12).

The second measurement is the PWV using the Vicorder (Skidmore Medical Ltd). This is the first of two arterial stiffness measurements. For this procedure, the volunteers are asked to lie still and relax in a quiet, temperature regulated room for up to 30 minutes. After up to 30 minutes at rest, the volunteers BP at rest is taken after which, a cuff approximately one inch thick is placed around the neck with the inflatable section in contact with the carotid artery (only this small section inflates during the measurement and not the whole cuff) and around the upper thigh of one leg to measure the femoral artery (approximately 4 inches thick). The volunteer is discouraged from talking or sleeping while the measurements were being taken as this may interfere with the readings. Once the cuffs are attached, the nurse carried out four physical measurements, mid point of the carotid cuff to mid point of the femoral cuff (cm); upper sterna notch—mid point of femoral cuff (cm); upper sterna notch-lower sterna notch (cm) and lower sterna notch—mid point of femoral cuff (cm).

Three PWV readings are then be taken by the nurse.

The final procedure is measurement of the AIx using the SphygmoCor (Atcor MedicalPty Ltd) system of applanation tonometry. The volunteer remains lying down, or could be seated for this procedure. The volunteer's arm needs to be stable and to enable this, the arm is rested either on a table or bed, and the wrist is supported and slightly flexed (either with a small rolled-up towel or the nurse's hand). It is important that the volunteer's wrist is flat and not held at an angle.

This measurement is repeated three times to obtain three sets of data. This measurement like the others is repeated 12 weeks after baseline.

Compliance

Volunteers are asked to fill in a weekly vegetable record sheet during the 12 week intervention period, recording a tick each time they eat their vegetable portion each week. It is hoped that this will aid compliance during the dietary intervention. The vegetable record sheets is also used with the 7-day diet diary as a means of monitoring compliance.

Dietary Assessment

The habitual diet in all three groups is measured since the control group may consume high levels of cruciferous vegetables as part of their normal diet. This information is useful in order to explain any confounding factors that the results may produce. This information is also useful in identifying levels of other nutrient groups such as phytochemical intake or oily fish consumption and whether this has any effect on the results. It is important that the volunteers do not adapt their diet in any way and so it was stressed to the volunteer the importance of not increasing their portions of cruciferous or any other type of vegetable especially once they are on the intervention. Volunteers are instructed to record their intake of food, beverages and supplements consumed over a 7-day period. Towards the end of the 12 week dietary intervention, a 2.sup.nd 7-day diet diary is again completed to assess compliance to the intervention. The food intake diaries are analysed using 'Diet Cruncher' and UK food composition tables (McCance and Widdowson's The Composition of Foods, Sixth summary edition. Food Standards Agency (2002). Cambridge: Royal Society of Chemistry. ISBN 0-85404-428-0). Food intake from the diaries are put into Diet Cruncher v1.6.1 (Waydownsouthsoftware) and analyzed for differences in nutrient composition between the three intervention groups at baseline and 12 weeks after intervention.

Broccoli

The high glucosinolate (HG) broccoli is a hybrid cultivar that has an enhanced level of the glucosinolate called glucoraphanin (precursor of sulforaphane). Glucoraphanin is another name for 4-methylsulphinylbutyl glucosinolate (MSB)

The high glucosinolate (HG) broccoli used in the study has 6.1±0.65 micromol/g dry wt of the glucosinolate 3-methylsulphinylpropyl glucosinolate (MSP) and 16.7±0.36 micromol/g dry wt of the glucosinolate 4-methylsulphinylbutyl glucosinolate (MSB). For the avoidance of doubt glucoiberin is another name for 3-methylsulphinylpropyl glucosinolate (MSP).

The standard broccoli (sometimes referred to herein as "Ironman") used in the study has 0.9±0.07 micromol/g dry wt of the glucosinolate 3-methylsulphinylpropyl glucosinolate (MSP) and 5.64±0.50 micromol/g dry wt of the glucosinolate 4-methylsulphinylbutyl glucosinolate (MSB).

The two types of broccoli are distinguishable by their ntunber, broccoli 1 and broccoli 2. However it is not known to the scientists running the study or the volunteers participating in the study, which broccoli was the HG variety and which was the standard variety. Samples are packaged into 100 g portions and stored frozen at −18° C. The broccoli is then delivered frozen to the volunteer in their homes. The volunteer is asked to cook the broccoli from frozen for up to 5 minutes and peas for up to 3 minutes.

Cooking Guidelines for Frozen Broccoli

The portions of broccoli are steamed for up to 5 minutes and the peas for up to 3 minutes. It is important that volunteers did not overcook the broccoli as this would result in delayed absorption of isothiocyanates produced.

Previous studies have demonstrated cooking levels required to maximize the level of ITCs ingested (unpublished data). Levels of glucosinolate and the equivalent isothiocyanates in the high glucosinolate broccoli hybrid have been measured previously at IFR, Mithen et al (2003). The levels correspond to a 3-4 fold increase compared to standard supermarket broccoli.

Methods:

Physiological Measurements

These include PWV, AIx and ambulatory BPs. To ensure reproducible and accurate measurements, all volunteers are measured under similar conditions. It is important that the volunteer is relaxed (either lying or sitting down) and has abstained from caffeine, cigarettes, heavy meals or exercise prior to the measurement. All volunteers are encouraged to wear loose comfortable clothing on their clinical appointment days.

PWV is one of the oldest parameters used to determine arterial stiffness [68]. Arterial stiffness has been established as an independent predictor of CVD [68, 69]. PWV is measured using the Vicorder device from Skidmore Medical. The pulse wave velocity (m/s) of the measurement is presented with the standard deviation (PWV+/−SD). The standard deviation should be equal to or less than 10% of the velocity e.g. If the PWV=8.0 m/s, the SD should be <0.8. If this is not the case, the measurement is repeated until 3 values are obtained that satisfy this criteria [70].

The AIx is a simple and sensitive method of measuring arterial stiffness and is used to corroborate the PWV measurements. The measurement is carried out using an applanation tonometer using a device from SphygmoCor. The quality index is a number out of 100 that is derived from a number of quality control parameters including average height of pulse and pulse height variation. If the number is over 85, the reading is acceptable. If it is between 75-85, it is borderline. If it is less than 75, the reading is unacceptable [70].

Ambulatory blood pressure monitoring (ABPM) is a non-invasive method of obtaining blood pressure readings over a sustained period of time whilst the patient is a free living environment, representing what is hoped is a true reflection of their blood pressure. Many studies have now confirmed that blood pressure measured over a sustained period and up to 24 hours is superior to clinic based blood pressure in predicting future cardiovascular events [71]. Studies have shown that increased blood pressure readings on ABPM are more strongly correlated to end-organ damage than one off measurements e.g. left ventricular hypertrophy [72, 73]. They are also an effective method of overcoming white coat hypertension which can a problem when attempting to assess a volunteers true BP.

Biochemical Sampling

Figure 3:
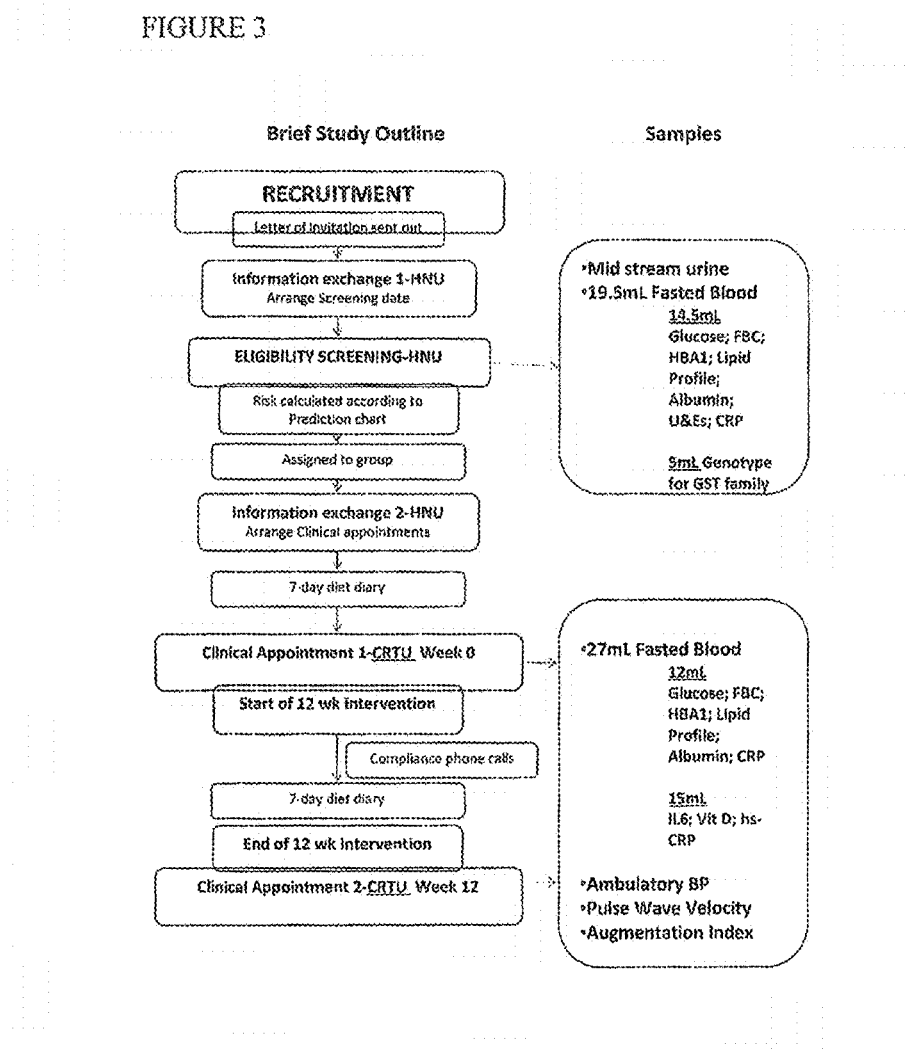
FIG. 3 shows an outline of the screening protocol undertaken including details of samples taken.

The following blood samples and volumes are taken in the order shown below (see FIG. 3). In total 55.5 mL of whole blood were taken from the volunteers over the entire course of the intervention. This may have been increased by 14.5 mL if the volunteer came back for a rescreen appointment requiring a second blood to be taken. The nurse aimed to collect the complete sequence of blood samples each time:

Eligibility Screening (HNU)=19.5 mL:
Sample 1=1×3.5 mL of blood for serum=3.5 mL
  Glucose
Sample 2=1×3.5 mL for serum=3.5 mL
  Serum lipid profiles
Sample 3=1×3.5 mL for plasma=3.5 mL
  Albumin, U+Es and CRP
Sample 4=1×4 mL for plasma=4 mL
  Full blood count
Sample 5=1×5 mL blood for plasma=5 mL
  Genotyping (GSTP1, GSTT1 & GSTM1)

At screening a 5 mL sample of blood is taken from which genomic DNA was extracted using the QIAamp DNA Mini kit protocol (Qiagen Inc). Samples were doubly encrypted to protect the volunteer's identity. DNA samples extracted from whole blood are amplified using real-time PCR using the method of Cotton et al (2000), to determine the presence or absence of GSTM1 and GSTT1 genotypes. The frequency of variant alleles for GSTPi are also determined.

Clinical Appointment 1 and 2: 2×18 ml
Sample 1=1×3.5 mL for serum=3.5 mL
  Glucose & CRP
Sample 2=1×5 mL for serum=5 mL
  Serum lipid profiles
Sample 3=1×3.5 mL for plasma=3.5 mL
  Albumin and FBC
Sample 4=6 mL blood for plasma/serum=6 mL
  IL6, vit D (25-hydroxy-vit D) and hs-CRP The blood samples for the analysis by ELISAs are aliquoted into a vacutainer and left to stand at room temperature for 30-60 minutes to produce serum. The tubes are centrifuged at 2200×g for 15 minutes and the serum aliquoted into six-ten 1.5 mL cryovials pre labelled for each of the analyses, IL6, vit D and hs-CRP. These cryovials are immediately placed in dry ice and stored at −80° C. until analysis.

If plasma is used for the ELISAs, the whole blood transferred to EDTA coated blood tubes is centrifuged at 1210×g at room temperature for 10 minutes. The plasma layer is carefully removed and transferred to six-ten 1.5 mL cryovials pre labelled for each of the analyses, IL6, Vit D and hs-CRP.

These cryovials are immediately placed in dry ice until they are safely transported stored at −80° C. until analysis.

Standard ELISAs from Quantakine and IDS are used for the analysis of IL6, vitamin D and hs-CRP.

IL6—Quantikine D6050;
hs-CRP Quantikine ELISA Kit-DCRP00.

Interleukin 6 (IL6) and C reactive protein (CRP) are both sensitive physiological markers of systemic inflammation. IL6 is a multifunctional signalling molecule that can act in a pro inflammatory and anti inflammatory way. It is released by a variety of cells in response to trauma and or tissue damage as resulting in inflammation [74]. CRP is an acute phase protein also found in elevated levels as a result of inflammation. In fact CRP, which is produced in the liver by hepatocytes, is regulated by levels of IL6 [75]. The persistence of an inflammatory state has been suggested to be the cause of a large number of age related chronic diseases [76] and there is increasing evidence to suggest that inflammation and indeed elevated levels of IL6 and CRP play a major role in CVD [77]. Several large cross sectional studies have concluded that elevated levels of CRP in plasma is one of the strongest independent predictors of CVD [78]. Measuring high sensitivity CRP (hs-CRP) gives greater accuracy in measuring low levels of CRP. Following a stimulus, levels of CRP can increase 10,000 fold from circulating values of 50 μg/L up to 500 mg/L in extreme cases [79].

As inflammation is associated with CVD and CVD risk, the levels of these key inflammatory markers are measured in volunteers to ascertain a link between the levels of IL6, hs-CRP, total cholesterol and the physiological measurements which are impacted by the inflammatory process, as result of the consumption of cruciferous vegetables.

Vitamin D (Vit D) (25-hydroxy-vit D)-IDS AC-57F-1;

Vit D is traditionally associated with bone health; however it is now known that it has become increasing important for the optimal functioning of the cardiovascular system [80]. Emerging data suggests that vit D status plays an important role in the development of CVD, with deficiency increasing the likelihood of conditions like hypertension, diabetes, metabolic syndrome, left ventricular hypertrophy, congestive heart failure and chronic vascular hypertrophy [80-82]. Vit D exists in two forms, vit $D_2$ (ergocalciferol) and vit $D_3$ (cholecalciferol), the foimer found in plants and is a product of ultraviolet B (UVB) irradiation of ergosterol, the latter from the irradiation of 7 dehydrocholesterol in the human epidermis [81]. Vit $D_2$ can be consumed as a supplement or in foods that have been fortified, whereas vit $D_3$ is produced by humans or consumed in the form of oily fish [81]. In the liver vit D is converted into 25-hydroxy-vit D (25(OH) vit D) which reflects the vit D intake and endogenous production and therefore is the compound that must be assessed in order to determine total vit D status. In a cross sectional study with 15,088 people on the NHANES III (3$^{rd}$ National Health and Nutrition Examination Survey[83]) national cohort registry, it was found that there was an inverse relationship between 25(OH) vit D and hypertension, diabetes mellitus, hypertriglyceridemia and obesity [84].

There are many other studies that concur with this finding and as this study is examining cardiovascular risk markers, vit D status in our cohort is assessed to establish a link ourselves. Volunteers are assessed as to whether they fall within the vit D deficiency (<37.4 nmol/L) or replete (>37.4 nmol/L) groups [85] and how this relates to changes in total cholesterol concentration and the physiological measurements we are taking.

Results

The results are provided for the effect of glucosinolates on total cholesterol, LDL—cholesterol, systolic blood pressure (BP); diastolic blood pressure (BP) and cardiovascular disease (CVD) risk.

TABLE A

|  | Ironman (n = 8) (standard broccoli) | HG1 (n = 10) High glucosinolate broccoli | Peas (n = 7) (control) |
| --- | --- | --- | --- |
| Total cholesterol | ns | −0.47 mmol/L; p = 0.009 | ns |
| LDL cholesterol | ns | −0.3 mmol/L; p = 0.027 | ns |
| HDL cholesterol | ns | ns | ns |
| Serum triglycerides | ns | ns | ns |
| Systolic BP | ns | −5.0 mmHg; p = 0.037 | ns |
| Diastolic BP | ns | −4.0 mmHg; p = 0.01 | ns |
| Cardiovascular risk | ns | −1.6%; p = 0.008 | ns |

The CVD risk, as discussed above, is calculated using data on blood pressure, lipid profile and several demographic factors as detailed above. This risk assessor is widely used by clinicians to estimate the percentage risk of CVD within the next 10 years.

Table A above shows the results for systolic blood pressure (BP), diastolic blood pressure (BP), total cholesterol, LDL-cholesterol mmol/L and CVD risk (% event in next ten years) with pea, standard broccoli "Ironman" and high glucosinolate broccoli (HG1) treatments. The p value is from a paired T-test. $P<0.05$ is significant, $P>0.05$ is not significant (ns).

As can be clearly seen the high glucosinolate broccoli (compared with the standard broccoli and/or the pea control) results in a significant reduction in systolic blood pressure, diastolic blood pressure (BP), total cholesterol, LDL cholesterol and CVD risk in the subjects tested.

Notably the peas (negative control) and standard broccoli do not result in any significant change in systolic blood pressure, diastolic blood pressure (BP), total cholesterol, LDL-cholesterol or cardiovascular disease risk.

The high glucosinolate broccoli also results in a significant reduction in total cholesterol, whereas peas and standard broccoli did not result in any significant change in total cholesterol levels.

Example 2

Effect of Consumption of High Glucosinolate Broccoli Cell Signalling Pathways in Patients Having Prostate Cancer Subjects and Study Design Twenty-two male volunteers aged 57-70 years (Table 1) with a previous diagnosis of high-grade prostatic intraepithelial neoplasia (HGPIN), the pre-invasive in situ stage of prostatic adenocarcinoma, were recruited by a consultant urologist at Norfolk and Norwich University Hospital NHS Trust. Histological diagnosis was made by two consultant histopathologists, who had a special interest in prostate pathology. Ethical approval for the trial was obtained from the Norfolk Research Ethics Committee. All participants gave written, informed consent. Volunteers were excluded if they were undergoing chemopreventive therapy, were receiving testosterone replacement medication or 5 alpha reductase inhibitor, had active infection requiring treatment, had a body mass index (BMI)<18.5 or >35, or were diabetic. Subjects were allocated into a 12-month, parallel dietary intervention trial consisting of two dietary intervention groups: (i) consuming 400 g broccoli per week or (ii) consuming 400 g peas per week, in addition to their normal diet. Plasma prostate specific antigen (PSA) levels were quantified prior to the intervention study and after six and 12 months at the Norfolk and Norwich University Hospital with the use of a total PSA immunoassay. Volunteers avoided foods known to contain glucosinolates for 48 hours prior to each biopsy appointment to avoid acute effects.

In addition to the transrectal ultrasound scan (TRUS)-guided needle biopsies of the prostate obtained from the volunteers immediately prior to the intervention study, and after six and twelve months, 18 benign and 14 malignant transurethral resection of the prostate (TURP) tissues were also obtained from the Norfolk, & Norwich University Hospital Partners in Cancer Research Human Tissue Bank.

Dietary Intervention

Vegetables were delivered to the volunteers on a monthly basis. They were provided with a steamer and the volunteers were given a demonstration by the diet cooks at the Institute of Food Research of how to cook the vegetables. Portions of broccoli were steamed for 4-5 minutes and portions of peas were steamed for 2-3 minutes. Frozen peas (Birds Eye Garden Peas, Birds Eye) were purchased from a local retail outlet. To ensure consistency in glucosinolate content in frozen broccoli provided to the volunteers, the broccoli required for the intervention study was grown in one batch at an ADAS experimental farm at Terrington, near King's Lynn, UK (ADAS) and processed by Christian Salvesen (Bourne, Lincolnshire, UK, Salvesen). It was blanched at 90.1.degree. C. for 74 s, frozen at −30.degree. C. and packaged into 100 g portions, then stored at −18.degree. C. until steamed by the volunteer. The broccoli was a high glucosinolate variety [19, 20]. The levels, mean (SD), of 4-methylsulphinylbutyl and 3-methylsulphinylpropyl glucosinolates (the precursors of SF and IB, respectively) were 10.6 (0.38) and 3.6 (0.14) .mu.molesg.sup.-1 dry weight, respectively, compared to 4.4 (0.12) and 0.6 (0.01).mu.moles.sup.-1 dry weight in broccoli purchased from local retail outlets. Although the level of glucosinolates were higher than standard broccoli, blanching prior to freezing denatured plant myrosinase, thus the levels of SF and IB derived from the high glucosinolate broccoli diet would be similar to or lower than those obtained from fresh broccoli with functional myrosinase. Levels of indole glucosinolates were similar in both high glucosinolate and standard broccoli.

Compliance Monitoring and Dietary Assessment

Volunteers completed weekly tick sheets during the 12-month intervention period to identify when the portions of vegetables were eaten. Every two weeks, volunteers were contacted by telephone and asked about adherence to the diet. A seven-day estimated food intake diet diary was completed by volunteers at baseline and after six months using household measures as an indication of portion size. Food intake from the diaries was inputted into Diet Cruncher v1.6.1 (Waydownsouthsoftware) and analyzed for differences in nutrient composition between the two intervention groups at baseline and six months after intervention.

Genotyping

Genomic DNA was extracted from whole blood or from tissue samples using Qiagen QIAamp DNA minikit with RNase treatment according to the manufacturer's instructions (Qiagen). GSTM1 (NM.sub.—000561) genotype was determined using a real-time PCR procedure based on. Covault and colleagues, using gene specific primers and probe and quantified relative to a two-copy gene control, a region in IVS10 of the breast cancer 1, early onset (BRCA1, NM.sub.—007294) gene [21]. Primers and probes were designed using Applied Biosystems Primer Express (http://www.appliedbiosystems.com/) and are given with PCR conditions in FIG. 14. Data were analyzed with Applied Biosystems Absolute Quantification software.

RNA Extraction and Microarray Hybridisation

Total RNA was isolated from the TURP tissue bank samples and the TRUS-guided needle biopsies from the volunteers with the use of QIAGEN® RNeasy mini kits according to the manufacturer's instructions (Qiagen). The quantity of resulting RNA was measured using a spectrophotometer (Beckman). The RNA quality was determined using the Agilent 2100 Bioanalyzer (Agilent). RNA samples from TURP biopsies of benign and malignant prostates and from TRUS-guided biopsies from both subject groups (peas and broccoli) at baseline, and at six and 12 months after intervention were hybridized onto Affymetrix Human U133 Plus 2.0 microarrays (Affymetrix) by the Nottingham Arabidopsis Stock Centre (NASC). Double-stranded cDNA synthesis and generation of biotin-labeled cRNA were performed according to the manufacturer's protocol (Affymetrix). The final cRNA was checked for quality before fragmentation and hybridization onto the arrays. One of the 22 volunteers was diagnosed with prostatic adenocarcinoma at the study baseline biopsy and was removed from the study. Eleven samples from the baseline biopsies, two samples from the six-month biopsies and three samples from the 12-month biopsies did not produce good quality RNA and/or sufficient cRNA and were not hybridized. In addition, one volunteer showed prostatic adenocarcinoma at the six-month biopsy; subsequent samples were removed from the study. Fluorescence intensity for each array was captured with a GeneChip® Scanner 3000 7G. Affymetrix GeneChip® Operating Software (GCOS) was used to quantitate each U133 Plus 2.0 array. Microarray data in this paper are compliant to the minimum information about a microarray experiment (MIAME) criteria and are deposited at Array Express EBI Accession Number E-MEXP-1243).

Microarray Data Analysis

Raw data files (CEL) were loaded into the DNA-Chip Analyzer software (dChip, Harvard, build date September 2006) for normalization, generation of expression values and statistical analysis. Following normalization using the Invariant Set Normalization method, probe expression levels were calculated using the PM-only model. To identify genes that were changing between groups, different two-tailed P-value thresholds were applied calculated by Welch modified two-sample t-test in dChip. Paired or unpaired t-tests were performed as appropriate. To correct for multiple testing, False Discovery Rate (FDR) was estimated by permutation in dChip and the median of 100 permutations reported for each of the comparisons (1000 permutations on selected samples had little effect on FDR calculations). Unsupervised clustering was performed on benign and malignant samples using 1-Rank correlation as distance metric on a gene list of 3697 probes. These probes satisfied two criteria: first, that the coefficient of variation (CV) was between 0.5 and 1000; and secondly, that the percentage of Presence calls was more than 20% across all TURP benign and malignant samples.

For the purpose of sample classification, 19 laser-capture microdissected (LCD) epithelial cell microarrays (GEO Accession: GDS1439, NCBI) and 32 TURP benign and malignant microarrays were normalized together and model-based expression was calculated as described above in dChip. The LCD samples were derived from six benign prostate tissue samples, five clinically localized primary prostatic adenocarcinoma samples, two replicates of the five primary cancer samples after pooling, four metastatic prostatic adenocarcinoma samples and two replicates of the four metastatic prostate cancer samples after pooling [22]. Classification of the LCD epithelial cell samples was then performed using linear discriminant analysis (LDA) based on the TURP benign and malignant samples as training samples. LDA was performed using 442 probes that had higher than 100 units difference in signal intensity between TURF benign and malignant samples and were significantly different at P≤0.01 by Welch modified two-sample t-test. To identify pathways that are the most over-presented in the lists of differentially expressed genes, functional analyses using MAPPFinder and GenMAPP v2.1 were performed (GenMAPP).

Incubation of Peptides with Isothiocyanates

Incubations of SF or IB with bovine insulin (P01308, Sigma-Aldrich), recombinant human epidermal growth factor (EGF, P01133, R&D Systems, http://www.rndsystems.com/) and recombinant human transforming growth factor beta 1 (TGFβ1, P01137, R&D Systems) were performed in sodium phosphate-buffered saline solution (pH 7.4) or human blood plasma at 37° C. for 0.5-24 h. Plasma was pre-treated by ultrafiltration to remove high molecular weight proteins (Microcon Ultracel YM-30 filter, MWCO 30,000). Samples were either analyzed directly by LC-MS/MS or by LC-MS/MS analysis of tryptic digests of gel electrophoresis bands.

Direct LC-MS/MS Analysis of Peptides Incubated with Isothiocyanates

The LC system used was a Shimadzu series LOAD VP (Shimadzu). The column was an ACE 300 C18, 150×2.1 mm (5 μm particle size) used at 40° C. Mobile phase A was 0.1% formic acid in water, mobile phase B, 0.1% formic acid in acetonitrile and the flow rate was 0.25 ml/min. A linear gradient was used from 25% B to 35% B over 0 to 5 min, then a further gradient from 35% B to 99% B over 6 min followed by 99% B for 4 min. The column was re-equilibrated for a total of 3 min. The injection volume was between 5-20 μl. All MS experiments were conducted on a 4000 QTRAP hybrid triple-quadrupole linear ion trap mass spectrometer using Analyst version 1.4.1 software (Applied Biosystems) equipped with a Turbolon source used in positive ion electrospray mode. The probe capillary voltage was optimized at 4200 V, desolvation temperature set to 400° C., curtain gas, nebulizing and turbo spray gas were set to 40, 10 and 20, respectively (arbitrary values). Declustering potential was ramped between 50-120 V. Nitrogen was used for collisionally induced dissociation (CID). The peak-width was set on Q1 and Q3 at 1.0 Th (measured at half height) for all MS and MS/MS experiments. Spectra were obtained over the range m/z 800-2000 with scan times of 1-2 sec. Operating in LIT mode Q0 trapping was activated and dynamic fill time used, the scan rate was set to 250 Th/s for enhanced product ion (EPI) scans, excitation time was 150 msec, excitation energy 25 V and entry barrier 4 V. For EPI spectrum acquisition the precursor ions of interest for conjugates of SF with insulin (m/z 1183.9 $MH_5^{5+}$), EGF (m/z 1088.8, $MH_5^{6+}$) and TGF.beta. (m/z 1981.9, $MH_5^{13+}$) were selected, the collision energy was ramped between 30-120V and spectra were obtained over the range m/z 100-1500 with a scan time of 1.9 sec. $MS^3$ settings were identical to $MS^2$ except that the collision energy was 50-80 V and declustering potential was 50-80 V.

LC-MS/MS Analysis of TGFβ1 Incubated with SF Following Electrophoresis and Tryptic Digestion 1 μg aliquots of the TGF.beta.1 protein, supplied with bovine serum albumin as carrier, were incubated with either DMSO or 1.2 μmoles of SF for 30 minutes at 37° C. and run onto denaturing 4-12% Bis-Tris NuPAGE gels (Invitrogen). Bands were excised and digested with trypsin (Promega) after reduction with dithiothreitol (DTT) and alkylation with iodoacetamide (Sigma-Aldrich). Extracted peptides were lyophilized and re-dissolved in 1% acetonitrile, 0.1% formic acid for analysis by mass spectrometry. LC-MS/MS analysis was performed using a LTQ mass spectrometer (Thermo Electron Corporation) and a nanoflow-HPLC system (Surveyor, Thermo Electron). Peptides were applied to a precolumn (C18 pepmap100, LC Packings) connected to a self-packed C18 8-cm analytical column (BioBasic resin ThermoElectron; Picotip 75 p.m id, 15 p.m tip, New Objective). Peptides were eluted by a gradient of 2 to 30% acetonitrile in 0.1% formic acid over 40 min at a flow rate of approximately 250 nL min$^{-1}$. Data-dependent acquisition of MS/MS consisted of selection of the five most abundant ions in each cycle: MS mass-to-charge ratio (m/z) 300 to 2000, minimum signal 1000, collision energy 25, 5 repeat hits, 300 sec exclusion. In all cases the mass spectrometer was operated in positive ion mode with a nano-spray source and a capillary temperature of 200° C., no sheath gas was employed; the source voltage and focusing voltages were optimized for the transmission of angiotensin. Raw data were processed using BioWorks 3.3 (Thermo Electron Corporation). Searches were performed with Mascot (Matrix Science) against SPtrEMBL (4719335 sequences) restricted by taxonomy to Homo sapiens (68982 sequences), oxidized methionine and carbamidomethyl cysteine residues were allowed as variable modifications as was putative SF. The error tolerance of the parent ion was ±1.2 Da and the fragment mass tolerance was 0.6 Da, one missed cleavage was permitted. Error tolerant searches in Mascot against TGF.beta. were routinely performed and extracted ion chromatograms and manual inspection of spectra were prepared using Qual Browser and BioWorks 3.3 (Thermo Electron Corporation).

Luciferase Reporter Gene Assay

NIH 3T3 cells stably transfected with a CAGA12-luc plasmid, which responds to Smad activation [23], were cultured in DMEM supplemented with 10% fetal calf serum (FCS), 1% penicillin, 1% streptomycin, 1% L-glutamine and 0.4 mg/ml geneticin. Cells were seeded into complete growth medium in a six-well tissue culture dish for 24 h, after which the medium was replaced with low serum medium (0.5% FCS) containing one of three treatments: (1) TGFβ1 (to achieve a final concentration of 2 ng ml$^{-1}$) in PBS buffer, (2) TGFβ1$^{+10}$ mM DTT in PBS buffer (3) TGFβ1$^{+2}$ μM SF in PBS buffer. To simulate SF pharmacokinetics, all test samples were incubated at 37° C. for 30 minutes prior to dialysis, performed in PBS buffer for 4 hours using Slide-A-Lyzer Dialysis Cassettes MWCO 3.5K (PIERCE). Dialysis reduced SF concentration to 34 nM. As additional controls, cells were treated with PBS without TGF.beta.1 and PBS with SF (34 nM). The luciferase activity was determined 16 h following treatment using the Luciferase Reporter Gene assay (Roche Applied Science) in a Perkin Elmer Wallac Victor 2 1420 multilabel counter plate reader (Perkin Elmer). Briefly, cells were washed twice with PBS and lysed in cell lysis buffer supplied with the assay. Chemiluminescence was immediately quantified following the addition of luciferase assay substrate. Luciferase values were normalized to protein concentration quantified using the BCA assay (Sigma-Aldrich). The experiment was repeated four times, with three replicates of each treatment per experiment. Statistical analysis was performed using 1-way ANOVA with the statistical software, R [24].

Results

Comparison of Gene Expression of Benign and Malignant TURP Tissue Samples

We compared global gene expression profiles in surgically resected benign and malignant prostate TURF tissue using RNA extracted from heterogeneous tissue (such as we intended to use in the intervention study). Unsupervised clustering distinguished unambiguously the benign and malignant samples. Pathway analyses for genes that were significantly different between the two groups were undertaken with the use of GenMapp software, and identified pathways that are frequently reported to be perturbed during carcinogenesis (Tables 2a and 3a). To validate further our methods of data analysis and to determine whether microarray data from gross heterogeneous tissue are comparable to data generated from LCD epithelial cells, we analyzed independent data sets of LCD epithelial cells (GEO Accession: GDS1439) from benign, localized and metastatic prostate cancer. We used our benign and malignant samples as a training set for linear discriminant analyses (LDA) and the independent data as test sets, and found that the LDA model correctly distinguished the benign, localized and metastatic LCD epithelial cell samples (FIG. 5). Thus, this preliminary study provides validation for our approach to the statistical analyses of array data.

Variation in Plasma PSA Levels

PSA levels prior to the intervention were in similar range to that previously reported for men of an equivalent age range diagnosed with HGPIN [25]. There was no significant association with GSTM1 genotype, and no consistent changes in PSA levels after six or 12 months within either arm of the intervention study (Table 1).

Differences in Global Gene Expression Between GSTM1 Positive and Null Individuals We initially genotyped the resected TURP tissue samples and compared gene expression profiles between GSTM1 positive and null genotypes within the benign and malignant samples. We found few differences between genotypes, with similar high median false discovery rates (FIG. 6a, Table 3b). Likewise, we compared gene expression profiles obtained from needle biopsies of the prostate from GSTM1 positive and null men who had previously been diagnosed with HGPIN and found few differences.

We then compared gene expression profiles between GSTM1 genotypes in needle biopsy tissue of twenty-one men who had been recruited into the dietary intervention study. Eight of the men within this study had been asked to consume 400 g of steamed frozen peas per week, and the other thirteen were requested to consume 400 g of steamed frozen broccoli per week, but otherwise to consume their normal diet. Diet was assessed with seven-day diet diaries prior to the intervention and after six months. No significant differences were found in diet components, apart from the consumption of broccoli and peas (Table 4). We found many differences in the prostate gene expression between GSTM1 positive and null men who had been on the broccoli diet for six months, but few, if any, differences in gene expression between GSTM1 positive and null men who had been on the pea diet (FIG. 6a, Table 3b). To investigate the potential consequences of the differences in gene expression between GSTM1 genotypes following the broccoli-rich diet, we analyzed these data via GenMapp. Three pathways, EGF receptor, adipogenesis and TGFβ receptor, were identified in which genes occurred at a higher frequency than they would by chance (Table 2b).

Changes in Gene Expression Before and after the Dietary Intervention

We used paired t-tests to identify genes that had changed in expression between 0 and 6 months and 0 and 12 months in biopsy samples from individuals within each arm of the intervention to quantify changes in expression with time. Within the broccoli arm, we restricted analyses to GSTM1 positive individuals. We found after both 6 months and 12 months there were more changes in expression within the broccoli-rich arm than the pea-rich arm (FIG. 6b, Table 3c). Pathway analyses with genes that changed in expression between 0 and 12 months identified changes only in the androgen receptor pathway in the pea-rich arm, while in the broccoli-rich arm androgen receptor pathway was identified, along with several other signalling pathways, including insulin signalling, TGFβ and EGF receptor pathways (Table 2c). Analyses with genes that changed in expression between 0 and 6 months in the broccoli arm also identified changes in TGFβ receptor pathway (adjusted P=0.001), insulin signalling (adjusted P=0.035) and EGF receptor signalling (adjusted P=0.068).

Thus, evidence for the effect of broccoli consumption on modulation of TGFβ and EGF signalling has been obtained in two independent analyses: Firstly, the comparison of gene expression profiles of GSTM1 positive and null individuals who had consumed the broccoli-rich diet for six months, and, secondly, the paired analyses of gene expression profiles from biopsies obtained at 0 and 12 months from GSTM1 positive individuals who had consumed the broccoli-rich diet. It is important to note that these analyses do not share any array data sets.

Chemical Interactions Between TGFβ1, Insulin and EGF Peptides and Broccoli Isothiocyanates Having demonstrated that broccoli consumption modulates several cell signalling pathways, we sought an explanation. Incubation of insulin, EGF and TGFβ1 peptides with the isothiocyanates SF or IB in PBS pH 7.4 at 37° C. for a period of 0.5 to 24 hours gave consistent evidence of the formation of a covalently bound conjugate of the respective peptide and the ITC. This was further investigated for physiological relevance by performing the same incubations in human plasma depleted of high MW proteins. LC-MS/MS analysis showed the appearance of one or more additional LC-MS peaks when SF or IB were incubated with the peptides. For example, in FIG. 7 an extracted ion chromatogram (m/z 1183.9, corresponding to insulin-SF $MH_5^{5+}$) shows the appearance of two insulin-SF conjugates compared with the control incubation. M. analysis of these peaks (FIG. 8) confirmed the presence of two diagnostic fragment ions at m/z 235 and m/z 325 corresponding to the addition of SF to the two N-terminal amino acids of insulin Gly-SF and Phe-SF. Similar results were obtained to identify Gly-IB (m/z 221) and Phe-IB (m/z 311) from the incubation (data not shown). Comparable evidence was obtained for the formation of EGF conjugates with SF in human plasma corresponding to the addition of SF to the N-terminal asparagines residue (m/z 309) of EGF.

To provide additional information of modifications to TGFβ1, we adopted a complementary approach. 1 μg aliquots of the protein were incubated with either DMSO or 1.2 μmoles of SF for 30 minutes at 37° C. and separated by SDS-PAGE electrophoresis. Bands were excised and digested with trypsin before analysis by LC-MS/MS. TGFβ1 was robustly identified in bands of 25 kDa corresponding to the active dimer. The N-terminal peptide ALDTNYCF-SSTEK was identified from parent ion m/z 768.5 in both DMSO (control) and SF-treated samples (FIG. 9). A precursor ion m/z 877.2 was observed only in SF treated samples. MS/MS analysis of both precursor ions revealed a strong series of fragment peaks that were common to both (FIG. 10) precursor ions. These fragmentation patterns are consistent with the unmodified y ion series for the peptide ALDTNY-CFSSTEK (including carbamidomethyl cysteine +57) and a b ion series shifted by 217.4±0.8 Da in the SF-treated sample. These results strongly support an N-terminal modification to TGFβ1 by SF. Addition of SF would result in a mass addition of 177, as observed with LC-MS analyses of intact TGFβ1, as described above. It is highly likely that the addition of 217, as opposed to 177, is due to subsequent reaction of the thiourea with iodoacetamide, added to the reaction mixture to alkylate reduced disulphide linkages, to result in a mixture of isomeric carbamimidoylsulfanylacetamides, which undergo cyclisation and loss of $NH_3$ to give the corresponding iminothiazolidinones.

Enhancement of TGFβ1 Signalling after Pre-Incubation with Sulforaphane

As thiourea derivatives of proteins produced by isothiocyanates have been shown to modify physicochemical and enzymatic properties [26,27], we sought to assess whether SF modification of extracellular signalling proteins had functional consequences. We focussed on TGFβ1 signalling due to its profound role in maintaining tissue homoeostasis through controlling cell proliferation and behaviour [28,29]. TGFβ1-induced Smad-mediated transcription was quantified in NIH3T3 cells stably transfected with a CAGA12-luc plasmid, in which luciferase activity can be measured upon activation of Smad proteins [30]. Exposure of cells to TGFβ1 induced luciferase activity as expected. When cells were exposed to TGFβ1 that had been pre-incubated with physiologically appropriate concentrations of SF (2 μM) for 30 minutes followed by dialysis, to simulate SF plasma pharmacokinetics [14], there was an increase in Smad-mediated transcription compared to exposure to TGFβ1 alone (FIG. 11). Exposure of cells to the residual SF (34 nM) did not result in enhanced transcription suggesting that SF induces Smad activation indirectly, consistent with our previous observation that SF binds to the ligand itself. It is also conceivable that SF may interact with the extracellular domain of the receptor to alter downstream signalling.

Incubation of ITCs with EGF

A further example of the functional consequences of interactions between ITCs and signalling peptides is given in FIG. 15, showing that incubation of ITCs with EGF can suppress EGF signalling in BPH cells, a model of hyperplastic prostatic tissue. EGF binds to and phosphorylates the EGF receptor which activates the down stream signalling pathway. Data presented shows that pre-incubation of EGF with 4-methylsulphinylbutyl ITC(SF) under conditions known to cause peptide modification reduces the amount of phosphorylated receptor compared to EGF alone. This would be expected to result in inhibition of the EGF signalling pathway, with anti-inflammatory consequences.

Combination of ITCs and Procyanidins

We first freeze-dried rocket salad and extracted the ITCs in PBS (200 mg in 5 ml PBS). HPLC quantification showed that this contained around 100 uM sulforaphane, 200 uM iberin and unknown quantity of other ITCs.

The experiment consists of 10 sample treatments all done in biological triplicates. HUVEC cells were treated with the treatments below for 45 min before adding 10 ng/ml TNFa in the treatments 2-10. After 6 hours, media and protein lysates were collected and stored at −20° C. I then did IL-6 Quantikine ELISA (R&D Systems) in the media and BCA quantification (Sigma) for cell protein content.

The treatments are (names in parenthesis are the sample names in the graphs in FIG. 16):

1) Control (C)
2) Control (TNF)
3) 2 μg/ml procyanidins GE (GE)
4) 1 μM rocket extract (1RkE)
5) 5 μM rocket extract (5RkE)
6) 10 μM rocket extract (10RkE)
7) 25 μM rocket extract (25RkE)
8) 2 μg/ml procyanidins GE+1 uM rocket extract (GE+1RkE)
9) 2 μg/ml procyanidins GE+5 uM rocket extract (GE+5RkE)
10) 2 μg/ml procyanidins GE+10 uM rocket extract (GE+10RkE)

The results of the experiment are shown in FIGS. 16 and 17.

Production of a Cultivar with High Levels of 3-methylthiopropyl (3-Mtp) Glucosinolate To produce a cultivar of a plant (e.g. broccoli or another variety of *B. oleracea*) with high levels of 3-methylthiopropyl glucosinolate, one would need to combine the null alleles of the *B. oleracea* GSL-ELONG locus with the null alleles at the *B. oleracea* GSL-ALK locus [52-54]. A possible source of suitable alleles would be *B. drepanensis*, *B. macrocarpa*, *B. rupestris* or *B. villosa*, all of which are members of the n=9 *B. olereacea* species complex. Suitable molecular markers for these alleles can be used to enhance the rate of introgression of these alleles into a commercial agronomic genetic background.

Discussion

To our knowledge, this is the first dietary intervention study to analyse global gene expression profiles within a target tissue before and after a 12 month intervention, and to stratify gene expression profiles by genotype. While we do not observe any consistent changes in plasma PSA levels over the 12 month period of the intervention, we were able to quantify extensive changes in gene expression. We find little evidence to support potential mechanisms derived from animal and cell models to explain the observational data that consuming broccoli may reduce risk of cancer, but considerable evidence for the perturbation of several signalling pathways that are associated with carcinogenesis and inflammation (Table 2b and c). It is possible that the net effect of perturbation of these pathways may reduce the risk of cell proliferation, and maintain cell and tissue homoeostasis. It is of considerable interest that broccoli intervention is associated with perturbation of TGFβ1, EGF and insulin signalling, each of which has been associated with prostate carcinogenesis [31-35], in addition to carcinogenesis at other sites [28,36,37], and inflammation associated with myocardial infarction [38]. It is noteworthy that broccoli consumption was also associated with alterations in mRNA processing.

It is likely that the major bioactive products derived from broccoli are the isothiocyanates, including sulforaphane and iberin. These have been shown to have a multitude of biological activities in cell models consistent with anticarcinogenic activity [15]. However, these studies largely involve exposing cells to concentrations of SF and IB far in excess of those which occur transiently in the plasma after broccoli consumption, and are mediated by the intracellular activity of the ITCs by, for example, perturbing intracellular redox status, depletion of glutathione and perturbation of the Keap1-Nfr2 complex. We question whether these processes would occur in vivo, as any of the ITCs entering cells would immediately be inactivated through conjugation with glutathione that would be present in relatively high concentration. Thus, we explored whether the biological activity of ITCs may be mediated through their chemical interaction with signalling peptides within the extracellular environment of the plasma, which has a low glutathione concentration. We demonstrated that ITCs readily form thioureas with signalling proteins in the plasma through covalently bonding with the N-terminal residue. It is likely that ITCs chemically react with other plasma proteins and a global analysis of plasma protein modifications by ITCs is warranted. It is also possible that other types of chemical modification of plasma proteins by ITCs may occur, such as covalent bonding through cysteine and lysine residues [39, 40].

Previous studies have shown that isothiocyanate-derived thioureas modify the physicochemical and enzymatic properties of the parental proteins [26,27]. Thus, it is possible that the perturbation of signalling pathways in the prostate is mediated by protein modifications that occur in the extracellular environment. We provide further evidence for this hypothesis by demonstrating that pre incubation of TGFβ1 with a physiological appropriate concentration of SF (2 μM for 30 minutes), followed by dialysis for 4 h to simulate SF pharmacokinetics, results in enhanced Smad-mediated transcription. As TGFβ1/Smad-mediated transcription inhibits cell proliferation in non-transformed cells [31,41], the enhancement of Smad-mediated transformation by SF would be consistent with the anticarcinogenic activity of broccoli, in addition to reduced risk of myocardial infarction [10,38]. In certain circumstances, enhancement of TFFβ signalling has been associated with tumour progression within already initiated cells, although the precise pathways by which this is mediated have not been fully resolved [42]. It is potentially the net effect of changes in several pathways, as opposed to just TGFβ1, which may underlie the observed reduction in both cancer and myocardial infarction through broccoli/crucifer consumption.

A previous study has demonstrated that isothiocyanates can inhibit EGF signalling, but without a mechanistic explanation [43]. In the current study, we show that SF will bind to the EGF ligand, and this may underlie our results and those reported previously [43]. Moreover, chemical modification of signalling proteins by ITCs may be complemented by modification of receptor proteins, as has previously been shown for the TRPA1 receptor [39,40].

Perturbation of signalling pathways is additionally determined by GSTM1 genotype. The interaction between diet and GSTM1 on gene expression may partially explain the contradictory results from those case control studies which lack dietary assessment and which have or have not associated the GSM/null genotype with enhanced risk of prostate cancer [44-47]. GSTM1 enzyme activity catalyses both the formation and the cleavage of SF-glutathione conjugates [48]. We suggest that following transport into the plasma from enterocytes, GSTM1 activity (originating either from hepatic cell turnover [49] or leakage from peripheral lymphocytes [50]) catalyses the cleavage of the SF-glutathione conjugate within the low glutathione environment of the plasma [51] to determine the extent of free SF that is available for protein modification, as discussed above, and which is not excreted via mercapturic acid metabolism (FIG. 4). Thus low levels of SF, as would be expected from normal dietary consumption of broccoli, may lead to subtle changes in cell signalling, which, over time, result in profound changes in gene expression. In this manner, consuming one portion of broccoli per week if one is GSTM1 positive, or more if one is GSTM1 null [14], may contribute to a reduction in cancer risk.

In addition to the insight this study provides to the effect of broccoli consumption on gene expression, we consider that our study may have broader implications. First, we demonstrate that routine prostate needle biopsies can be used for global gene expression analyses in addition to histological assessment, and that it is possible to monitor changes in expression with time. It is notable that men within both dietary arms of the study had significant changes in the androgen receptor pathway. It is possible that these changes in androgen signalling are associated with aging and independent of diets, or they may have been induced by a common component of both the broccoli-rich and pea-rich diet. To our knowledge there is no data on the rate of change on androgen signalling in men of this age with HGPIN. This observation suggests further study is warranted. Analysis of the rate of change of gene expression of men diagnosed with either HGPIN or localized prostate cancer through sequential biopsies may provide reliable biomarkers to measure the likelihood of both carcinogenesis and progression to aggressive cancer, and complement histological examination of needle biopsies and measurement of plasma PSA levels. Secondly, stratification of global gene expression profiles by genotype has been informative, and this approach could be extended to other genes to dissect patterns of gene expression in prostate or other tissues. Lastly, it is conceivable that other dietary phytochemicals, such as polyphenolic derivatives, could also chemically interact with signalling peptides in the plasma, in a similar manner to the suggested mechanism of action of isothiocyanates.

In conclusion, we consider that our study has provided a mechanistic basis for the reduction in risk of prostate cancer through broccoli consumption, as suggested by epidemiological studies.

Volunteers were randomly assigned to either a broccoli-rich or a pea-rich diet. After six months there were no differences in gene expression between glutathione S-transferase mu 1 (GSTM1) positive and null individuals on the pea-rich diet but significant differences between GSTM1 genotypes on the broccoli-rich diet, associated with transforming growth factor beta 1 (TGFβ1) and epidermal growth factor (EGF) signalling pathways. Comparison of biopsies obtained pre and post intervention revealed more changes in gene expression occurred in individuals on a broccoli-rich diet than in those on a pea-rich diet. While there were changes in androgen signalling, regardless of diet, men on the broccoli diet had additional changes to mRNA processing, and TGFβ1, EGF and insulin signalling. We also provide evidence that sulforaphane (the isothiocyanate derived from 4-methylsuphinylbutyl glucosinolate that accumulates in broccoli) chemically interacts with TGFβ1, EGF and insulin peptides to form thioureas, and enhances TGFβ1/Smad-mediated transcription.

CONCLUSIONS

The findings presented herein suggest that consuming broccoli interacts with GSTM1 genotype to result in complex changes to signalling pathways associated with inflammation and carcinogenesis in the prostate. We propose that these changes may be mediated through the chemical interaction of isothiocyanates with signalling peptides in the plasma. This study provides, for the first time, experimental evidence obtained in humans to support observational studies that diets rich in cruciferous vegetables may reduce the risk of prostate cancer and other chronic disease.

TABLE 1

Volunteer characteristics and plasma PSA levels.

| Age | BMI | GSTM1 | PSA (ng/ml) Pre-intervention | 6-month | 12-month |
|---|---|---|---|---|---|
| | | | Broccoli intervention | | |
| 68 | 29 | null | 4.6 | 5.4 | 5.3 |
| 68 | 27 | null | 3.1 | 3.2 | 2.9 |
| 64 | 26 | null | 9.4 | 3.5 | 2.9 |

TABLE 1-continued

Volunteer characteristics and plasma PSA levels.

| Age | BMI | GSTM1 | PSA (ng/ml) Pre-intervention | 6-month | 12-month |
|---|---|---|---|---|---|
| 63 | 31 | null | 6.5 | 7.9 | 7.2 |
| 66 | 28 | null | 0.9 | 1.3 | 0.9 |
|  |  | Mean | 4.9 | 4.3 | 3.84 |
|  |  | (sd) | (3.25) | (2.50) | (2.44) |
| 57 | 27 | positive | 5.5 | 5.5 | 5.7 |
| 66 | 30 | positive | 13.6 | 16.8 | 13.4 |
| 69 | 27 | positive | 6.9 | 3.8 | 3.7 |
| 62 | 23 | positive | 2.2 | 2.2 | 1.9 |
| 59 | 29 | positive | 10.8 | 10.4 | 11.2 |
| 68 | 25 | positive | 9.7 | 12.5 | 7.2 |
| 64 | 32 | positive | 6.4 | 6.1 | 6.6 |
| 63 | 27 | positive | 7.9 | 9 | 10.8 |
|  |  | Mean | 7.9 | 8.3 | 7.56 |
|  |  | (sd) | (3.5) | (4.85) | (3.95) |
| *Peas intervention* | | | | | |
| 70 | 28 | null | 4.1 | 4.2 | 4.4 |
| 65 | 24 | null | 7.5 | 9.3 | 8.2 |
| 59 | 24 | null | 9.3 | 10.8 | 8 |
| 61 | 35 | null | 1.1 | 1.1 | 1.1 |
| 57 | 26 | null | 5.5 | 5.4 | 5.2 |
|  |  | Mean | 5.5 | 6.2 | 5.4 |
|  |  | (sd) | (3.15) | (3.92) | (2.92) |
| 70 | 23 | positive | 8.9 | 5.2 | N/A* |
| 61 | 29 | positive | 2.3 | 2.2 | 2.5 |
| 57 | 30 | positive | 3.5 | 5.5 | 4.9 |
|  |  | Mean | 4.9 | 4.3 | 3.7 |
|  |  | (sd) | (3.52) | (1.82) | (1.70) |

One of the 22 volunteers was diagnosed with prostatic adenocarcinoma at the study baseline biopsy (pre-intervention) and was removed from the study.
*This volunteer developed prostatic adenocarcinoma six months into the intervention and was removed from the study.

TABLE 2

Pathway analyses of prostate biopsy tissue.

| Pathway | Genes changed/ Genes on MAPP | Adjusted P-value* |
|---|---|---|
| a. Benign compared with malignant TURP tissue | | |
| Focal adhesion | 57/187 | <0.001 |
| TGFβ receptor | 47/151 | 0.002 |
| Circadian exercise | 20/48 | 0.006 |
| Fatty acid metabolism | 24/80 | 0.012 |
| Prostaglandin synthesis regulation | 14/31 | 0.026 |
| Actin binding | 53/213 | 0.028 |
| GPCRs Class A rhodopsin-like | 15/262 | 0.05 |
| b. GSTM1 positives compared with GSTM1 nulls post six month broccoli intervention | | |
| EGFR1 | 76/177 | <0.001 |
| Adipogenesis | 52/130 | 0.026 |
| TGF-beta receptor | 58/151 | 0.039 |
| c. Paired samples pre and post 12 month dietary intervention | | |
| *0-12 month peas* | | |
| Androgen receptor | 18/112 | 0.042 |
| *0-12 month broccoli ** * | | |
| mRNA processing | 40/125 | <0.001 |
| Androgen receptor | 33/112 | <0.001 |
| TGFβ receptor | 39/151 | 0.004 |
| Insulin signalling | 38/159 | 0.014 |
| Delta-notch | 24/85 | 0.019 |
| Wnt signalling | 28/109 | 0.02 |

TABLE 2-continued

Pathway analyses of prostate biopsy tissue.

| Pathway | Genes changed/ Genes on MAPP | Adjusted P-value* |
|---|---|---|
| EGFR1 | 40/177 | 0.02 |
| IL-2 | 21/76 | 0.036 |

EGFR, epidermal growth factor receptor; GPCRs, G-protein coupled receptors; IL-2, interleukin 2; TGFβ, transforming growth factor beta; TURP, transurethral resection of the prostate; Wnt, wingless-type MMTV integration site. Pathways in GenMAPP that are enriched in the gene lists that differentiate groups are shown. Only pathways with adjusted P values ≤0.05 are shown. Also, the number of genes changing between groups that belong to these pathways is shown alongside the total number of genes that constitute the pathway. Pathway analysis was performed on gene lists generated in dChip that were statistically significant (P ≤ 0.05, Welch modified two-sample paired or unpaired t-test) between the two groups. No fold cutoff was used. For details on gene lists see Table 3.
*P-values were calculated in GenMAPP using a non-parametric statistic based on 2000 permutations of the data and further adjusted for multiple testing by Westfall-Young adjustment.
** GSTM1 positive volunteers, n = 4.

TABLE 3

Differentially expressed probes in prostate tissue.

| | Fold change | P <0.05* | P <0.005* | P <0.0005* |
|---|---|---|---|---|
| (a) Differences between benign and malignant TURP tissue | | | | |
| Benign v Malignant | >1.0 | 3810 (353) | 683 (7) | 124 (0) |
|  | >1.5 | 1081 (59) | 400 (2) | 104 (0) |
|  | >2.0 | 277 (7) | 140 (0) | 54 (0) |
| (b) Differences between GSTM1 positive and null genotypes | | | | |
| Benign (TURP) | >1.0 | 661 (538) | 19 (17) | 0 (0) |
|  | >1.5 | 160 (186) | 7 (14) | 0 (0) |
|  | >2.0 | 50 (40) | 1 (3) | 0 (0) |
| Malignant (TURP) | >1.0 | 686 (431) | 8 (13) | 0 (0) |
|  | >1.5 | 244 (152) | 4 (8) | 0 (0) |
|  | >2.0 | 44 (33) | 1 (3) | 0 (0) |
| Pre-intervention | >1.0 | 730 (484) | 26 (9) | 0 (0) |
|  | >1.5 | 252 (79) | 16 (3) | 0 (0) |
|  | >2.0 | 43 (9) | 8 (1) | 0 (0) |
| 6 month broccoli | >1.0 | 7976 (351) | 434 (4) | 17 (0) |
|  | >1.5 | 2790 (91) | 268 (2) | 14 (0) |
|  | >2.0 | 316 (8) | 31 (0) | 1 (0) |
| 6 month peas | >1.0 | 220 (220) | 6 (4) | 0 (0) |
|  | >1.5 | 33 (41) | 5 (3) | 0 (0) |
|  | >2.0 | 5 (10) | 1 (1) | 0 (0) |
| (c) Differences between paired samples | | | | |
| 0-12 months broccoli | >1.0 | 2857 (96) | 151 (0) | 1 (0) |
|  | >1.5 | 1243 (12) | 141 (0) | 1 (0) |
|  | >2.0 | 213 (0) | 62 (0) | 1 (0) |
| 0-12 months peas | >1.0 | 1199 (42) | 19 (0) | 0 (0) |
|  | >1.5 | 495 (18) | 19 (0) | 0 (0) |
|  | >2.0 | 81 (1) | 4 (0) | 0 (0) |

Probe numbers that have satisfied the comparison criteria of fold change and P-value cutoffs are shown. Numbers in parentheses represent the median false discovery rate calculated in dChip after 100 permutations of the samples.
*P-values were calculated in dChip by a Welch modified two-sample t-test. n = 18 for Benign, n = 14 for Malignant; n = 4 for GSTM1(+) Benign, n = 14 for GSTM1(−) Benign; n = 5 for GSTM1(+) Malignant, n = 9 for GSTM1(−) Malignant; n = 7 for GSTM1(+) Pre-intervention, n = 3 for GSTM1(−) Pre-intervention; n = 6 for GSTM1(+) 6-month broccoli, n = 5 for GSTM1(−) 6-month broccoli; n = 3 for GSTM1(+) 6-month pea and n = 5 for GSTM1(−) 6-month pea intervention.
**P-values were calculated in dChip by a Welch modified two-sample paired t-test, n = 4 for each of the diet interventions.

TABLE 4

Dietary analysis of average daily intakes of nutrients.

| Variable | Baseline | 6 months | P-value* |
|---|---|---|---|
| Pea-rich diet (n = 7) | | | |
| Fat (g) | 93.76 (32.97) | 90.99 (25.83) | 0.831 |
| Protein (g) | 87.50 (15.15) | 95.77 (33.31) | 0.526 |
| CHO (g) | 240.04 (79.85) | 242.94 (72.97) | 0.872 |
| Energy (KJ) | 9081.88 (2480.80) | 9506.00 (2405.38) | 0.738 |
| Alcohol (g) | 12.65 (9.87) | 25.07 (35.42) | 0.415 |
| Cholesterol (mg) | 353.57 (74.43) | 345.29 (201.06) | 0.930 |
| Vitamin C (mg) | 81.00 (66.05) | 79.43 (62.58) | 0.846 |
| Vitamin E (mg) | 8.24 (5.64) | 7.15 (3.60) | 0.395 |
| Vitamin D (µg) | 3.77 (3.25) | 3.84 (1.76) | 0.949 |
| β-Carotene (mg) | 1.94 (1.57) | 3.22 (2.29) | 0.184 |
| Folate (1.1 µg) | 261.00 (89.36) | 332.86 (214.50) | 0.489 |
| Iron (mg) | 11.73 (4.36) | 13.32 (4.92) | 0.555 |
| Selenium (µg) | 50.14 (13.01) | 49.14 (23.08) | 0.923 |
| Peas (g) | 8.57 (10.23) | 57.41 (18.86) | 0.001 |
| Broccoli (g) | 18.49 (30.89) | 9.90 (13.61) | 0.431 |
| Estimated GSL (µmol) | 9.36 (15.63) | 5.01 (6.88) | 0.431 |
| Broccoli-rich diet (n = 11) | | | |
| Fat (g) | 90.93 (29.27) | 91.57 (33.70) | 0.929 |
| Protein (g) | 96.99 (20.02) | 96.97 (21.26) | 0.996 |
| CHO (g) | 276.28 (76.03) | 296.18 (72.99) | 0.305 |
| Energy (KJ) | 9633.45 (2311.35) | 9980.73 (2286.62) | 0.488 |
| Alcohol (g) | 9.75 (7.20) | 10.48 (9.70) | 0.841 |
| Cholesterol (mg) | 337.27 (168.29) | 298.46 (123.99) | 0.211 |
| Vitamin C (mg) | 262.55 (175.83) | 303.00 (188.52) | 0.590 |
| Vitamin E (mg) | 11.31 (5.73) | 11.14 (4.82) | 0.924 |
| Vitamin D (ug) | 5.22 (3.17) | 3.65 (1.08) | 0.076 |
| Beta Carotene (mg) | 4.07 (3.01) | 3.63 (2.53) | 0.667 |
| Folate (µg) | 477.82 (188.20) | 491.36 (193.47) | 0.762 |
| Iron (mg) | 14.29 (2.09) | 14.09 (2.25) | 0.916 |
| Selenium (µg) | 77.09 (29.89) | 68.82 (26.22) | 0.304 |
| Peas (g) | 4.16 (5.51) | 7.60 (8.46) | 0.227 |
| Broccoli (g) | 25.89 (24.49) | 55.84 (7.71) | 0.002 |
| Estimated GSL (µmol) | 13.10 (12.39) | 79.30 (10.94) | <0.0001 |

Variables shown are given in mean (sd) units per day. GSL refers to the glucosinolate precursors of sulforaphane and iberin (i.e. 4-methylsulphinylbutyl and 3-methylsulphinylpropyl glucosinolate respectively). Similar analysis between GSTM1 positive and null individuals showed no difference in dietary intakes after 6 months within either broccoli-rich or pea-rich intervention.
*P-values were calculated in Minitab using a paired t-test.

Example 3

Growth factors interact with receptors on the cell surface to affect gene and protein regulation, and thus cell proliferation within the cell via cell signalling pathways. One important cell signalling pathway is known as PI3K/pAKT signalling. In this pathway, growth factors such as insulin, EGF and TGFβ interact with cell surface receptors resulting in the phosphorylation of a protein know as AKT. Activation of this pathway plays a vital role in cell survival by stimulating metabolism, protein synthesis, DNA synthesis and cell proliferation, and inhibiting apoptosis. The extent of activation is normally limited by the PTEN protein that attenuates phosphorylation of AKT. In many cancers, PTEN is either mutated so that there is constitutive activation of AKT leading to rapid cell proliferation and tumour formation. Inhibiting pAKT signalling is a major target of the pharmaceutical industry. Loss of PTEN occurs in up to 60% of metastatic prostate cancers.

There is a link between pAKT and tumour genesis.

The activation of pAKT can be observed in the prostate cancer cell line PC-3 by western blotting (see FIG. 19). This is partially because PC-3 cells are very sensitive to growth factors that are present in the fetal calf serum (FCS), which is part of the normal culture medium, due to a lack of a functional PTEN gene to attenuate phosphorylation of AKT. In contrast, in the non cancer cell line BPH-1, which possesses a functional PTEN gene, phosphorylation of AKT only occurs following exposure to additional growth factors such as insulin or EGF (see FIG. 18).

Incubating PC-3 cells with SF for one hour reduces pAKT expression (FIG. 19)—particularly at the dosage levels of 2 µM. The data for PC3 cells+SF+FCS (fetal calf serum) shows in the control (without SF) constitutive expression of pAKT. Addition of 2 µM SF suppresses pAKT, while there is a variable response at 10 µM. The inventors have also seen suppression at 0.5 µM (data not shown).

The suppression of pAKT is lost at higher concentrations, when there would be considerable disruption.

If PC-3 cells are grown in culture medium without FCS, there is still pAKT expression, although at a reduced level (see FIG. 20), but there is no further inhibition by the addition of SF. This suggests that SF may be interacting with the growth factors in the FCS to prevent further phosphorylation of AKT, as opposed to acting within the cell.

Therefore, the conjugation between isothiocyanates and several important growth factors leads to inhibition of the growth factors may be associated with anticarcinogen activity particularly in tissues in which there has been a mutation in the PTEN gene leading to hyperactivation of pAKT-mediated signalling, which is associated with cell proliferation and tumour growth.

Western Blotting

BPH-1 or PC-3 cells were cultured in 10 cm cell culture dishes or 6-well culture plates until they reached 80% confluency and were lifter using TE buffer (10 mM Tris/HCl, 1 mM EDTA, pH8). After 24 h treatment with SF cells were washed three times with cold PBS and treated with RIPA buffer for 2 min on ice, followed by centrifugation at 13 000 g at 4° C. for 10 min and the supernatant collected for western blotting. Protein was separated on NuPage 10% polyacrylamide gels by electrophoresis and transferred to nitrocellulose membranes. Membranes were probed with primary antibodies obtained from Cell Signalling© at a dilution of 1:1000: Phospho-Akt (Ser$^{473}$) Rabbit mAb (#4060 L) and AKT (pan) Rabbit mAb (#4685). GAPDH was used as a loading control for all blots. Proteins were visualised with SuperSignal West Chemiluminescence kit.

FIG. 21 shows the results of the western blot. A: Immunohistochemistry of PC-3 cells showing pAKT expression (red colouration). B: Immunohistochemistry of PC-3 cells following incubation in 2 µM SF for 1 h showing inhibition of pAKT expression.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

1. Allender, S., et al. *Coronary heart disease statistics*. 2008 [cited 2009 Jul. 15, 2009]; Available from: www.heartstats.org.

2. *Coronary heart disease*. Health care 2009 [cited 2009 May 6, 2009]; Available from: http//www.dh.gov.uk/en/Healthcare/National ServiceFrameworks/Coronaryheartdisease/.
3. Schaefer, E. J., *Lipoproteins, nutrition, and heart disease*. Am. J. Clin Nutr, 2002. 75(2): p. 191-212.
4. Libby, P. and P. M. Ridker, *Novel inflammatory markers of coronary risk: theory versus practice*. Circulation, 1999. 100(11): p. 1148-50.
5. Plutzky, J., *Inflammatory pathways in atherosclerosis and acute coronary syndromes*. Am J Cardiol, 2001. 88(8A): p. 10K-15K.
6. Ross, R., *Atherosclerosis is an inflammatory disease*. Am Heart J, 1999. 138(5 Pt 2): p. S419-20.
7. Tracy, R. P., *Inflammation in cardiovascular disease: cart, horse, or both?* Circulation, 1998. 97(20): p. 2000-2.
8. Lampe, J. W., *Health effects of vegetables and fruit: assessing mechanisms of action in human experimental studies*. Am J Clin Nutr, 1999. 70(3 Suppl): p. 475S-490S.
9. Barberger-Gateau, P., et al., *Fish, meat, and risk of dementia: cohort study*. BMJ, 2002. 325(7370): p. 932-3.
10. Kalmijn, S., et al., *Dietary fat intake and the risk of incident dementia in the Rotterdam Study*. Ann Neurol, 1997. 42(5): p. 776-82.
11. Morris, M. C., et al., *Consumption of fish and n-3 fatty acids and risk of incident Alzheimer disease*. Arch Neurol, 2003. 60(7): p. 940-6.
12. Ambrosone, C. B., et al., *Breast cancer risk in premenopausal women is inversely associated with consumption of broccoli, a source of isothiocyanates, but is not modified by GST genotype*. J Nutr, 2004. 134(5): p. 1134-8.
13. Feskanich, D., et al., *Prospective study of fruit and vegetable consumption and risk of lung cancer among men and women*. J Natl Cancer Inst, 2000. 92(22): p. 1812-23.
14. Fowke, J. H., et al., *Urinary isothiocyanate levels, brassica, and human breast cancer*. Cancer Res, 2003. 63(14): p. 3980-6.
15. Miller, A. B., et al., *Fruits and vegetables and lung cancer: Findings from the European Prospective Investigation into Cancer and Nutrition*. Int J Cancer, 2004. 108(2): p. 269-76.
16. Neuhouser, M. L., et al., *Fruits and vegetables are associated with lower lung cancer risk only in the placebo arm of the beta-carotene and retinol efficacy trial (CARET)*. Cancer Epidemiol Biomarkers Prev, 2003. 12(4): p. 350-8.
17. Verhoeven, D. T., et al., *Epidemiological studies on brassica vegetables and cancer risk*. Cancer Epidemiol Biomarkers Prev, 1996. 5(9): p. 733-48.
18. Voorrips, L. E., et al., *Vegetable and fruit consumption and risks of colon and rectal cancer in a prospective cohort study: The Netherlands Cohort Study on Diet and Cancer*. Am J Epidemiol, 2000. 152(11): p. 1081-92.
19. Milner, J. A., *Molecular targets for bioactive food components*. J Nutr, 2004. 134(9): p. 2492S-2498S.
20. Surh, Y. J., *Cancer chemoprevention with dietary phytochemicals*. Nat Rev Cancer, 2003. 3(10): p. 768-80.
21. Cornelis, M. C., A. El-Sohemy, and H. Campos, *GSTT1 genotype modifies the association between cruciferous vegetable intake and the risk of myocardial infarction*. Am J Clin Nutr, 2007. 86(3): p. 752-8.
22. Law, M. R., N. J. Wald, and S. G. Thompson, *By how much and how quickly does reduction in serum cholesterol concentration lower risk of ischaemic heart disease?* BMJ, 1994. 308(6925): p. 367-72.
23. Mirmiran, P., et al., *Fruit and vegetable consumption and risk factors for cardiovascular disease*. Metabolism, 2009. 58(4): p. 460-8.
24. Suido, H., et al., *A mixed green vegetable and fruit beverage decreased the serum level of low-density lipoprotein cholesterol in hypercholesterolemic patients*. J Agric Food Chem, 2002. 50(11): p. 3346-50.
25. Takai, M., et al., *[LDL-cholesterol-lowering effect of a mixed green vegetable and fruit beverage containing broccoli and cabbage in hypercholesterolemic subjects]*. Rinsho Byori, 2003. 51(11): p. 1073-83.
26. Tucker, K. L., et al., *Dietary intake pattern relates to plasma folate and homocysteine concentrations in the Framingham Heart Study*. J Nutr, 1996. 126(12): p. 3025-31.
27. Ganji, V. and M. R. Kafai, *Frequent consumption of milk, yogurt, cold breakfast cereals, peppers, and cruciferous vegetables and intakes of dietary folate and riboflavin but not vitamins B-12 and B-6 are inversely associated with serum total homocysteine concentrations in the US population*. Am J Clin Nutr, 2004. 80(6): p. 1500-7.
28. Nettleton, J A., et al., *Dietary patterns are associated with biochemical markers of inflammation and endothelial activation in the Multi-Ethnic Study of Atherosclerosis (MESA)*. Am J Clin Nutr, 2006. 83(6): p. 1369-79.
29. Wu, L. and B. H. Juurlink, *The impaired glutathione system and its up-regulation by sulforaphane in vascular smooth muscle cells from spontaneously hypertensive rats*. J Hypertens, 2001. 19(10): p. 1819-25.
30. Wu, L., et al., *Dietary approach to attenuate oxidative stress, hypertension, and inflammation in the cardiovascular system*. Proc Natl Acad Sci USA, 2004. 101(18): p. 7094-9.
31. Kim, S. Y., et al., *Kale juice improves coronary artery disease risk factors in hypercholesterolemic men*. Biomed Environ Sci, 2008. 21(2): p. 91-7.
32. Murashima, M., et al., *Phase I study of multiple biomarkers for metabolism and oxidative stress after one-week intake of broccoli sprouts*. Biofactors, 2004. 22(1-4): p. 271-5.
33. Yochum, L., et al., *Dietary flavonoid intake and risk of cardiovascular disease in postmenopausal women*. Am J Epidemiol, 1999. 149(10): p. 943-9.
34. van Poppel, G., et al., *Brassica vegetables and cancer prevention. Epidemiology and mechanisms*. Adv Exp Med Biol, 1999. 472: p. 159-68.
35. Conaway, C. C., et al., *Disposition of glucosinolates and sulforaphane in humans after ingestion of steamed and fresh broccoli*. Nutr Cancer, 2000. 38(2): p. 168-78.
36. Steinmetz, K. A. and J. D. Potter, *Vegetables, fruit, and cancer. II. Mechanisms*. Cancer Causes Control, 1991. 2(6): p. 427-42.
37. Steinmetz, K. A. and J. D. Potter, *Vegetables, fruit, and cancer. I. Epidemiology*. Cancer Causes Control, 1991. 2(5): p. 325-57.
38. Sarikamis, G., et al., *High glucosinolate broccoli: a delivery system for sulforaphane*. Molecular Breeding, 2006. 18(3): p. 219-228.
39. Mithen, R., et al., *Development of isothiocyanate-enriched broccoli, and its enhanced ability to induce phase 2 detoxification enzymes in mammalian cells*. Theoretical and Applied Genetics, 2003. 106(4): p. 727-734.
40. Gasper, A. V., et al., *Glutathione S-transferase M1 polymorphism and metabolism of sulforaphane from standard and high-glucosinolate broccoli*. Am J Clin Nutr, 2005. 82(6): p. 1283-91.
41. Traka, M., et al., *Broccoli consumption interacts with GSTMJ to perturb oncogenic signalling pathways in the prostate*. PLoS ONE, 2008. 3(7): p. e2568.

42. Awasthi, Y., R. Sharma, and S. Singhal, *Human glutathione S-transferases.* Int J Biochem, 1994. 26: p. 295-305.
43. Ryberg, D., et al., *Genotypes of glutathione transferase M1 and P1 and their significance for lung DNA adduct levels and cancer risk.* Carcinogenesis, 1997. 18(7): p. 1285-9.
44. Lakatta, E., et al., *Human aging: changes in structure and function.* J Am Coll Cardiol., 1987. 1987(10 (suppl A)): p. 42A-47A.
45. Sutton-Tyrrell, K., et al., *Aortic stiffness is associated with visceral adiposity in older adults enrolled in the study of health, aging, and body composition.* Hypertension, 2001. 38(3): p. 429-33.
46. Laurent, S., et al., *Aortic stiffness is an independent predictor of all-cause and cardiovascular mortality in hypertensive patients.* Hypertension, 2001. 37(5): p. 1236-41.
47. Weber, T., et al., *Arterial stiffness, wave reflections, and the risk of coronary artery disease.* Circulation, 2004. 109: p. 184-189.
48. Blacher, J., et al., *Aortic pulse wave velocity as a marker of cardiovascular risk in hypertensive patients.* Hypertension, 1999. 33(5): p. 1111-7.
49. Blacher, J., et al., *Impact of aortic stiffness on survival in end-stage renal disease.* Circulation. 1999. 99(18): p. 2434-9.
50. Laurent, S, and P. Boutouyrie, *Arterial stiffness: a new surrogate end point for cardiovascular disease?* J Nephrol, 2007. 20 Suppl 12: p. S45-50.
51. O'Brien, E., et al., *Use and interpretation of ambulatory blood pressure monitoring: recommendations of the British hypertension society.* BMJ, 2000. 320(7242): p. 1128-34.
52. Laurent, S., et al., *Expert consensus document on arterial stiffness: methodological issues and clinical applications.* Eur Heart J, 2006. 27(21): p. 2588-605.
53. Kelly, R. P., R. Tunin, and D. A. Kass, *Effect of reduced aortic compliance on cardiac efficiency and contractile function of in situ canine left ventricle.* Circ. Res, 1992. 71: p. 490-502.
54. Ohtsuka, S., et al., *Chronically decreased aortic distensibility causes deterioration of coronary perfusion during increased left ventricular contractility.* J. Am. Coll. Cardiol, 1994. 24: p. 1406-1414.
55. Smulyan, H. and M. E. Safar, *Systolic blood pressure revisited.* J. Am. Coll. Cardiol, 1997. 29: p. 1407-1413.
56. Rajkumar, C., et al., *Hormonal therapy improves arterial compliance in post menopausal women.* J. Am. Coll. Cardiol, 1997. 39: p. 350-356.
57. Nichols WlW and O. R. M F., *Theoretical, experimental and clinical principles.* McDonald's Blood Flow in Arteries 1998, London: Arnold.
58. Wood, D. A., et al., *JBS2: Joint British guidelines on prevention of cardiovascular disease in clinical practice.* Heart, 2005. 91(Suppl V): p. V1-52.
59. Wilson, P. W., et al., *Prediction of coronary heart disease using risk factor categories.* Circulation, 1998. 97(18): p. 1837-47.
60. Taves, D. R., *Minimization: a new method of assigning patients to treatment and control groups.* Clin Pharmacol Ther, 1974. 15(5): p. 443-53.
61. Jacobs, D. R., Jr., et al., *High density lipoprotein cholesterol as a predictor of cardiovascular disease mortality in men and women: the follow-up study of the Lipid Research Clinics Prevalence Study.* Am J Epidemiol, 1990. 131(1): p. 32-47.
62. Wald, N. J. and M. R. Law, *Serum cholesterol and ischaemic heart disease.* Atherosclerosis, 1995. 118 Suppl: p. S1-5.
63. Werner, R. M. and T. A. Pearson, *LDL-cholesterol: a risk factor for coronary artery disease-from epidemiology to clinical trials.* Can J Cardiol, 1998. 14 Suppl B: p. 3B-10B.
64. Hutton, J., et al., *Cardiovascular Disease in England: Opportunities and Challenges Over the Next Ten Years.* Cardio and vascular coalition, ed. C.D.i. England. 2008, York: York Health Economic Consortium, University of York.
65. Uren, N. and S. Collins. *High cholesterol level (hypercholesterolaemia).* 2008 Jul. 4, 2008 [cited 2009 May 19, 2009]; Available from: http://www.netdoctor.co.uk/diseases/facts/hypercholesterolemia.htm.
66. Williams, B., et al., *British Hypertension Society guidelines for hypertension management 2004 (BHS-IV): summary.* BMJ, 2004. 328(7440): p. 634-40.
67. Kang, M., B. G. Ragan, and J. H. Park, *Issues in outcomes research: an overview of randomization techniques for clinical trials.* J Athl Train, 2008. 43(2): p. 215-21.
68. Khoshdel, A. R., et al., *Better management of cardiovascular diseases by pulse wave velocity: combining clinical practice with clinical research using evidence-based medicine.* Clin Med Res, 2007. 5(1): p. 45-52.
69. Boutouyrie, P., S. Laurent, and M. Briet, *Importance of arterial stiffness as cardiovascular risk factor for future development of new type of drugs.* Fundam Clin Pharmacol, 2008. 22(3): p. 241-6.
70. Asmar., R., ed. *Arterial Stiffness and Pulse Wave Velocity: Clinical Applications.* ed. E.s.e. medicals. 1999, Elsevier SAS: Paris.
71. White, W., *Importance of aggressive blood pressure lowering when it may matter most.* Am J. Cardiol., 2007. 100(3A): p. 10J-16J.
72. Clement, D., M. De Buyzere, and D. De Bacquer, et al., *Prognostic value of ambulatory blood-pressure recordings in patients with treated hypertension.* N Engl J Med, 2003. 348(24): p. 2407-15.
73. McGrath, B., *Ambulatory blood pressure monitoring.* Med J Aust, 2002. 176(12): p. 588-92.
74. Ross, R., *Atherosclerosis—an inflammatory disease.* N Engl J Med, 1999. 340(2): p. 115-26.
75. Yudkin, J. S., and et al., *C-reactive protein in healthy subjects: associations with obesity, insulin resistance, and endothelial dysfunction: a potential role for cytokines originating from adipose tissue?* Arterioscler Thromb Vasc Biol, 1999. 19(4): p. 972-8.
76. Ershler, W. B., W. H. Sun, and N. Binkley, *The role of interleukin-6 in certain age-related diseases.* Drugs Aging, 1994. 5(5): p. 358-65.
77. Volpato, S., et al., *Cardiovascular disease, interleukin-6, and risk of mortality in older women: the women's health and aging study.* Circulation, 2001. 103(7): p. 947-53.
78. Ridker, P. M., *Clinical application of C-reactive protein for cardiovascular disease detection and prevention.* Circulation, 2003. 107(3): p. 363-9.
79. Pepys, M. B. and G. M. Hirschfield, *C-reactive protein: a critical update.* J Clin Invest, 2003. 111(12): p. 1805-12.
80. Zittermann, A., *Vitamin D and disease prevention with special reference to cardiovascular disease.* Prog Biophys Mol Biol, 2006. 92(1): p. 39-48.
81. Holick, M. F., *Vitamin D deficiency.* N Engl J Med, 2007. 357(3): p. 266-81.
82. Lee, J. H., et al., *Vitamin D deficiency an important, common, and easily treatable cardiovascular risk factor?* J Am Coll. Cardiol, 2008. 52(24): p. 1949-56.

83. (online), U.D.o.H.a.H.S, *National Health and Nutrition Examination Survey Data.* National Centre for Health statistics [cited 2009 Jul. 9, 2009]; Available from: http://www.cdc.gov/nchs/nhanes.htm.
84. Martins, D., et al., *Prevalence of cardiovascular risk factors and the serum levels of 25-hydroxyvitamin D in the United States: data from the Third National Health and Nutrition Examination Survey.* Arch Intern Med, 2007. 167(11): p. 1159-65.
85. Wang, T. J., et al., *Vitamin D deficiency and risk of cardiovascular disease.* Circulation, 2008. 117(4): p. 503-11.
86. Stroewsand, G., *Bioactive Organosulfur Phytochemical in Brassica oleracea Vegetables—A review.* Food Chemistry Toxicology, 1995. 33: p. 537-543.

The invention claimed is:

1. A method for the treatment of a cardiovascular disease (CVD) or for the promotion of heart and/or cardiovascular health in a human which method comprises administering to a subject an effective amount of a Cruciferous vegetable having a glucosinolate and/or at least one derivative thereof in an amount of at least 20 µ moles/g dry weight, wherein the administration reduces the CVD risk in the subject, wherein said subjects are defined as those whose 10 year CVD risk exceeds 20%, and wherein the Cruciferous vegetable is broccoli.

2. A method according to claim 1 wherein said Cruciferous vegetable having a high level of glucosinolate and/or at least one derivative thereof is provided in a set dietary regimen at an adequate dosage to achieve a desired physiological effect.

3. A method according to claim 1 wherein the glucosinolate and/or at least one derivative thereof is selected from at least one of: 4-methylsulphinylbutyl glucosinolate, 3-methylsulphinylpropyl glucosinolate, 4-methylthiobutyl glucosinolate, 3-methylthiopropyl glucosinolate, sulforaphane, erucin, sativin, iberin, β-phenylethylisothiocyanate (PE-ITC), 3-methylthiopropyl isothiocyanate.

4. A method according to claim 1 wherein the method is for the treatment or prevention of one or more of the following: angina, artherosclerosis, cardiomyopathy or cardiac inflammation, congestive heart failure, coronary artery disease, carotid artery disease, heart attack (coronary thrombosis, myocardial infarction), peripheral artery disease, stroke.

5. A method according to claim 1 wherein the method is for the treatment of one or more cardiovascular risk factors.

6. A method according to claim 5 wherein the cardiovascular risk factor is one or more of the following hypertension or hypercholesterolemia.

7. A method according to claim 1, for improving or controlling one or more of the level of LDL cholesterol, the level HDL cholesterol, the level total cholesterol, the level of vitamin D, the level of hsCRP, the level of IL-6, blood pressure, arterial stiffness, AIx measurement and/or PWV measurement in the subject.

8. A method according to claim 7 for improving or controlling the level of serum cholesterols.

9. A method according to claim 8 wherein the level of total cholesterol (TC) and LDL-cholesterol is lowered or prevented from increasing compared with the level in a subject not treated with said Cruciferous vegetable.

10. A method for improving or controlling the level of mammalian serum cholesterols, or for treating hypercholesterolemia, or for treating hypertension in a human said method comprising consuming an effective amount of a Cruciferous vegetable having a glucosinolate and/or at least one derivative thereof in an amount of at least 20 µmoles/g dry weight, wherein the Cruciferous vegetable is broccoli.

11. The method of claim 10, wherein one or more extracellular signalling proteins are covalently modified.

12. The method of claim 10, wherein the level of total cholesterol (TC) and LDL-cholesterol is lowered or prevented from increasing.

13. The method of claim 1 or 10 wherein the broccoli has a level of glucosinolate which is 2 to 3 times the level found in a standard broccoli grown under similar conditions.

14. The method according to claim 1 or claim 10, wherein the high glucosinolate Cruciferous vegetable has a level of glucosinolate which is 2 to 3 times the level found in a standard Cruciferous vegetable grown under similar conditions.

* * * * *

UNITED STATES PATENT AND TRADEMARK OFFICE
CERTIFICATE OF CORRECTION

PATENT NO.        : 9,023,811 B2                              Page 1 of 1
APPLICATION NO.   : 13/518777
DATED             : May 5, 2015
INVENTOR(S)       : Mithen It is certified that error appears in the above-identified patent and that said Letters Patent is hereby corrected as shown below:

Title Page:

At item (87), line 2, "Mar. 30, 2011" should be -- June 30, 2011 --.

In the Claims:

At Column 49, line 41, "treatment or prevention of" should be -- treatment of --.

At Column 49, line 42, "atherosclerosis," should be -- atherosclerosis --.

At Column 50, line 34, "μmoles/g" should be -- μ moles/g --.

At Column 50, line 43, "conditions." should be -- conditions, and is at least 20 μ moles/g dry weight. --.

At Column 50, line 44, "claim 1 or claim 10," should be -- claim 1 or 10, --.

At Column 50, lines 47-48, "conditions." should be -- conditions, and is at least 20 μ moles/g dry weight. --.

Signed and Sealed this
Twenty-third Day of February, 2016

Michelle K. Lee
*Director of the United States Patent and Trademark Office*

UNITED STATES PATENT AND TRADEMARK OFFICE
CERTIFICATE OF CORRECTION

PATENT NO. : 9,023,811 B2  
APPLICATION NO. : 13/518777  
DATED : May 5, 2015  
INVENTOR(S) : Mithen Page 1 of 1

It is certified that error appears in the above-identified patent and that said Letters Patent is hereby corrected as shown below:

Title page, Item (54) and in the Specification, line 7, "GLUSOSINOLATES" should be --GLUCOSINOLATES--.

Signed and Sealed this  
Twenty-second Day of March, 2016

Michelle K. Lee  
*Director of the United States Patent and Trademark Office*

SEQUENCE LISTING

```
<160> NUMBER OF SEQ ID NOS: 7

<210> SEQ ID NO 1
<211> LENGTH: 13
<212> TYPE: PRT
<213> ORGANISM: Homo sapiens

<400> SEQUENCE: 1

Ala Leu Asp Thr Asn Tyr Cys Phe Ser Ser Thr Glu Lys
1               5                   10

<210> SEQ ID NO 2
<211> LENGTH: 24
<212> TYPE: DNA
<213> ORGANISM: Artificial Sequence
<220> FEATURE:
<223> OTHER INFORMATION: Forward primer (GSTM1)

<400> SEQUENCE: 2
ggagacagaa gaggagaaga ttcg                                            24

<210> SEQ ID NO 3
<211> LENGTH: 19
<212> TYPE: DNA
<213> ORGANISM: Artificial Sequence
<220> FEATURE:
<223> OTHER INFORMATION: Reverse primer (GSTM1)

<400> SEQUENCE: 3
tgcccagctg catatggtt                                                  19

<210> SEQ ID NO 4
<211> LENGTH: 28
<212> TYPE: DNA
<213> ORGANISM: Artificial Sequence
<220> FEATURE:
<223> OTHER INFORMATION: Probe (GSTM1)

<400> SEQUENCE: 4
tccatggtct ggttctccaa aatgtcca                                        28

<210> SEQ ID NO 5
<211> LENGTH: 26
<212> TYPE: DNA
<213> ORGANISM: Artificial Sequence
<220> FEATURE:
<223> OTHER INFORMATION: Forward primer (Control gene BRCA1)

<400> SEQUENCE: 5
gtctgctttt acatctgaac ctctgt                                          26

<210> SEQ ID NO 6
<211> LENGTH: 22
<212> TYPE: DNA
<213> ORGANISM: Artificial Sequence
<220> FEATURE:
<223> OTHER INFORMATION: Reverse primer (Control gene BRCA1)
```

```
<400> SEQUENCE: 6
agccctgagc agtcttcaga ga                                             22

<210> SEQ ID NO 7
<211> LENGTH: 28
<212> TYPE: DNA
<213> ORGANISM: Artificial Sequence
<220> FEATURE:
<223> OTHER INFORMATION: Probe (Control gene BRCA1)

<400> SEQUENCE: 7
actctcacac ccagatgctg cttcacct                                       28
```